United States Patent
Ramamurthi et al.

(10) Patent No.: US 10,813,993 B2
(45) Date of Patent: Oct. 27, 2020

(54) DISPLAY PLATFORM FROM BACTERIAL SPORE COAT PROTEINS

(71) Applicant: The United States of America, as represented by the Secretary, Department of Health and Human Services, Bethesda, MD (US)

(72) Inventors: Kumaran S. Ramamurthi, North Potomac, MD (US); I-Lin Wu, Bethesda, MD (US)

(73) Assignee: The United States of America as represented by the Secretary, Department of Health and Human Services, Bethesda, MD (US)

( * ) Notice: Subject to any disclaimer, the term of this patent is extended or adjusted under 35 U.S.C. 154(b) by 0 days.

(21) Appl. No.: 15/555,283

(22) PCT Filed: Aug. 7, 2015

(86) PCT No.: PCT/US2015/044316
§ 371 (c)(1),
(2) Date: Sep. 1, 2017

(87) PCT Pub. No.: WO2016/140702
PCT Pub. Date: Sep. 9, 2016

(65) Prior Publication Data
US 2018/0055925 A1 Mar. 1, 2018

Related U.S. Application Data

(60) Provisional application No. 62/127,738, filed on Mar. 3, 2015.

(51) Int. Cl.
*A61K 39/385* (2006.01)
*A61K 39/07* (2006.01)
*A61K 39/00* (2006.01)
*A61K 9/50* (2006.01)

(52) U.S. Cl.
CPC .......... *A61K 39/385* (2013.01); *A61K 9/5015* (2013.01); *A61K 39/07* (2013.01); *A61K 2039/543* (2013.01); *A61K 2039/55561* (2013.01); *A61K 2039/55572* (2013.01); *Y02A 50/386* (2018.01); *Y02A 50/394* (2018.01)

(58) Field of Classification Search
CPC .... A61K 2039/543; A61K 2039/55561; A61K 2039/55572; A61K 39/07; A61K 39/385; A61K 9/5015; Y02A 50/386; Y02A 50/394
See application file for complete search history.

(56) References Cited

U.S. PATENT DOCUMENTS

2011/0229556 A1  9/2011  Irvine et al.

FOREIGN PATENT DOCUMENTS

| WO | WO 02/046388 | 6/2002 |
| WO | WO 02/101026 | 12/2002 |
| WO | WO 2011/160026 | 12/2011 |

OTHER PUBLICATIONS

Skolnick et al. Trends in Biotechnology, 18: 34-39, 2000.*
Rudinger J. In: Peptide Hormones. (Ed) JA Parsons, University Park Press, pp. 1-7, 1976.*
Greenspan et al. Nature Biotechnology 17: 936-937, 1999.*
Ebmeier et al. Mol. Microbiol. 84: 682-696, 2012.*
Publication entitled 'What's the Difference between Chemotherapy Drugs and Antibody Drugs?', Dana-Farber Cancer Institute, pp. 1-4, 2017.*
The slides of the Aug. 9, 2014 talk entitled 'In vitro assembly of the Bacillus subtilis spore coat basement layer' given by I-Lin Wu, 2014.*
Amuguni et al., "*Bacillus subtilis*, A temperature resistant and needle free delivery system of immunogens," *Human Vaccines & Immunotherapeutics* 8(7): 979-986 (published online Jun. 15, 2012).
Gopalakrishnan et al., "Supported bilayers formed from different phospholipids on spherical silica substrates," *Langmuir* 25(10): 5455-5458 (May 19, 2009).
International Search Report from the parent PCT Application No. PCT/US2015/044316, 5 pages (dated Nov. 6, 2015).
Ricca et al., "Mucosal vaccine delivery by non-recombinant spores of *Bacillus subtilis,*" *Microbial Cell Factories* 13(1): 115 (Aug. 12, 2014).
Wang et al., "The coat morphogenetic protein SpoVID is necessary for spore encasement in *Bacillus subtilis,*" *Molecular Microbiology* 74(3):634-649 (Nov. 1, 2009).
Written Opinion from the parent PCT Application No. PCT/US2015/044316, 8 pages (dated Nov. 6, 2015).
Wu et al., "A versatile nano display platform from bacterial spore coat proteins," *Nature Communications* 6: 6777 (Apr. 9, 2015).

(Continued)

*Primary Examiner* — Sarvamangala Devi
(74) *Attorney, Agent, or Firm* — Klarquist Sparkman, LLP

(57) ABSTRACT

A particle construct is disclosed that includes a synthetic core with a solid surface coated with a lipid bilayer, SpoVM adhered to the lipid bilayer; and SpoIVA adsorbed to the SpoVM. In additional embodiments, an agent of interest can be covalently linked to the SpoIVA. In specific, non-limiting examples, the agent of interest is an enzyme, a detectable marker, a pharmaceutical compound, an immunosuppressant or a vaccine. Methods of using the particle constructs are disclosed, such as for treating infections, treating a tumor, delivering a vaccine, treating an autoimmune disorder or ameliorating an allergic reaction. Method are also disclosed for degrading an environmental pollutant. Methods are also disclosed for producing these particle constructs.

34 Claims, 11 Drawing Sheets

Specification includes a Sequence Listing.

(56) References Cited

OTHER PUBLICATIONS

Wu et al., "In vitro assembly of the *Bacillus subtilis* spore coat basement layer," Talk presented at the *Molecular Genetics of Bacteria and Phages* meeting in Madison, WI on Aug. 9, 2014. Abstract and slides.

* cited by examiner

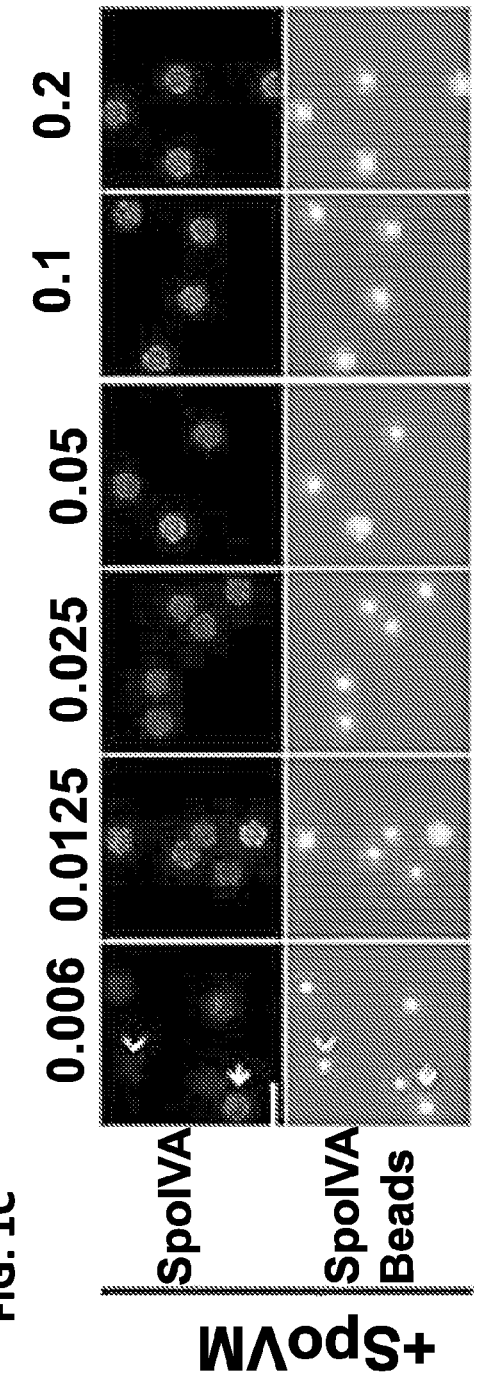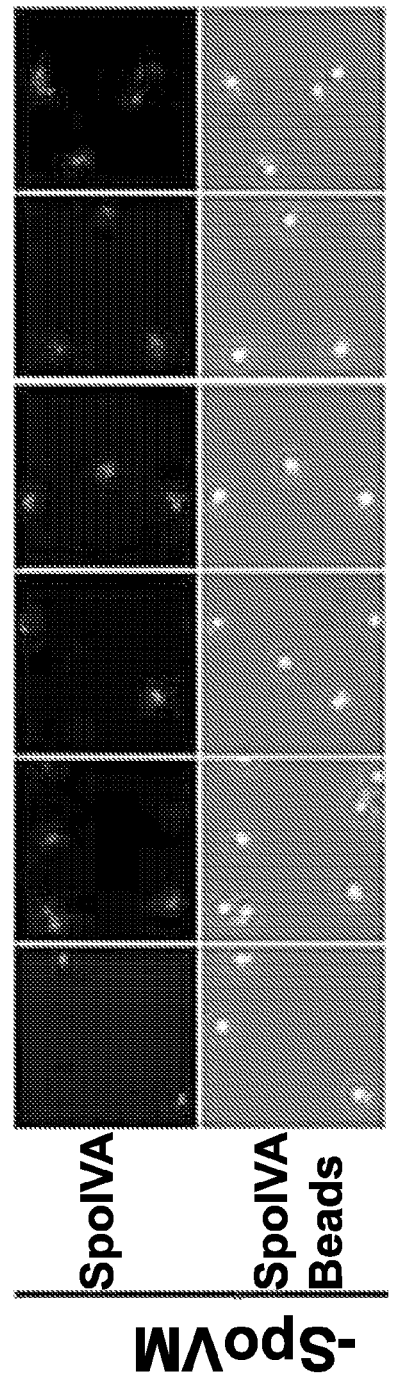

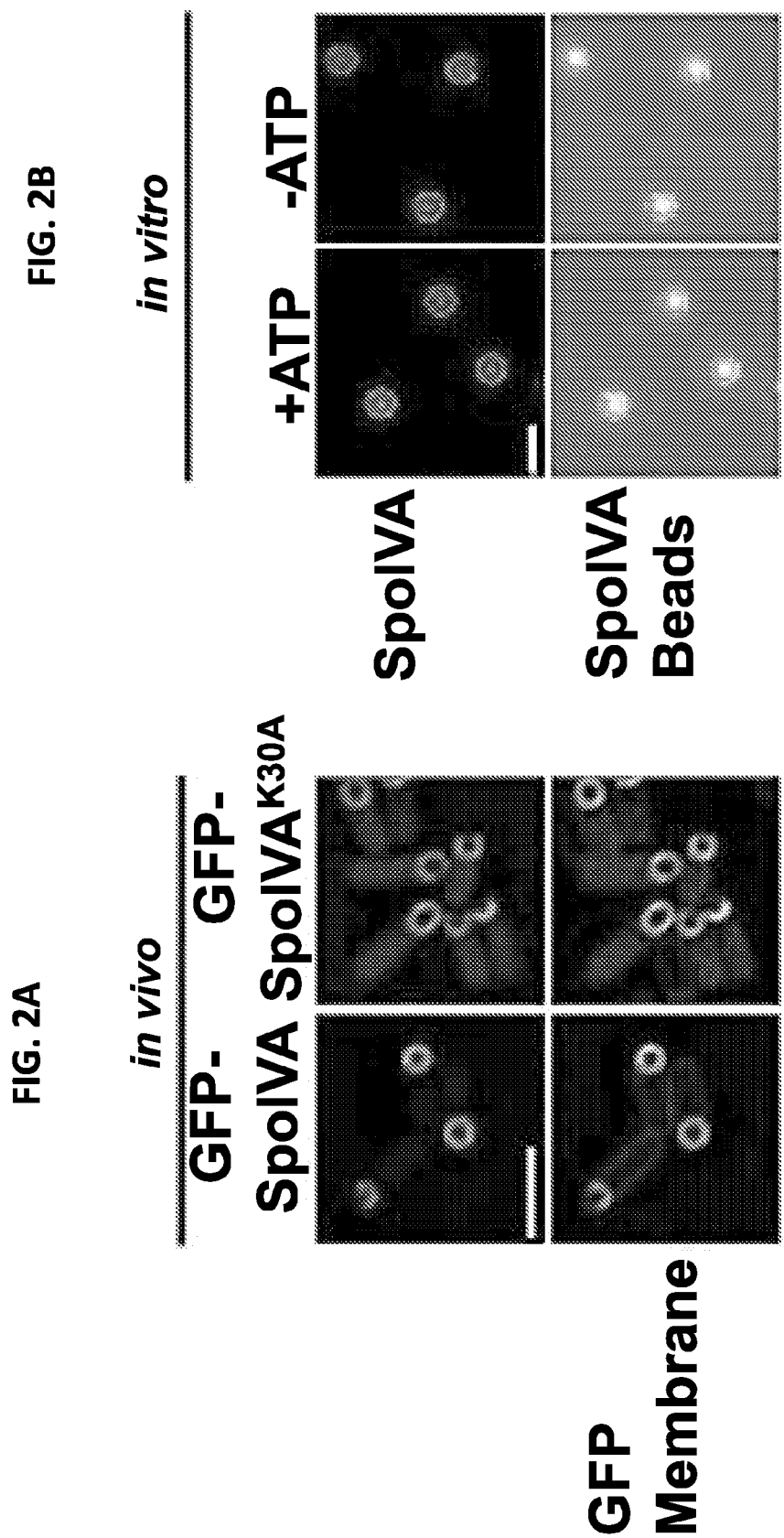

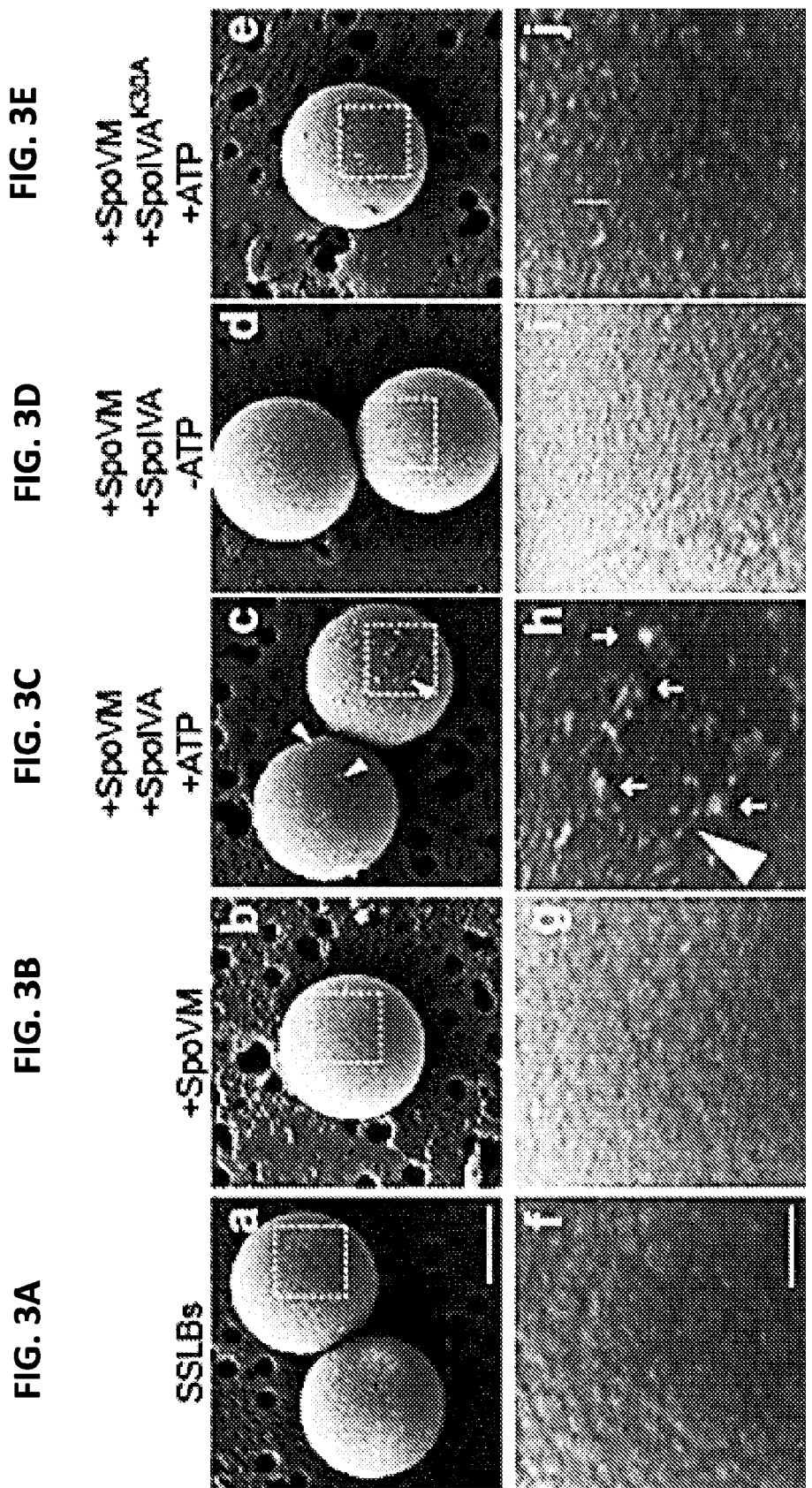

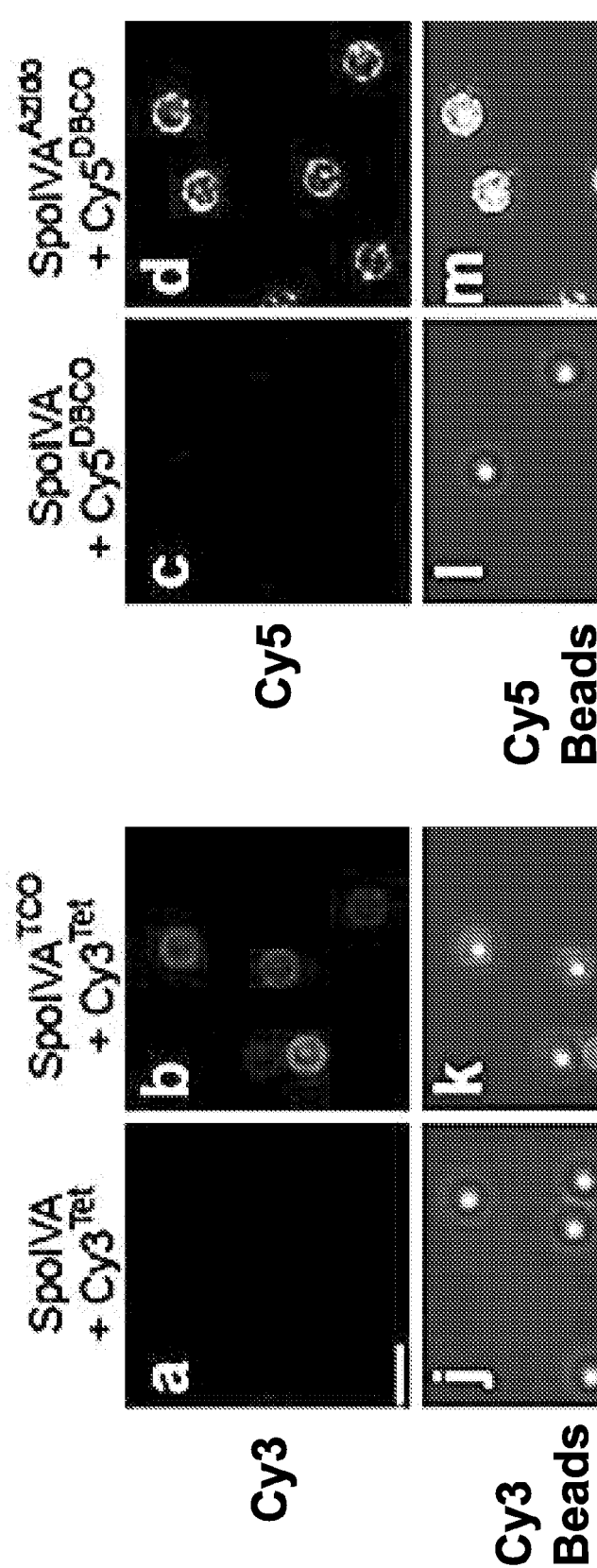

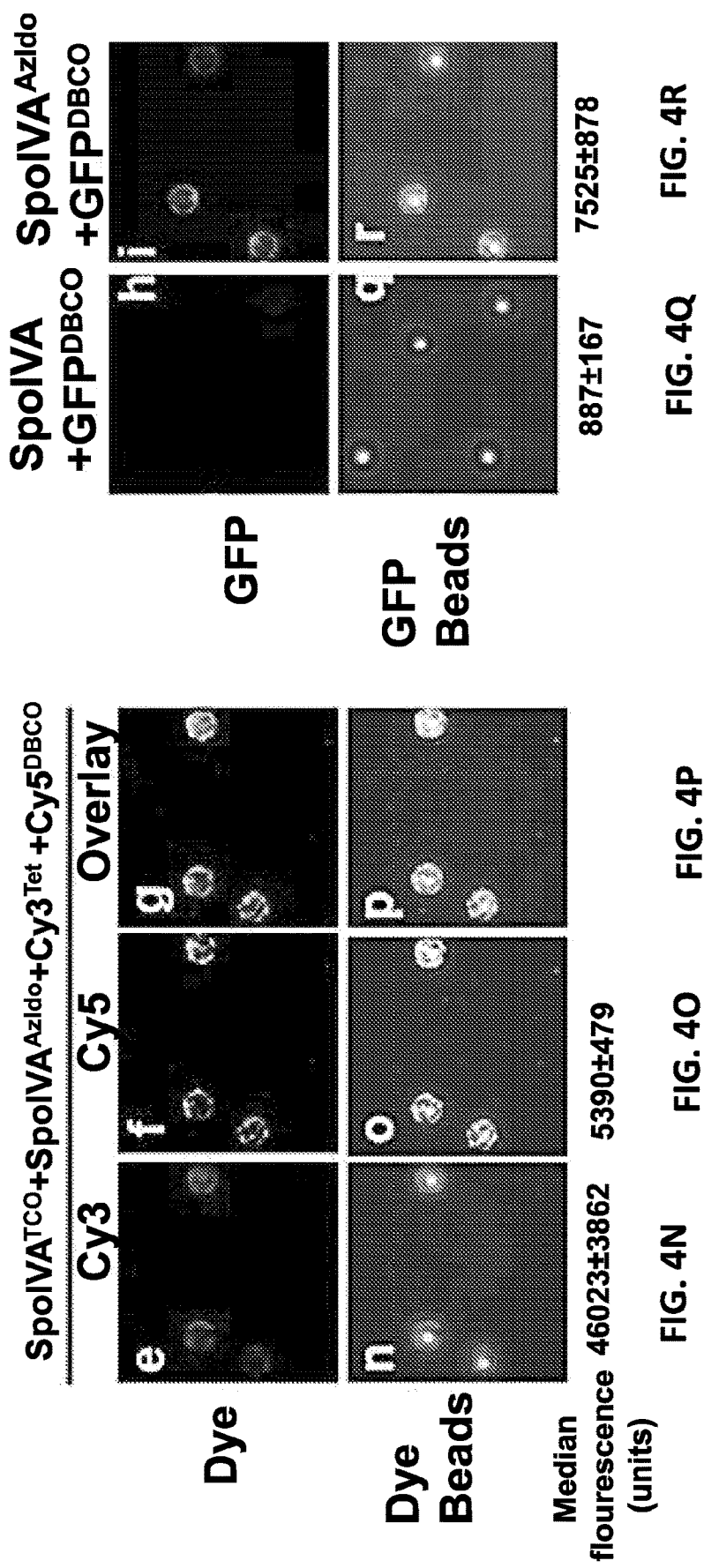

1. Coat support such as silica beads with *E. coli* phospholipid bilayer.

2. Incubate with **SpoVM

DISPLAY PLATFORM FROM BACTERIAL SPORE COAT PROTEINS

CROSS REFERENCE TO RELATED APPLICATIONS

This is the U.S. National Stage of International Application No. PCT/US2015/044316 filed Aug. 7, 2015, which was published in English under PCT Article 21(2), which claims the benefit of U.S. Provisional Application No. 62/127,738, filed Mar. 3, 2015, which is incorporated herein by reference.

FIELD OF THE DISCLOSURE

This relates to delivery systems, specifically to a particle construct that includes a synthetic core, a lipid bilayer, SpoVM and SpoIVA, and its use.

BACKGROUND

The bacterial spore coat is an about 1 μm diameter shell that encases endospores of the Gram-positive bacterium *Bacillus subtilis*. The coat is composed of about 70 different proteins (Henriques & Moran, *Annu Rev Microbiol* 61, 555-588 (2007): McKenney et al., *Nat Rev Microbiol* 11, 33-44 (2013)) and participates in protecting the spore's genetic material from environmental insults (Setlow, *J Appl Microbiol* 101, 514-525 (2006)). Spore formation initiates when the rod-shaped *B. subtilis* senses the depletion of nutrients in the environment and, instead of dividing by binary fission, divides asymmetrically to produce a smaller daughter cell (the "forespore") and a larger daughter cell (the "mother cell"), which are genetically identical, but differentiate to follow separate cell fates (Higgins and Dworkin, *FEMS Microbiol Rev* 36, 131-148 (2012), Tan and Ramamurthi *Environ Microbiol Rep* 6, 212-225 (2014), and Stragier and Losick, *Annu Rev Genet* 30, 297-241 (1996)), see also FIG. 1a. Next the mother cell engulfs the forespore such that the forespore eventually resides in the mother cell cytosol as a double membrane-bound organelle. Ultimately, the mother cell lyses, thereby releasing the mature, now dormant, spore into the environment. During sporulation, coat proteins are synthesized in the mother cell and localize onto the surface of the forespore to form the coat (McKenney and Eichenberger, *Mol Microbiol* 83, 245-260 (2012)). Coat assembly begins with the construction of a basement layer, which contains many proteins, including a structural protein termed SpoIVA (Roels and Losick, *J Bacteriol* 174, 575-585 (1992)) that displays a multi-domain architecture (Castaing et al., *FEMS Microbiol Lett* 358, 145-153 (2014)).

The N-terminus of SpoIVA binds and hydrolyzes adenosine tri-phosphate (ATP) (Ramamurthi and Losick, *Mol Cell* 31, 406-414 (2008), and Castaing et al., *Proc Natl Acad Sci USA* 110, E151-160 (2013)) via a predicted structural fold that resembles the TRAFAC class of P-loop GTPases (Leipe et al., *J Mol Biol* 317, 41-72 (2002)). ATP hydrolysis drives a structural change in SpoIVA that is required for its irreversible polymerization into a static polymer in vitro (Castaing et al., *Proc Natl Acad Sci USA* 110, E151-160 (2013)). SpoIVA is a soluble protein; it is thought to be anchored onto the surface of the developing forespore by SpoVM (Ramamurthi et al., *Mol Microbiol* 62, 1547-1557 (2006)), a 26 amino acid amphipathic α-helical protein (Levin et al., *Mol Microbiol* 9, 761-771 (1993), and Prajapati et al., *Biochim Biophys Acta* 1475, 353-359 (2000)) that preferentially embeds onto positively curved membranes with a radius of curvature similar to that of the forespore (Ramamurthi et al., *Science* 323, 1354-1357 (2009)). In vivo, proper assembly of the coat around the forespore absolutely requires SpoIVA and SpoVM (Levin et al., *Mol Microbiol* 9, 761-771 (1993), and Driks et al., *Genes Dev* 8, 234-244 (1994)), but it is not known if these two proteins are sufficient to initiate coat assembly.

The coat protects the spore from environmental insults, and is among the most durable static structures in biology. Due to extensive cross-linking among coat proteins, this structure has been recalcitrant to detailed biochemical analysis.

SUMMARY OF THE DISCLOSURE

It is disclosed herein that components of the basement layer of a spore coat can be reconstituted on a solid support coated with a lipid bilayer to create artificial spore-like particle constructs. An agent of interest can be covalently linked to the particle constructs. These particle constructs are a versatile display platforms for drugs, vaccines, enzymes that neutralize pollutants for environmental remediation, and any other molecule of interest.

In some embodiments, a synthetic particle construct is disclosed that includes a synthetic core with a solid surface coated with a lipid bilayer, SpoVM adhered to the lipid bilayer; and SpoIVA adsorbed to the SpoVM. In additional embodiments, an agent of interest can be covalently linked to the SpoIVA. In specific, non-limiting examples, the agent of interest is an enzyme, a detectable marker, a pharmaceutical compound, an immunosuppressant or a vaccine.

In additional embodiments, methods of using the particle constructs are disclosed. In specific non-limiting examples, the particle constructs can be used for treating infections, treating a tumor, delivering a vaccine, treating an autoimmune disorder or ameliorating an allergic reaction. The particle constructs can also be used for degrading an environmental pollutant.

In further embodiments, methods are disclosed for producing the particle constructs.

The foregoing and other features and advantages of the invention will become more apparent from the following detailed description of several embodiments which proceeds with reference to the accompanying figures.

BRIEF DESCRIPTION OF THE FIGURES

FIG. 1A-1F. Uniform adsorption of SpoIVA onto SSLBs requires SpoVM. (A) Schematic representation of sporulation in *Bacillus subtilis*. Membranes are depicted in yellow; cell wall is depicted in gray. Top: asymmetric division results in the formation of two genetically identical, but differently sized, compartments termed the forespore (FS, which ultimately becomes the mature spore) and the mother cell (MC). Middle panels: The asymmetric septum curves as the mother cell engulfs the forespore. SpoVM molecules are produced exclusively in the mother cell and preferentially bind to the positively curved membrane at the engulfing septum. SpoVM recruits SpoIVA, also produced exclusively in the mother cell, which polymerizes to form the basement layer of the spore coat. Bottom: eventually, the forespore resides as a double membrane-bound organelle, encased in the basement layer of the spore coat. Additional coat proteins (not depicted) assemble atop the basement layer. (B) Top: in vivo localization of GFP-SpoIVA in sporulating *B. subtilis* cells in the presence (left) or absence (right) of spoVM. Bottom: overlay of GFP fluorescence and membranes visualized with the fluorescent dye FM4-64. (C-D) Concentration-dependent adsorption of ALEXAFLUOR® 488-labeled SpoIVA onto SSLBs in the presence (C) or absence (D) of SpoVM. Overlay of DIC (gray) and ALEX-AFLUOR® 488 fluorescence for each panel is shown below. Arrow and arrowhead indicate an SSLB with high and low fluorescence, respectively. Scale bars: 3 µm. (E) Mean absorbance of SpoIVA$^{AF488}$ onto the surface of SSLBs in the presence (●) or absence (■) of SpoVM. Each data point represents at least 35 SSLB particles from three replicate experiments; error bars represent s.e.m. (F) Fraction of SSLBs displaying any fluorescence intensity above background level whose pattern of adsorption is qualitatively uniform, in the presence (●) or absence (■) of SpoVM.

FIGS. 2A-2D. Stable association of SpoIVA on the surface of spherical supported lipid bilayers (SSLBs) requires ATP. (A) In vivo localization of GFP-SpoIVA (left) or GFP-SpoIVA$^{K30A}$ (right, which is unable to bind ATP). Bottom: overlay of GFP fluorescence (green) and membranes visualized with FM4-64 (red) as described above. (B) Adsorption of SpoIVA$^{AF488}$ in vitro onto SSLBs coated with SpoVM in the presence (left) or absence (right) of ATP. Scale bars: 3 µm. (C) Concentration-dependent adsorption of SpoIVA$^{AF488}$ onto SSLBs coated with SpoVM in the presence (●) or absence (■) of ATP. (D) Retention of SpoIVA$^{AF488}$ on the surface of SSLBs, adsorbed either in the presence (●) or absence (■) of ATP at different time points after competition with exogenously added excess, unlabeled purified SpoIVA. Each data point represents at least 35 SSLB particles from three replicate experiments; error bars represent s.e.m.

FIGS. 3A-3J. Surface topography of synthetic spore husk-encased lipid bilayer (SSHEL) particles. Top: Scanning electron micrographs of SSLBs (A); SSLBs coated with SpoVM (B); SSLBs coated with SpoVM and SpoIVA in the presence (C) or absence (D) of ATP, or coated with SpoVM and SpoIVA$^{K30A}$ in the presence of ATP (E). (F-J) Higher magnification view of indicated areas in a-e, respectively. Arrows: protrusions; arrowheads: short filaments. Scale bar: 1 µm (a-e); 250 nm (F-J).

FIGS. 4A-4R. Covalent modification of the surface of SSHEL particles with small molecules or protein of interest. (A-B) Modification of the surface of SSHEL particles, with Tetrazine-labeled Cy3 fluorophore, decorated with either (A) SpoIVA or (B) SpoIVA labeled with TCO-PEG$_3$. (C-D) Modification of the surface of SSHEL particles, with DBCO-labeled Cy5 fluorophore, decorated with either (C) SpoIVA or (D) SpoIVA labeled with Azido-PEG$_3$. (E-G) Stepwise modification of SSHEL particles, with Cy3$^{Tet}$ and Cy5$^{DBCO}$, decorated with SpoIVA$^{TCO}$ and SpoIVA$^{Azido}$, viewed using the Cy3 filter (E) or the Cy5 filter (F). (G) Overlay of (E) and (F). (H-I) Modification of SSHEL particles, with DBCO-labeled GFP, decorated with SpoIVA (H), or SpoIVA$^{Azido}$ (I). (J-R) Overlay of DIC (gray) and fluorescence from (A-I), respectively. Median fluorescence intensity of decorated SSHEL particles (arbitrary units) is displayed below each panel. Scale bar: 3 µm. Median fluorescence intensities were determined from three replicate experiments; error is s.e.m. (n>40).

SEQUENCE LISTING

Figure 1B:
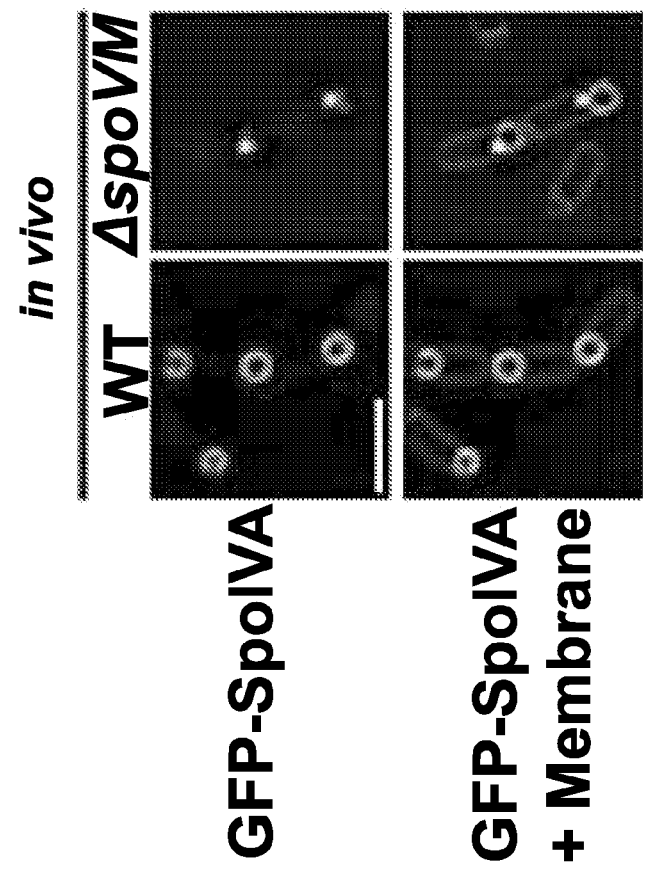
Figure 1A:
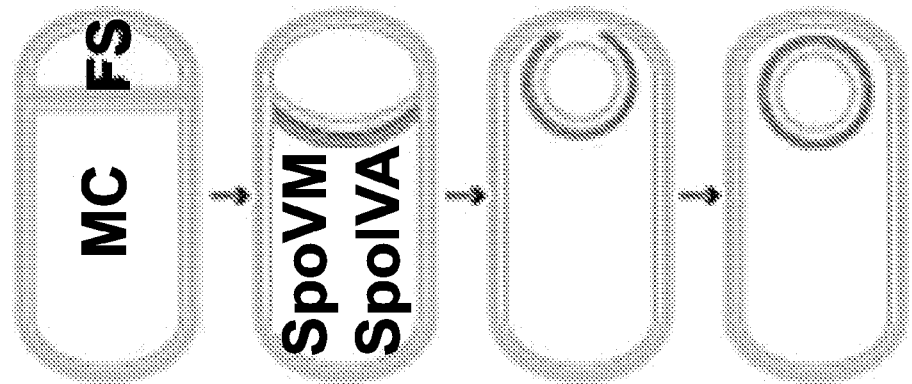

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file 4239_94407_05_Sequence_Listing.txt, Sep. 1, 2017, 80_KB, which is incorporated by reference herein.

SEQ ID NO: 1 is the amino acid sequence of *B. subtilis* SpoVM.

SEQ ID NO: 2 is the amino acid sequence of *B. subtilis* SpoIVA.

SEQ ID NOs: 3-11 are the amino acid sequence of additional SpoVM polypeptides.

SEQ ID NOs: 12-28 are the amino acid sequence of additional SpoIVA polypeptides.

DETAILED DESCRIPTION OF SEVERAL EMBODIMENTS

In vivo-modified bacterial spores can be used as a unique molecular adjuvant with emergent interests for mucosal vaccine design (Ricca et al., *Microb Cell Fact* 13, 115 (2014), and Huang et al., *Vaccine* 28, 1021-1030 (2010)), and for the display of enzymes that aid in environmental remediation efforts (Knecht et al., *Anal Bioanal Chem* 400, 977-989 (2011) and Hinc et al. *Res Microbiol* 161, 757-764 (2010)). However, particle constructs that include one or more small molecules and proteins of interest provide several potential benefits. First, these particle constructs are of defined composition, so their surfaces are devoid of extraneous proteins that can interfere with a specific function of a displayed protein or molecule. Second, reconstruction of the display platform in vitro eschews the use of a living, potentially genetically modified, organism capable of replication or horizontal gene transfer, in the final product. Finally, by employing an in vitro system, the density of a single displayed molecule may be finely tuned by adjusting the ratio of modifiable and unmodifiable SpoIVA used to construct SSHEL particles. This may be particularly useful, for example, when the magnitude of an immune response may be sensitive to the density of a particular antigen.

Additionally, current technologies permit the display of multiple ligands on the surface of *B. subtilis* spores, for example, by incorporating a streptavidin-fused SpoVIA protein on the spore surface, which can then interact with multiple biotin-conjugated molecules of interest (see Nguyen et al., *J Drug Target* 21, 528-541 (2013)). Using the system described here, a large number of molecules can be specifically and covalently displayed on the surface of SSHEL particles, and that this number is limited only by the number of orthogonal conjugation molecules available to perform the click chemistry reactions. The relative ratios of the displayed molecules on a bead may be precisely adjusted simply by adjusting the ratios of specifically modified SpoIVA molecules used to construct the SSHELs.

Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Adjuvant: A vehicle used to enhance antigenicity. Adjuvants include a suspension of minerals (alum, aluminum hydroxide, or phosphate) on which antigen is adsorbed; or water-in-oil emulsion, for example, in which antigen solution is emulsified in mineral oil (Freund incomplete adjuvant), sometimes with the inclusion of killed mycobacteria (Freund's complete adjuvant) to further enhance antigenicity (inhibits degradation of antigen and/or causes influx of macrophages). Immunostimulatory oligonucleotides (such as those including a CpG motif) can also be used as adjuvants. Adjuvants include biological molecules (a "biological adjuvant"), such as costimulatory molecules. Exemplary adjuvants include IL-2, RANTES, GM-CSF, TNF-α, IFN-γ, G-CSF, LFA-3, CD72, B7-1, B7-2, OX-40L, 4-1BBL and toll-like receptor (TLR) agonists, such as TLR-9 agonists. The person of ordinary skill in the art is familiar with adjuvants (see, e.g., Singh (ed.) Vaccine Adjuvants and Delivery Systems. Wiley-Interscience, 2007). Adjuvants can be used in combination with the disclosed SSHEL particles.

Allergen: A substance that can induce an allergic or asthmatic response in a susceptible subject. The list of allergens is enormous and can include pollens, insect venoms, animal dander dust, fungal spores and drugs (e.g. penicillin). Examples of natural, animal and plant allergens include proteins specific to the following genera: Canine (*Canis familiaris*); Dermatophagoides (e.g. *Dermatophagoides farinae*); Felis (*Felis domesticus*); Ambrosia (*Ambrosia artemiisfolia*); Lolium (e.g. *Lolium perenne* or *Lolium multiflorum*); Cryptomeria (*Cryptomeria japonica*); Alternaria (*Alternaria alternata*); Alder; Alnus (*Alnus gultinosa*); Betula (*Betula verrucosa*); Quercus (*Quercus alba*); Olea (*Olea europa*); Artemisia (*Artemisia vulgaris*); Plantago (e.g. *Plantago lanceolata*); Parietaria (e.g. *Parietaria officinalis* or *Parietaria judaica*); Blattella (e.g. *Blattella germanica*); Apis (e.g. *Apis multiflorum*); Cupressus (e.g. *Cupressus sempervirens, Cupressus arizonica* and *Cupressus macrocarpa*); Juniperus (e.g. *Juniperus sabinoides, Juniperus virginiana, Juniperus communis* and *Juniperus ashei*); Thuya (e.g. *Thuya orientalis*); Chamaecyparis (e.g. *Chamaecyparis obtusa*); Periplaneta (e.g. *Periplaneta americana*); Agropyron (e.g. *Agropyron repens*); Secale (e.g. *Secale cereale*); Triticum (e.g. *Triticum aestivum*); Dactylis (e.g. *Dactylis glomerata*); Festuca (e.g. *Festuca elatior*); Poa (e.g. *Poa pratensis* or *Poa compressa*); Avena (e.g. *Avena sativa*); Holcus (e.g. *Holcus lanatus*); Anthoxanthum (e.g. *Anthoxanthum odoratum*); Arrhenatherum (e.g. *Arrhenatherum elatius*); Agrostis (e.g. *Agrostis alba*); Phleum (e.g. *Phleum pratense*); Phalaris (e.g. *Phalaris arundinacea*); Paspalum (e.g. *Paspalum notatum*); Sorghum (e.g. *Sorghum halepensis*); and Bromus (e.g. *Bromus inermis*). The term "allergy" refers to acquired hypersensitivity to a substance (allergen). An "allergic reaction" is the response of an immune system to an allegen in a subject allergic to the allergen. Allergic conditions include eczema, allergic rhinitis or coryza, hay fever, bronchial asthma, urticaria (hives) and food allergies, and other atopic conditions.

Animal: Living multi-cellular vertebrate organisms, a category that includes, for example, mammals and birds. The term mammal includes both human and non-human mammals. Similarly, the term "subject" includes both human and veterinary subjects.

Antibody: A polypeptide substantially encoded by an immunoglobulin gene or immunoglobulin genes, or antigen binding fragments thereof, which specifically binds and recognizes an analyte (antigen). Immunoglobulin genes include the kappa, lambda, alpha, gamma, delta, epsilon and mu constant region genes, as well as the myriad immunoglobulin variable domain genes. The term "antibody," as used herein, also includes antigen binding fragments either produced by the modification of whole antibodies or those synthesized de novo using recombinant DNA methodologies.

Non-limiting examples of antibodies include, for example, intact immunoglobulins and variants and fragments thereof known in the art that retain specific binding affinity for the antigen. Antibodies also include genetically engineered forms such as chimeric antibodies (such as humanized murine antibodies) and heteroconjugate antibodies (such as bispecific antibodies). See also, *Pierce Catalog and Handbook*, 1994-1995 (Pierce Chemical Co., Rockford, Ill.); Kuby, J., Immunology, 3$^{rd}$ Ed., W.H. Freeman & Co., New York, 1997.

Examples of antigen binding fragments include: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab')$_2$, the fragment of the antibody obtained by treating whole antibody with the enzyme pepsin without subsequent reduction; (4) F(ab')$_2$, a dimer of two Fab' fragments held together by two disulfide bonds; (5) Fv, a genetically engineered fragment containing the variable domain of the light chain and the variable domain of the heavy chain expressed as two chains; and (6) single chain antibody ("SCA"), a genetically engineered molecule containing the variable domain of the light chain, the variable domain of the heavy chain, linked by a suitable polypeptide linker as a genetically fused single chain molecule.

A single-chain antibody (scFv) is a genetically engineered molecule containing the $V_H$ and $V_L$ domains of one or more antibody(ies) linked by a suitable polypeptide linker as a genetically fused single chain molecule (see, for example, Bird et al., Science, 242:423-426, 1988; Huston et al., Proc. Natl. Acad. Sci., 85:5879-5883, 1988). In a dsFv the heavy and light chain variable chains have been mutated to introduce a disulfide bond to stabilize the association of the chains. Diabodies also are included, which are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see, for example, Holliger et al., *Proc. Natl. Acad. Sci.*, 90:6444-6448, 1993; Poljak et al., *Structure,* 2:1121-1123, 1994).

An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a bispecific or bifunctional antibody has two different binding sites. Typically, a naturally occurring antibody has heavy (H) chains and light (L) chains interconnected by disulfide bonds. There are two types of light chain, lambda (λ) and kappa (κ). There are five main heavy chain classes (or isotypes) which determine the functional activity of an antibody molecule: IgM, IgD, IgG, IgA and IgE.

Each heavy and light chain contains a constant region and a variable region (the regions are also known as "domains"). In several embodiments, the heavy and the light chain variable regions combine to specifically bind the antigen. In additional embodiments, only the heavy chain variable region is required. For example, naturally occurring camelid antibodies consisting of a heavy chain only are functional and stable in the absence of light chain (see, e.g., Hamers-Casterman et al., *Nature,* 363:446-448, 1993; Sheriff et al., *Nat. Struct. Biol.,* 3:733-736, 1996). Light and heavy chain variable regions contain a "framework" region interrupted by three hypervariable regions, also called "complementarity-determining regions" or "CDRs" (see, e.g., Kabat et al., *Sequences of Proteins of Immunological Interest*, U.S. Department of Health and Human Services, 1991). The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The amino acid sequence boundaries of a given CDR can be readily determined using any of a number of well-known schemes, including those described by Kabat et al. ("Sequences of Proteins of Immunological Interest," 5th Ed. Public Health Service, National Institutes of Health, Bethesda, Md., 1991; "Kabat" numbering scheme), Al-Lazikani et al., (JMB 273,927-948, 1997; "Chothia" numbering scheme), and Lefranc et al. ("IMGT unique numbering for immunoglobulin and T cell receptor variable domains and Ig superfamily V-like domains," Dev. Comp. Immunol., 27:55-77, 2003; "IMGT" numbering scheme). The CDRs of each chain are typically referred to as CDR1, CDR2, and CDR3 (from the N-terminus to C-terminus), and are also typically identified by the chain in which the particular CDR is located. Thus, a $V_H$ CDR3 is the CDR3 from the variable region of the heavy chain of the antibody in which it is found, whereas a $V_L$ CDR1 is the CDR1 from the variable region of the light chain of the antibody in which it is found. Light chain CDRs are sometimes referred to as LCDR1, LCDR2, and LCDR3. Heavy chain CDRs are sometimes referred to as LCDR1, LCDR2, and LCDR3.

References to "$V_H$" or "VH" refer to the variable domain of an immunoglobulin heavy chain, including that of an antigen binding fragment, such as Fv, scFv, dsFv or Fab.

References to "$V_L$" or "VL" refer to the variable domain of an immunoglobulin light chain, including that of an Fv, scFv, dsFv or Fab.

A "monoclonal antibody" is an antibody produced by a single clone of B-lymphocytes or by a cell into which the light and heavy chain genes of a single antibody have been transfected, or a progeny thereof. Monoclonal antibodies are produced by methods known to those of skill in the art, for instance by making hybrid antibody-forming cells from a fusion of myeloma cells with immune spleen cells. These fused cells and their progeny are termed "hybridomas." Monoclonal antibodies include chimeric, humanized and fully human monoclonal antibodies. In some examples monoclonal antibodies are isolated from a subject. The amino acid sequences of such isolated monoclonal antibodies can be determined. Monoclonal antibodies can have conservative amino acid substitutions which have substantially no effect on antigen binding or other immunoglobulin functions. (See, for example, Harlow & Lane, *Antibodies, A Laboratory Manual*, Cold Spring Harbor Publications, New York (1988).)

A "chimeric" antibody is an antibody including a framework region from one antibody and one or more CDRs from a heterologous antibody. The framework regions and the CDRs can be from antibodies from the same or different species.

A "humanized" antibody is an antibody including a human framework region and one or more CDRs from a non-human (such as a mouse, rat, or synthetic) immunoglobulin. The non-human antibody providing the CDRs is termed a "donor," and the human antibody providing the framework is termed an "acceptor." In one embodiment, all the CDRs are from the donor antibody in a humanized antibody. Constant regions need not be present, but if they are, they must be substantially identical to human antibody constant regions, such as at least about 85-90%, such as about 95% or more identical. Hence, all parts of a humanized antibody, except possibly the CDRs, are substantially identical to corresponding parts of natural human antibody sequences. A "humanized antibody" is an antibody including a humanized light chain and a humanized heavy chain. A humanized antibody binds to the same antigen as the donor antibody that provides the CDRs. The acceptor framework of a humanized immunoglobulin or antibody may have a limited number of substitutions by amino acids taken from the donor framework.

Humanized, chimeric or other monoclonal antibodies can have additional conservative amino acid substitutions, such as in the framework region, which have substantially no effect on antigen binding or other immunoglobulin functions. Humanized and chimeric immunoglobulins can be constructed by means of genetic engineering (for example, see U.S. Pat. No. 5,585,089).

Antigen: A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens. The term "antigen" includes all related antigenic epitopes.

Anti-infectious agent: A substance (such as a chemical compound, protein, antisense oligonucleotide, or other molecule) of use in treating infection of a subject. Anti-infectious agents include, but are not limited to, anti-fungals, anti-virals, and antibiotics.

Asthma: A disorder of the respiratory system characterized by inflammation, narrowing of the airways and increased reactivity of the airways to inhaled agents. Asthma is frequently, although not exclusively associated with atopic or allergic symptoms.

Autoimmune disorder: A disorder in which the immune system produces an immune response (e.g. a B cell or a T cell response) against an endogenous antigen, with consequent injury to tissues.

Chemotherapy; chemotherapeutic agents: As used herein, any chemical agent with therapeutic usefulness in the treatment of diseases characterized by abnormal cell growth. Such diseases include tumors, neoplasms, and cancer as well as diseases characterized by hyperplastic growth such as psoriasis. In one embodiment, a chemotherapeutic agent is an agent of use in treating neoplasms such as solid tumors. In one embodiment, a chemotherapeutic agent is radioactive molecule. One of skill in the art can readily identify a chemotherapeutic agent of use (e.g. see Slapak and Kufe, *Principles of Cancer Therapy*, Chapter 86 in Harrison's Principles of Internal Medicine, 14th edition; Perry et al., *Chemotherapy*, Ch. 17 in Abeloff, Clinical Oncology $2^{nd}$ ed., © 2000 Churchill Livingstone, Inc; Baltzer L., Berkery R. (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993). Chemotherapeutic agents include those known by those skilled in the art, including but not limited to: 5-fluorouracil (5-FU), azathioprine, cyclophosphamide, antimetabolites (such as Fludarabine), antineoplastics (such as Etoposide, Doxorubicin, methotrexate, and Vincristine), carboplatin, cisplatinum and the taxanes, such as taxol. Rapamycin has also been used as a chemotherapeutic.

Conservative variants: "Conservative" amino acid substitutions are those substitutions that do not substantially decrease the activity of a protein, such as SpoIVA or SpoVM, such as the binding of SpoIVA and SpoVM. The term conservative variation also includes the use of a substituted amino acid in place of an unsubstituted parent amino acid, provided protein retains the desired activity.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Contacting: Placement in direct physical association, for example solid, liquid or gaseous forms. Contacting includes, for example, direct physical association of fully- and partially-solvated molecules.

Cytokine: Proteins made by cells that affect the behavior of other cells, such as lymphocytes. In one embodiment, a cytokine is a chemokine, a molecule that affects cellular trafficking. Cytokines include the interleukins.

Detectable marker or Label: A detectable molecule (also known as a label) that is conjugated directly or indirectly to a second molecule to facilitate detection of the second molecule. For example, the detectable marker can be capable of detection by ELISA, spectrophotometry, flow cytometry, microscopy or diagnostic imaging techniques (such as CT scans, MRIs, ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). In one example, a "labeled protein" refers to incorporation of another molecule in the protein, and a "labeled particle" refers to incorporation of label into the particle. For example, the label is a detectable marker, such as the incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionuclides (such as $^{35}S$ or $^{131}I$), fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance. Methods for using detectable markers and guidance in the choice of detectable markers appropriate for various purposes are discussed for example in Sambrook et al. (*Molecular Cloning: A Laboratory Manual*, Cold Spring Harbor, N.Y., 2012) and Ausubel et al. (*In Current Protocols in Molecular Biology*, John Wiley & Sons, New York, 1998).

Detecting: To identify the existence, presence, or fact of something. General methods of detecting are known to the skilled artisan and may be supplemented with the protocols and reagents disclosed herein.

Epitope: An antigenic determinant. These are particular chemical groups or peptide sequences on a molecule that are antigenic, i.e. that elicit a specific immune response. An antibody binds a particular antigenic epitope. Generally, an enzyme reduces the activation energy of a specific biochemical reaction.

Enzyme: A macromolecular biological catalyst. Enzymes are usually very specific as to which reactions they catalyze and the substrates that are involved in these reactions. Complementary shape, charge and hydrophilic/hydrophobic characteristics of enzymes and substrates are responsible for this specificity. At the maximum reaction rate ($V_{max}$) of the enzyme, all the enzyme active sites are bound to substrate, and the amount of enzyme-substrate (ES) complex is the same as the total amount of enzyme. The Michaelis-Menten constant ($K_m$), is the substrate concentration required for an enzyme to reach one-half its maximum reaction rate; generally, each enzyme has a characteristic $K_m$ for a given substrate. The turnover number ($k_{cat}$) is the number of substrate molecules handled by one active site per second. The efficiency of an enzyme can be expressed in terms of $k_{cat}/K_m$.

Environmental Pollutant: A contaminants in a natural environment that causes adverse change—Pollution can take the form of chemical substances or energy, such as noise, heat or light. A pollutant generally has undesired effects, or adversely affects the usefulness of a resource. A pollutant may cause long- or short-term damage by changing the growth rate of plant or animal species, or by interfering with human amenities, comfort, health, or property values. Persistent organic pollutants (POPs) as used herein include, but are not limited to, polychlorinated biphenyls (PCBs) and polyaromatic hydrocarbons (PAH), or polychlorinated dibenzo-p-dioxins and polychlorinated dibenzo-furans (PCDD/Fs) and pesticide residues and other POPs that are recognized by regulatory bodies to be problematic and limiting to development.

Heterologous: Components that do not occur together in nature in the same structural relationship to one another.

Immune response: A response of a cell of the immune system, such as a B cell or T cell to a stimulus. In one embodiment, the response is specific for a particular antigen (an "antigen-specific response"). A "parameter of an immune response" is any particular measurable aspect of an immune response, including, but not limited to, cytokine secretion (IL-6, IL-10, IFNγ, etc.), immunoglobulin production, dendritic cell maturation, and proliferation of a cell of the immune system. One of skill in the art can readily determine an increase in any one of these parameters, using known laboratory assays. In one specific non-limiting example, to assess cell proliferation, incorporation of $^3$H-thymidine can be assessed. A "substantial" increase in a parameter of the immune response is a significant increase in this parameter as compared to a control. Specific, non-limiting examples of a substantial increase are at least about a 50% increase, at least about a 75% increase, at least about a 90% increase, at least about a 100% increase, at least about a 200% increase, at least about a 300% increase, and at least about a 500% increase. One of skill in the art can readily identify a significant increase using known statistical methods.

Immunogenic composition: A composition comprising an antigen that induces an immune response, such as a measurable CTL response against virus expressing the antigen, or a measurable B cell response (such as production of antibodies) against the antigen. As such, an immunogenic composition includes one or more antigens (for example, polypeptide antigens) or antigenic epitopes, such as in a particle construct. An immunogenic composition can also include one or more additional components capable of eliciting or enhancing an immune response, such as an excipient, carrier, and/or adjuvant. In certain instances, immunogenic compositions are administered to elicit an immune response that protects the subject against symptoms or conditions induced by a pathogen. In one example, an "immunogenic composition" includes a particle construct that induces a measurable CTL response and/or induces a measurable B cell response (such as production of antibodies). For in vivo use, the immunogenic composition will typically include the particle construct in pharmaceutically acceptable carriers, and/or other agents. Immunogenic compositions can include adjuvants, which are well known to one of skill in the art. However, in some embodiments, an immunogenic composition does not include an adjuvant.

Immunosuppressant: An agent that prevents or significantly reduces an activity of the immune system.

Infectious agent: An agent that can infect a subject, including, but not limited to, viruses, bacteria, and fungi.

Examples of infectious virus include: Retroviridae; Picornaviridae (for example, polio viruses, hepatitis A virus; enteroviruses, human coxsackie viruses, rhinoviruses, echoviruses); Calciviridae (such as strains that cause gastroenteritis); Togaviridae (for example, equine encephalitis viruses, rubella viruses); Flaviridae (for example, dengue viruses, encephalitis viruses, yellow fever viruses); Coronaviridae (for example, coronaviruses); Rhabdoviridae (for example, vesicular stomatitis viruses, rabies viruses); Filoviridae (for example, ebola viruses);

Paramyxoviridae (for example, parainfluenza viruses, mumps virus, measles virus, respiratory syncytial virus); Orthomyxoviridae (for example, influenza viruses); Bungaviridae (for example, Hantaan viruses, bunga viruses, phleboviruses and Nairo viruses); Arena viridae (hemorrhagic fever viruses); Reoviridae (e.g., reoviruses, orbiviurses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and HSV-2, varicella zoster virus, cytomegalovirus (CMV), herpes viruses); Poxviridae (variola viruses, vaccinia viruses, pox viruses); and Iridoviridae (such as African swine fever virus); and unclassified viruses (for example, the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses).

Examples of infectious bacteria include: *Helicobacter pyloris, Borelia burgdorferi, Legionella pneumophilia, Mycobacteria* sps (such as. *M. tuberculosis, M. avium, M. intracellulare, M. kansaii, M. gordonae), Staphylococcus aureus, Neisseria gonorrhoeae, Neisseria meningitidis, Listeria monocytogenes, Streptococcus pyogenes* (Group A *Streptococcus), Streptococcus agalactiae* (Group B *Streptococcus), Streptococcus* (viridans group), *Streptococcus faecalis, Streptococcus bovis, Streptococcus (anaerobic* sps.), *Streptococcus pneumoniae*, pathogenic *Campylobacter* sp., *Enterococcus* sp., *Haemophilus influenzae, Bacillus antracis, Corynebacterium diphtheriae, Corynebacterium* sp., *Erysipelothrix rhusiopathiae, Clostridium perfringers, Clostridium tetani, Enterobacter aerogenes, Klebsiella pneumoniae, Pasteurella multocida, Bacteroides* sp., *Fusobacterium nucleatum, Streptobacillus moniliformis, Treponema pallidium, Treponema pertenue, Leptospira*, and *Actinomyces israeli*.

Examples of infectious fungi include, but are not limited to, *Cryptococcus neoformans, Histoplasma capsulatum, Coccidioides immitis, Blastomyces dermatitidis, Chlamydia trachomatis, Candida albicans*.

Other infectious organisms (such as protists) include: *Plasmodium falciparum* and *Toxoplasma gondii*.

Isolated: An "isolated" biological component (such as a nucleic acid, peptide or protein) has been substantially separated, produced apart from, or purified away from other biological components in the cell of the organism in which the component naturally occurs, i.e., other chromosomal and extrachromosomal DNA and RNA, and proteins. Nucleic acids, peptides and proteins which have been "isolated" thus include nucleic acids and proteins purified by standard purification methods. The term also embraces nucleic acids, peptides and proteins prepared by recombinant expression in a host cell as well as chemically synthesized nucleic acids. An "isolated" particle has been substantially separated, produced apart from, or purified away from the environment from which it was produced, such as the reagents and/or reaction.

Mammal: This term includes both human and non-human mammals. Similarly, the term "subject" includes both human and veterinary subjects.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences." "cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Recombinant nucleic acid" refers to a nucleic acid having nucleotide sequences that are not naturally joined together. This includes nucleic acid vectors including an amplified or assembled nucleic acid which can be used to transform a suitable host cell. A host cell that includes the recombinant nucleic acid is referred to as a "recombinant host cell." The gene is then expressed in the recombinant host cell to produce, e.g., a "recombinant polypeptide." A recombinant nucleic acid may serve a non-coding function (e.g., promoter, origin of replication, ribosome-binding site, etc.) as well.

A polynucleotide or nucleic acid sequence refers to a polymeric form of nucleotide at least 10 bases in length. A recombinant polynucleotide includes a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides can be ribonucleotides, deoxyribonucleotides, or modified forms of either nucleotide. The term includes single- and double-stranded forms of DNA.

Oligonucleotide or "oligo": Multiple nucleotides (i.e. molecules comprising a sugar (e.g. ribose or deoxyribose) linked to a phosphate group and to an exchangeable organic base, which is either a substituted pyrimidine (Py) (e.g. cytosine (C), thymine (T) or uracil (U)) or a substituted purine (Pu) (e.g. adenine (A) or guanine (G)). The term "oligonucleotide" as used herein refers to both oligoribonucleotides (ORNs) and oligodeoxynucleotides (ODNs). The term "oligonucleotide" also includes oligonucleosides (i.e. an oligonucleotide minus the phosphate) and any other organic base polymer. Oligonucleotides can be obtained from existing nucleic acid sources (e.g. genomic or cDNA), but are preferably synthetic (e.g. produced by oligonucleotide synthesis).

A "stabilized oligonucleotide" is an oligonucleotide that is relatively resistant to in vivo degradation (for example via an exo- or endo-nuclease). In one embodiment, a stabilized oligonucleotide has a modified phosphate backbone. One specific, non-limiting example of a stabilized oligonucleotide has a phosphorothioate modified phosphate backbone (wherein at least one of the phosphate oxygens is replaced by sulfur). Other stabilized oligonucleotides include: non-ionic DNA analogs, such as alkyl- and aryl-phosphonates (in which the charged phosphonate oxygen is replaced by an alkyl or aryl group), phosphodiester and alkylphosphotriesters, in which the charged oxygen moiety is alkylated. Oligonucleotides which contain a diol, such as tetraethyleneglycol or hexaethyleneglycol, at either or both termini have also been shown to be substantially resistant to nuclease degradation.

An "immunostimulatory oligodeoxynucleotide," "immunostimulatory CpG containing oligodeoxynucleotide," "CpG ODN," refers to an oligodeoxynucleotide, which contains a cytosine, guanine dinucleotide sequence and (e.g. has a mitogenic effect or induces cytokine production) vertebrate immune cells. In one embodiment, an immunostimulatory CpG ODN stimulates a parameter of an immune response in a subject. The cytosine, guanine is unmethylated.

Pharmaceutical agent or drug: A chemical compound or composition capable of inducing a desired therapeutic or prophylactic effect when properly administered to a subject. Pharmaceutical agents include, but are not limited to, chemotherapeutic agents and anti-infective agents.

Pharmaceutically acceptable carriers: The pharmaceutically acceptable carriers useful in the methods and compositions disclosed herein are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide: A polymer in which the monomers are amino acid residues that are joined together through amide bonds. When the amino acids are alpha-amino acids, either the L-optical isomer or the D-optical isomer can be used, the L-isomers being preferred. The terms "polypeptide" or "protein" as used herein are intended to encompass any amino acid sequence and include modified sequences such as glycoproteins. A polypeptide includes both naturally occurring proteins, as well as those that are recombinantly or synthetically produced. A polypeptide has an amino terminal (N-terminal) end and a carboxy-terminal end.

Preventing or treating a disease: "Preventing" a disease refers to inhibiting the full development of a disease, for example in a person who is known to have a predisposition to a disease such as a cancer. An example of a person with a known predisposition is someone with a history of a tumor or an autoimmune disease in the family, or who has been exposed to factors that predispose the subject to a condition, such as a tumor or autoimmune disease. "Treatment" refers to a therapeutic intervention that ameliorates a sign or symptom of a disease or pathological condition after it has begun to develop. In several embodiments, treatment refers to a reduction in size of a tumor, a decrease in the number and/or size of metastases, or a decrease in a symptom of the tumor. In other embodiments, treatment refers to a reduction in an allergic response or inflammation in a subject with an autoimmune disease.

Reducing a sign or symptom of a disease or pathological condition related to a disease, refers to any observable beneficial effect of the treatment. In a non-limiting example, reducing a sign or symptom associated with a tumor (such as pathological angiogenesis) can be evidenced, for example, by a delayed onset of clinical symptoms of the disease in a susceptible subject (such as a subject having a tumor which has not yet metastasized), a reduction in severity of some or all clinical symptoms of the disease, a slower progression of the disease (for example by prolonging the life of a subject having tumor), a reduction in the number of relapses of the disease, an improvement in the overall health or well-being of the subject, or by other parameters well known in the art that are specific to the particular tumor. A "prophylactic" treatment is a treatment administered to a subject who does not exhibit signs of a disease or exhibits only early signs for the purpose of decreasing the risk of developing pathology.

Prime-boost vaccination: An immunotherapy including administration of a first immunogenic composition (the primer vaccine) followed by administration of a second immunogenic composition (the booster vaccine) to a subject to induce an immune response. The primer vaccine and/or the booster vaccine include a vector (such as a viral vector, RNA, or DNA vector) expressing the antigen to which the immune response is directed. The booster vaccine is administered to the subject after the primer vaccine; the skilled artisan will understand a suitable time interval between administration of the primer vaccine and the booster vaccine, and examples of such timeframes are disclosed herein.

In some embodiments, the primer vaccine, the booster vaccine, or both primer vaccine and the booster vaccine additionally include an adjuvant. In other embodiments, the primer vaccine, the booster vaccine, or both primer vaccine and the booster vaccine do not include an adjuvant.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of SpoVM or SpoIVA protein are typically characterized by possession of at least about 75%, for example at least about 80%, 85%, 90%, 91%, 92%, 93%, 94%, 95%, 96%, 97%, 98% or 99% sequence identity counted over the full length alignment with the amino acid sequence of interest. Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

Specific binding: Binding which occurs between such paired species as enzyme/substrate, receptor/agonist, receptor/ligand, antibody/antigen, and lectin/carbohydrate which may be mediated by covalent or non-covalent interactions or a combination of covalent and non-covalent interactions. When the interaction of the two species produces a noncovalently bound complex, the binding that occurs is typically electrostatic, hydrogen-bonding, or the result of lipophilic interactions. Accordingly, "specific binding" occurs between a paired species where there is interaction between the two that produces a bound complex having the characteristics of an antibody/antigen or enzyme/substrate interaction. In particular, the specific binding is characterized by the binding of one member of a pair to a particular species and to no other species within the family of compounds to which the corresponding member of the binding member belongs. Thus, for example, an antibody preferably binds to a single epitope and to no other epitope within the family of proteins. Specific binding can be determined by methods known in the art. With reference to an antibody antigen complex, specific binding of the antigen and antibody has a $K_d$ of less than about $10^{-7}$ Molar (M), such as less than about $10^{-8}$ M, $10^{-9}$ M, $10^{-10}$ M, or even less than about $10^{-11}$ M. A ligand preferably binds to a single cognate receptor and not to receptors for different ligands.

Synthetic: Having a different structure or relationship than found in nature. For example, components of a particle may all occur in nature, but not in the same relationship in the natural environment. For example, a "synthetic" particle core may be made of a naturally occurring material, but it would be synthetic if not found in nature with its surface coated with a lipid bilayer with SpoVM adhered to the lipid bilayer. A synthetic core can also be a non-naturally occurring product, such as a plastic.

Therapeutically effective dose: A dose sufficient to prevent advancement, or to cause regression of a disease, or which is capable of relieving symptoms caused by a disease, such as pain.

Tumor: An abnormal growth of cells, which can be benign or malignant. Cancer is a malignant tumor, which is characterized by abnormal or uncontrolled cell growth. Other features often associated with malignancy include metastasis, interference with the normal functioning of neighboring cells, release of cytokines or other secretory products at abnormal levels and suppression or aggravation of inflammatory or immunological response, invasion of surrounding or distant tissues or organs, such as lymph nodes, etc. "Metastatic disease" refers to cancer cells that have left the original tumor site and migrate to other parts of the body for example via the bloodstream or lymph system.

The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant." Examples of hematological tumors include leukemias, including acute leukemias (such as 11q23-positive acute leukemia, acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer (including basal breast carcinoma, ductal carcinoma and lobular breast carcinoma), lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyngioma, ependymoma, pinealoma, hemangioblastoma, acoustic neuroma, oligodendroglioma, meningioma, melanoma, neuroblastoma and retinoblastoma). In several examples, a tumor is melanoma, lung cancer, lymphoma breast cancer or colon cancer.

Under conditions sufficient for: A phrase that is used to describe any environment that permits a desired activity.

Vaccine: A preparation of attenuated microorganisms (including but not limited to bacteria and viruses), living microorganisms, antigen, or killed microorganisms, administered for the prevention, amelioration or treatment of infectious disease. A vaccine induces an immune response to a particular disease of interest.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. The term "comprises" means "includes." Therefore, comprising "A" or "B" refers to including A, including B, or including both A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Particle Constructs and Methods of Producing Particle Constructs

The particle constructs disclosed herein, that include a lipid bilayer, SpoVM and SpoIVA, can be of any size. These particle constructs are not the naturally occurring spore. In some embodiments, the particle constructs are nanoparticles or microparticles. These terms are used to denote the size of the particles, typically characterized by particle diameter.

A nanoparticle has a diameter in the range of about 1 to less than about 1000 nanometers. In some embodiments, a particle construct has a diameter in the range of about 50 to about 900 nanometers, about 50 to about 800 nanometers, about 50 to about 700 nanometers, about 50 to about 600 nanometers, about 50 to about 500 nanometers, about 50 to about 400 nanometers, about 50 to about 300 nanometers, about 50 to about 250 nanometers, about 50 to about 225 nanometers, about 50 to about 200 nanometers, about 50 to about 150 nanometers, about 50 to about 125 nanometers, about 50 to about 100 nanometers, and/or about 100 to about 200 nanometers. In this context, "about" means within (+/−) 1 nanometer, although not zero nanometers. A microparticle has a diameter in the range of about 1 to less than about 1000 micrometers. In some embodiments, this disclosed particle construct has a diameter in the range of about 1 to about 500 micrometers, about 1 to about 100 micrometers, about 1 to about 50 micrometers, about 1 to about 25 micrometers, about 1 to about 20 micrometers, about 1 to about 15 micrometers, about 1 to about 10 micrometers, about 1 to about 5 micrometers, or about 1 to about 3 micrometers. In this context, "about" means within (+/−) 1 micrometer, although not zero micrometers. In specific non-limiting examples, the particle construct has a diameter of 1 to 5 micrometers, 100 nanometers to 8 micrometers, or about 0.1 to 100 μm.

The particles can be of any shape and are not limited to a perfectly spherical shape. As an example, they may be oval or oblong. Particle size in a composition that includes more than one particle construct can be referred to in terms of average diameter. An "average diameter" refers to the average of at least two diameter measurements of particles within the composition. In some embodiments, the disclosed particle constructs have an average diameter in the range of about 50 to about 900 nanometers, about 50 to about 800 nanometers, about 50 to about 700 nanometers, about 50 to about 600 nanometers, about 50 to about 500 nanometers, about 50 to about 400 nanometers, about 50 to about 300 nanometers, about 50 to about 250 nanometers, about 50 to about 225 nanometers, about 50 to about 200 nanometers, about 50 to about 150 nanometers, about 50 to about 125 nanometers, about 50 to about 100 nanometers, and/or about 100 to about 200 nanometers. In this context, "about" means within (+/−) 1 nanometer, although no zero nanometers. In other embodiments, the disclosed particle constructs have an average diameter of about 1 to about 500 micrometers, about 1 to about 100 micrometers, about 1 to about 50 micrometers, about 1 to about 25 micrometers, about 1 to about 20 micrometers, about 1 to about 15 micrometers, about 1 to about 10 micrometers, about 1 to about 5 micrometers, or about 1 to about 3 micrometers. In this context, "about" means within (+/−) 1 micrometer, although not zero micrometers. In specific non-limiting examples, the particle constructs have an average diameter of 1 to 5 micrometers, 100 nanometers to 8 micrometers, or about 0.1 to 100 μm.

The dimensions of the particles may also be expressed in terms of the longest diameter or cross-section of particles within a composition. In some embodiments, the disclosed particle constructs have an longest diameter in the range of about 50 to about 900 nanometers, about 50 to about 800 nanometers, about 50 to about 700 nanometers, about 50 to about 600 nanometers, about 50 to about 500 nanometers, about 50 to about 400 nanometers, about 50 to about 300 nanometers, about 50 to about 250 nanometers, about 50 to about 225 nanometers, about 50 to about 200 nanometers, about 50 to about 150 nanometers, about 50 to about 125 nanometers, about 50 to about 100 nanometers, and/or about 100 to about 200 nanometers. In this context, "about" means within (+/−) 1 nanometer, although not zero nanometers. In other embodiments, the particle constructs have a longest diameter of about 1 to about 500 micrometers, about 1 to about 100 micrometers, about 1 to about 50 micrometers, about 1 to about 25 micrometers, about 1 to about 20 micrometers, about 1 to about 15 micrometers, about 1 to about 10 micrometers, about 1 to about 5 micrometers, or about 1 to about 3 micrometers. In this context, "about" means within (+/−) 1 micrometer, although not zero micrometers. In specific non-limiting examples, the particle constructs have a longest diameter of 1 to 5 micrometers, 100 nanometers to 8 micrometers, or about 0.1 to 100 μm.

The particles may be isolated, intending that they are physically separated in whole or in part from the environment in which they are synthesized. As an example, particle constructs including a lipid bilayer, SpoVM and SpoIVA can be separated in whole or in part from particles lacking these molecules. As another example, the particle constructs may also be separated from liposomes that do not comprise a synthetic core. Particle constructs including an agent of interest can be separated from particle constructs that do not include the agent of interest. Separation can be based on weight (or mass), density (including buoyant density), size, color and the like (for example, when the particle construct is detectable by its energy emission), etc. Moreover, particle constructs can be separated by size. As an example, nanoparticles may be separated from microparticles, such as, but not limited to, using centrifugation or any size exclusion method.

The particle constructs disclosed herein can be synthesized and stored, for example, in an aqueous buffer at 4° C. The particle constructs also can be frozen for future use, such as, but not limited to, at 0° C., −20° C., or −70° C. The particle constructs can be used or stored at room temperature. The particle constructs may also be stored in a lyophilized form, optionally with a suitable excipient such as sucrose.

As used herein, a particle construct includes a synthetic core with a solid surface with a lipid bilayer coat. The synthetic core can be solid, but need not be solid. The core can have a void volume and/or an aqueous fluid environment at their center.

The synthetic core can be made from biodegradable polymers that are non-naturally occurring. Exemplary synthetic polymers which can be used to form the particle core include without limitation aliphatic polyesters, poly (lactic acid) (PLA), poly (glycolic acid) (PGA), copolymers of lactic acid and glycolic acid (PLGA), poly(ε-caprolactone (PCL), polyanhydrides, poly(ortho)esters, polyurethanes, poly(butyric acid), poly(valeric acid), and poly(lactide-co-caprolactone). In specific non-limiting examples, the synthetic core is biodegradable polymer is poly (D, L-lactide-co-glycolide) (PLGA), poly(ε-caprolactone) (PCL), or poly (lactic acid) (PLA). In some embodiments, the polymer is PLGA.

In additional embodiments, the synthetic core can be produced from alginate and other polysaccharides including dextran and cellulose, collagen, chemical derivatives thereof, including substitutions, additions of chemical groups such as for example alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

The synthetic core can be a non-naturally occurring material, such as a plastic resin. Suitable plastic resins include, but are not limited to, polystyrene, polypropylene, or polyethylene. The synthetic core can also be a metal. Suitable metals include, but are not limited to, magnetic iron, gold or silver. The synthetic core can be a silica bead, such as a mesoporous silica bead, such as MCM-41 or SBA-15. Mesoporous silica nanoparticles are synthesized by reacting tetraethyl orthosilicate with a template made of micellar rods. The result is a collection of nano-sized spheres or rods that are filled with a regular arrangement of pores. The template can then be removed by washing with a solvent adjusted to the proper pH. Mesoporous silica particles can also be synthesized using a sol-gel methods or spray drying. 3-Mercaptopropyl)trimethoxysilane can also be used to synthesize mesoporous silica.

Figure 5:
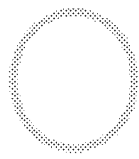
FIG. 5. Schematic diagram of the production of SSHEL particles.

The synthetic core is coated with a lipid bilayer on its outer solid surface, see, for example, FIG. 5. This bilayer may be comprised of one or more lipids of the same or different type. A variety of lipid bilayers can be used, providing the components are able to form stable bilayers on the synthetic core. The lipids may be isolated from a naturally occurring source or they may be synthesized apart from any naturally occurring source. Solid supports can readily be coated with lipid bilayer, see for example, U.S. Published Patent Application No. 2011/0229556, which is incorporated by reference herein.

In some embodiments, at least one (or some) of the lipids is/are amphipathic lipids, defined as having a hydrophilic and a hydrophobic portion (typically a hydrophilic head and a hydrophobic tail). The hydrophobic portion typically orients into a hydrophobic phase (e.g., within the bilayer), while the hydrophilic portion typically orients toward the aqueous phase (e.g., outside the bilayer, and possibly between adjacent apposed bilayer surfaces). The hydrophilic portion may comprise polar or charged groups such as carbohydrates, phosphate, carboxylic, sulfato, amino, sulfhydryl, nitro, hydroxy and other like groups. The hydrophobic portion may comprise apolar groups that include without limitation long chain saturated and unsaturated aliphatic hydrocarbon groups and groups substituted by one or more aromatic, cyclo-aliphatic or heterocyclic group(s). Examples of amphipathic compounds include, but are not limited to, phospholipids, aminolipids and sphingolipids.

In a specific non-limiting example, the lipids are phospholipids. Phospholipids include, without limitation, phosphocholines, phosphoglycerols, phosphoethanolamines and phosphoinositols. Exemplary phospholipids are phosphatidylcholine, phosphatidylethanolamine, phosphatidylglycerol, phosphatidylinositol, phosphatidylserine, and the like. Other non-limiting examples are dimyristoylphosphatidylcholine (DMPC), dioleoylphosphatidylcholine (DOPC), and dioleoylphosphatidylserine (DSPC). The type, number and ratio of lipids may vary. Other lipid membrane components, such as cholesterol, sphingomyelin, cardiolipin, can also be included in the lipid bilayer.

The lipid bilayer can include lipids that are anionic and neutral (including zwitterionic and polar) lipids including anionic and neutral phospholipids. Neutral lipids exist in an uncharged or neutral zwitterionic form at a selected pH. At physiological pH, such lipids include, for example, dioleoyl-phosphatidylglycerol (DOPG), diacylphosphatidylcholine, diacylphosphatidylethanolamine, ceramide, sphingomyelin, cephalin, cholesterol, cerebrosides and diacylglycerols. Examples of zwitterionic lipids include without limitation dioleoylphosphatidylcholine (DOPC), dimyristoylphosphatidylcholine (DMPC), and dioleoylphosphatidylserine (DOPS). An anionic lipid is a lipid that is negatively charged at physiological pH. Non-limiting examples are phosphatidylglycerol, cardiolipin, diacylphosphatidylserine, diacylphosphatidic acid, N-dodecanoyl phosphatidylethanolamines, N-succinyl phosphatidylethanolamines, N-glutarylphosphatidylethanolamines, lysylphosphatidylglycerols, palmitoyloleyolphosphatidylglycerol (POPG), and other anionic modifying groups joined to neutral lipids.

Collectively, anionic and neutral lipids are non-cationic lipids. Such lipids may contain phosphorus but they are not so limited. Examples of non-cationic lipids of use include lecithin, lysolecithin, phosphatidylethanolamine, lysophosphatidylethanolamine, dioleoylphosphatidylethanolamine (DOPE), dipalmitoyl phosphatidyl ethanolamine (DPPE), dimyristoylphosphoethanolamine (DMPE), distearoyl-phosphatidyl-ethanolamine (DSPE), palmitoyloleoyl-phosphatidylethanolamine (POPE) palmitoyloleoylphosphatidylcholine (POPC), egg phosphatidylcholine (EPC), distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), palmitoyloleyolphosphatidylglycerol (POPG), 16-O-monomethyl PE, 16-O-dimethyl PE, 18-1-trans PE, palmitoyloleoyl-phosphatidylethanolamine (POPE), 1-stearoyl-2-oleoyl-phosphatidyethanolamine (SOPE), phosphatidylserine, phosphatidylinositol, sphingomyelin, cephalin, cardiolipin, phosphatidic acid, cerebrosides, dicetylphosphate, and cholesterol.

Additional nonphosphorous containing lipids of use include stearylamine, dodecylamine, hexadecylamine, acetyl palmitate, glycerolricinoleate, hexadecyl stereate, isopropyl myristate, amphoteric acrylic polymers, triethanolamine-lauryl sulfate, alkyl-aryl sulfate polyethyloxylated fatty acid amides, dioctadecyldimethyl ammonium bromide and the like, diacylphosphatidylcholine, diacylphosphatidylethanolamine, ceramide, sphingomyelin, cephalin, and cerebrosides. Lipids such as lysophosphatidylcholine and lysophosphatidylethanolamine may be used in some instances. Noncationic lipids also include polyethylene glycol-based polymers such as PEG 2000, PEG 5000 and polyethylene glycol conjugated to phospholipids or to ceramides (referred to as PEG-Cer).

The lipids can be biodegradable. Biodegradable lipids include but are not limited to 1,2-dioleoyl-sn-glycero-3-phosphocholine (dioleoyl-phosphocholine, DOPC), anionic 1,2-di-(9Z-octadecenoyl)-sn-glycero-3-phospho-(1'-rac-glycerol) (dioleoyl-phosphoglycerol, DOPG), and 1,2-distearoyl-sn-glycero-3-phosphoethanolamine (distearoyl-phosphoethanolamine, DSPE). Non-lipid membrane components such as cholesterol may also be incorporated.

In the disclosed particle constructs, SpoVM is adhered to the lipid bilayer of the particle construct, and SpoVA is adsorbed to the SpoVM.

In some embodiments, the lipid bilayer is about 90%, 91%, 92%, 93%, 94%, 95%, 96%, 97%, 98%, 99% or 100% saturated with SpoVM. In some embodiments, SpoVM comprises an amino acid sequence at least 90% identical to the amino acid sequence set forth as SEQ ID NO: 2, and wherein the SpoVM specifically binds SpoIVA. Exemplary amino acid sequences for SpoVM and SpoIVA are provided below:

(SEQ ID NO: 1)

```
MCGSSHHHHHHSSGLVPRGSHMASMEKVDIFKDIAERTGGDIYLGVVGAV
RTGKSTFIKKFMELVVLPNISNEADRARAQDELPQSAAGKTIMTTEPKFV
PNQAMSVHVSDGLDVNIRLVDSVGYTVPGAKGYEDENGPRMINTPWYEEP
IPFHEAAEIGTRKVIQEHSTIGVVITTDGTIGDIARSDYIEAEERVIEEL
KEVGKPFIMVINSVRPYHPETEAMRQDLSEKYDIPVLAMSVESMRESDVL
SVLREALYEFPVLEVNVNLPSWVMVLKENHWLRESYQESVKETVKDIKRL
RDVDRVVGQFSEFEFIESAGLAGIELGQGVAEIDLYAPDHLYDQILKEVV
GVEIRGRDHLLELMQDFAHAKTEYDQVSDALKMVKQTGYGIAAPALADMS
```

LDEPEIIRQGSRFGVRLKAVAPSIHMIKVDVESEFAPIIGTEKQSEELVR

YLMQDFEDDPLSIWNSDIFGRSLSSIVREGIQAKLSLMPENARYKLKETL

ERIINEGSGGLIAIIL
(SpoIVA$^{C98S}$, including C98S (underlined and bold) and a cysteine as the second residue (underlined and bold), N-terminal residues are underlined and can be modified, see below.)

(SpoVM, SEQ ID NO: 2)
MKFYTIKLPKFLGGIVRAMLGSFRKD

In some embodiments, the N-terminal methionine (M) is removed. In other embodiments, the initial methionine (M) is maintained.

In additional embodiments, the SpoVM comprises an amino acid sequence at least 91%, 92%, 93%, 94%, 95%, 96%, 97%, 98%, or 99% identical to SEQ ID NO: 2. In other embodiments, SpoVM comprises or consists of the amino acid sequence set forth as SEQ ID NO: 2, or the amino acid sequence set forth as SEQ ID NO: 2 with the N-terminal methionine removed. In further embodiments, the SpoVM comprises or consists of the amino acid sequence set forth as SEQ ID NO: 2, with at most 1, 2, 3, 4, or 5 conservative amino acid substitutions. In yet other embodiments, the SpoVM comprises or consists of one of the following amino acid sequences.

```
Bacillus amyloliquefaciens
                                          (SEQ ID NO: 3)
MKFYTIKLPKFLGGIVRAMLGSFRKE Bacillus fordii
                                          (SEQ ID NO: 4)
MKFYTIKLPRFLGGIVRAMLGTFKKD Geobacillus stearothermophilus
                                          (SEQ ID NO: 5)
MKFYTIKLPKFLGGIVRAMLNTFKK Tuberibacillus calidus
                                          (SEQ ID NO: 6)
MKFYTIKLPRFLGGFIRAILGSFKK Thalassobacillus devorans
                                          (SEQ ID NO: 7)
MKFYTIKLPKFIGGFVRAVIGTFKK Paenibacillus pinihumi
                                          (SEQ ID NO: 8)
MKFYTIKLPKFLGGFVKAVLNTFQKN Clostridium perfringens
                                          (SEQ ID NO: 9)
MRIMTIKLPKFLAKIVRMFKGNKKSD Clostridium acetobutylicum
                                          (SEQ ID NO: 10)
MKIVAIKLPKFLSNIIKFFFRKKS Clostridium botulinum
                                          (SEQ ID NO: 11)
MKIVAIKLPKFLSNIIKFFFRKKS
```

In some embodiments, the N-terminal methionine (M) is removed. In other embodiments, the initial M is maintained.

In additional embodiments, the SpoVM comprises or consists of an amino acid sequence at least 91%, 92%, 93%, 94%, 95%, 96%, 97%, 98%, or 99% identical to one of SEQ ID NOs: 3-11. In other embodiments, SpoVM comprises or consists of the amino acid sequence set forth as one of SEQ ID NOs: 3-11, or the amino acid sequence set forth as SEQ ID NOs: 3-11 with the N-terminal methionine removed. In further embodiments, the SpoVM comprises or consists of the amino acid sequence set forth as one of SEQ ID NOs: 3-11, with at most 1, 2, 3, 4, or 5 conservative amino acid substitutions.

SpoIVA is adhered to the SpoVM, such that it is stably associated with SpoVM. In some embodiments, SpoIVA is adhered to the SpoVM so that the particle is uniformly coated with SpoIVA. In other embodiments, the lipid bilayer is encases with SpoVM, such as 90%, 91%, 92%, 93%, 94%, 95%, 96%, 97%, 98%, 99% or 100% encased with SpoVM.

In some embodiments, SpoIVA is adhered to the SpoVM on the particle in the presence of ATP, in order to ensure the SpoIVA stably associates with the SpoVM. In additional embodiments, the SpoIVA comprises a cysteine that is exposed at a surface of the particle. In specific non-limiting examples, the SpoIVA comprises a cysteine at the N-terminus, as the second residue following the N-terminal methionine, or within 20 amino acids of the N-terminus, such as within 19, 18, 17, 16, 15, 14, 13, 12, 11, 10, 9, 8, 7, 6, 5, 4, 3, 2 or at the N-terminus, wherein the cysteine is exposed at a surface of the particle. In other specific non-limiting examples, the SpoIVA comprises a cysteine at the N-terminus, as the second residue following the N-terminal methionine, or within 10 amino acids of the N-terminus. In additional embodiments, the SpoIVA is at least 90% identical to the amino acid sequence set forth as SEQ ID NO: 1, wherein the SpoIVA comprises a cysteine at the N-terminus or within 20 amino acids of the N-terminus, such as within 19, 18, 17, 16, 15, 14, 13, 12, 11, 10, 9, 8, 7, 6, 5, 4, 3, 2 or at the N-terminus, wherein the cysteine is exposed at a surface of the particle. In other specific non-limiting examples, the SpoIVA comprises a cysteine at the N-terminus, as the second residue following the N-terminal methionine, or within 10 amino acids of the N-terminus. In specific non-limiting examples, SpoIVA comprises or consists of the amino acid sequence set forth as SEQ ID NO: 1. In other specific non-limiting examples, SpoIVA comprises or consists of the amino acid sequence set forth as SEQ ID NO: 1, with the N-terminal amino acid removed. Additional exemplary SpoVA amino acid sequences of use include:

```
B. subtilis
                                          (SEQ ID NO: 12)
MEKVDIFKDIAERTGGDIYLGVVGAVRTGKSTFIKKFMELVVLPNISNEADRARAQDELP

QSAAGKTIMTTEPKFVPNQAMSVHVSDGLDVNIRLVDCVGYTVPGAKGYEDENGPRMINT

PWYEEPIPFHEAAEIGTRKVIQEHSTIGVVITTDGTIGDIARSDYIEAEERVIEELKEVG

KPFIMVINSVRPYHPETEAMRQDLSEKYDIPVLAMSVESMRESDVLSVLREALYEFPVLE

VNVNLPSWVMVLKENHWLRESYQESVKETVKDIKRLRDVDRVVGQFSEFEFIESAGLAGI

ELGQGVAEIDLYAPDHLYDQILKEVVGVEIRGRDHLLELMQDFAHAKTEYDQVSDALKMV
```

-continued

KQTGYGIAAPALADMSLDEPEIIRQGSRFGVRLKAVAPSIHMIKVDVESEFAPIIGTEKQ

SEELVRYLMQDFEDDPLSIWNSDIFGRSLSSIVREGIQAKLSLMPENARYKLKETLERII

NEGSGCLIAIIL

*B. amyloliquefaciens* (SEQ ID NO: 13)
MIRIGSPGGDHLEKVDIFKDIAERTGGDIYLGVVGAVRTGKSTF

IKKFMELVVLPNISNEADRARAQDELPQSAAGKTIMTTEPKFVPNQAMSVHVAEGLDV

NIRLVDCVGYTVPGAKGYEDENGPRMINTPWYEEPIPFHEAAEIGTRKVIQEHSTIGV

VITTDGSIGDIARGDYVEAEERVIDELKEVGKPFIMVINSVKPYHPETEALRAELSAK

YDIPVLAMSVESMRETDVLSVLREALYEFPVLEVNVNLPSWVMVLKENHWLRESYQES

VKETVKDIKRLRDVDRVVGHFSEFEFIESAGLAGIELGQGVAEIDLYAPDHLYDQILK

EVVGVEIRCKDHLLELMQDFAHAKKEYDQVSDALKMVKQTCYGIAAPALADMSLDEPE

IIRQGSRFGVRLKAVAPSIHMIKVDVESEFAPIIGTEKQSEELVRYLMQDFEDDPLSI

WNSDIFGRSLSSIVREGISAKLSLMPENARYKLKETLERIINEGSGGLIAIIL

*B. licheniformis* (SEQ ID NO: 14)
MEKVDIFKDIAERTGGDIYLGVVGAVRTGKSTFIKKFMELVVLP

NINNEADRARAQDELPQSAAGKTIMTTEPKFVPNQAMSVHVSDGLDVNIRLVDCVGYT

VPGAKCYEDENGPRMINTPWYEEPIPFHEAAEIGTRKVIQEHSTIGVVITTDGTIGEI

ARQDYVEAEERVIDELKEVGKPFIMVINSVRPYHPETEALRQELMEKYDIPVLAMSVE

SMREADVLSVLREALYEFPVLEVNVNLPSWVMVLKENHWLRENYQDSVKETVKDIKRL

RDVDRVVGHFSEFDFIERASLAGIEMGQGIAEIDLYAPDYLYDEILREVVGVEIRGKD

HLLQLMQDFAHAKTEYDQVSDALKMVKQTGYGIAAPALTDMSLDEPEIIRQGSRFGVR

LKAVAPSIHMIKVDVESEFAPIIGTEKQSEELVRYLMQDFEDDPLSIWNSDIFGRSLS

SIVREGIQAKLSLMPENARYKLKETLERIINEGSCGLIAIIL

*B. anthracis* (SEQ ID NO: 15)
MEKVDIFKDIAERTGGDIYFGVVGAVRTGKSTFIKKFMELVVIP

NIENESDRQRAQDELPQSAAGRTIMTTEPKFVPNQAVSIEVDEGLEVNIRLVDCVGYT

VPGAKGYEDENGPRMINTPWYEEPIPFHEAAEIGTRKVIQEHSTIGVVITTDGTIGEI

PRRDYIEAEERVVNELKEVGKPFIMIINTVQPYHPDTEQLRQSLSEEYDIPVIAMSVE

SLRETDVYNVLREALFEFPVLEVNVNLPSWVMVLNEGHWLRQSYQEAVQETVKDIKRL

RDVDRVVWQFSQYEFIDRASLAGIDMGQGVAEIDLYAPDELYDQILKEVVGVEIRGKD

HLLKLMLDLSHAKIEYDQVADALRMVKQTGYGVAAPALADMSLDEPEIIRHGSRFGVK

LKAVAPSIHMIKVDVESTFEPIIGTEKQSEELVRYLMQDFEDDPLSIWNSDIFGRSLS

SIVREGIQAKLSLMPENARYKLKETLERIINEGSGGLIAIIL

*B. pumilus* (SEQ ID NO: 16)
MEKVDIFKDIAERTGGDIYLGVVGAVRTGKSTFIKKFMELVVLP

NINNEADRARAQDELPQSAAGKTIMTTEPKFVPNQAASIHVSDGLDVNIRLVDCVGYT

VPGARGYEDENGPRMINTPWYEEPIPFHEAAEIGTRKVIQEHSTIGVVITTDGSIGEI

PRHDYIESEERVIDELKEVGKPFIMVINSVRPYHPETEALRQELSQKYDIPVLAMSVE

SMREQDVLSVLREALYEFPVLEVNVNLPSWVMVLKEDHWLRESYQDSVKETVKDIKRL

RDVDRVVGQFSEFDFIERAGLAGIEMGQGIAEIDLYAPDDLYDHILKEVVGVEIRGKD

```
HLLELMQDFAHAKTEYDQVSDALKMVKQTGYGIAAPALSDMSLDEPEIIRQGSRFGVR

LKAVAPSIHMIKVDVESEFAPIIGTEKQSEELVRYLMQDFEDDPLSIWNSDIFGRSLS

SLVREGIQAKLSLMPENARYKLKETLERIINEGSGGLIAIIL
```

C. botulinum (SEQ ID NO: 17)
```
MENFNIYKDIAERTQGDIYVGVVGPVRTGKSTFIKKFMEKMVIP

KIENSYKKQRAKDELPQSSSGKAIHTTEPKFVPNEAVEVSLENDTKFKVRMVDCVGYI

VNGALGYMEEEDKPKMVTTPWYDYEIPFEEAAEIGTKKVINEHSTIGLLITTDGSITD

IDRENYVEVEERVVEELKSINKPFIIVLNSSHPYEPETIELRKNLEEEYDVPVQTMDI

LNMKEEDMTNVFQRVLKEFPIKEVNIDMPAWIEELKPEHWLKTDFINVVKNMAKEIYK

VRDIKKSMENLYEFEFLDNSTLNEMNMGEGTARIALRPKDGLFYKIIGEVCNREIENE

NDLLKIVETMNKAKIEYDRIAEALEDVKETGYGLVAPQLTEMKLEEPEIVKQGSRYGV

KLKASAPSLHFIRADIETEVSPIMGTEKESEEMLKSLLEEFETDPSKIWQSNMFGKSL

EVLVKEGLQNKLYRMPEDVQVKIQKTLQKIINEGNGGLICIIL
```

C. perfringens (SEQ ID NO: 18)
```
MEDFNIYKDIAERTQGDIYVGVVGPVRTGKSTFIKRFMDLMVIP

KIDNAYKKERAKDELPQSGSCKTIHTTEPKFVPNEAVEIALDDGIKFSVRMVDCVGYI

VKGANGYFDDGESKKVHTPWFDYEIPFEDAAEIGTRKVITDHSTIGLVVTTDGSITGI

DRDDYLDAEERVVAELKSIDKPFIIVLNSLDPRAEETLDLKQELEIRYGVPVQIMDVA

NMNENDINDLFTKVLKEFPVKEINIDMPKWIEKLEPSHWLKSNFIDIVKDMCKNISKI

RDVKDLLSTYGEDFLGVADISEMNLGDGTVRVKMTPKNGIFYKIISEMCDEELNDESD

LIALIKDLHKAKSEYDKVAEAINSVKETGYGLVAPQLSEMKFEKPDIDKQGSKYVVKL

KASAPSLHLIKADIQTEICPIMGTEKETQEVFKTLLEQFESDPEKLWQSNMFGKSLET

LVQEGLRSKLYKMPDDIQSKIQKTLQRIINEGEGNLICIIF
```

O. iheyensis (SEQ ID NO: 19)
```
MEKTDIFKDISKRTNGDIYLGIVGAVRTGKSTFIKKFMELVVLP

NIESESDRARAHDELPQSAAGKTIMTTEPKFIPNQAVQVKVDDGLDVNVRLVDCVGYA

VEGAKGFEDENGPRMIHTPWYEDPIPFHDAAEIGTRKVIQEHSTIGVVVTTDGSIGEI

ERHDYEDAETRVVEELKEVGKPFIMVINSTQPRSQETELLRQELVEKHDIPVLAMSIE

SMTEHDVYNVLREALFEFPVLEVNVNLPSWVMVLNERHWLRQNYQDAIQTTVKDIKRL

RDVDHIVGNFTDYDYIEQASLAGMEMGEGIAEIDLHAPDYLYDEVLKEIVGEEIRGKD

HLLELMQDFAYAKREYDQVAGALQMVKQTGYGIAAPTLEDMQLDEPEIIRQGSRFGVR

LKAVAPSIHMIRVEVESEFAPIIGTEKQSEELVRYLMQDFEEDPLSIWESDIFGRSLS

SIVREGIQAKISLMPENARYKLKDTLERIINEGSGGLIAIIL
```

Symbiobacterium thermophilum (SEQ ID NO: 20)
```
MERIDIFEDVARRTGGDIYIGVVGPVRTGKSTFIRRLAEQVILP

NIEDEYLQARIRDELPQSGNGRTIMTVEPKFVPDEAVEITLREGLTVRVRLVDSVGYA

VEGALGYMQEDGSPRMVRTPWFEEEIPFHDAAEIGTRKVIAEHSTIGLLVTTDGTITD

LARGKYLEAEERVVSELQALGKPFVIVLNTTRPYAQETMELAGELEVKYNAPVIPVDA

SELTQDDIHLILEQALFEFPVREANIALPRWVEELDSAHPVRAQFEEAIAEALQGIQK

IRDVDAAVERLSSYEFMAAVNLQSIDMGAGVAHVQTEARDDLYYQVLEEITGVPLEGK

HTMVRLLREYTQAKREYDKIKDALEDVKATGYGVVTPAIEDITFEEPELVRQGIMYGV
```

-continued

KLQATAPSLHFIRADISAEVTPIIGTAKQGEELVQYLLERFEDDPRQLWEFDIFGKSL

HELVQEGIKAKLHRMPEDAQVKLQETLSRIINEGSGGLICIII

*B. cereus*
(SEQ ID NO: 21)

MEKVDIFKDIAERTGGDIYFGVVGAVRTGKSTFIKKFMELVVIPNIENESDRQRAQDELP

QSAAGRTIMTTEPKFVPNQAVSIEVDEGLEVNIRLVDCVGYTVPGAKGYEDENGPRMINT

PWYEEPIPFHEAAEIGTRKVIQEHSTIGVVITTDGTIGEIPRRDYIEAEERVVNELKEVG

KPFIMIINTVQPYHPDTEQLRQSLSEEYDIPVIAMSVESLRETDVYNVLREALFEFPVLE

VNVNLPSWVMVLNEGHWLRQSYQEAVQETVKDIKRLRDVDRVVWQFSQYEFIDRASLAGI

DMGQGVAEIDLYAPDELYDQILKEVVGVEIRGKDHLLKLMLDLSHAKIEYDQVADALRMV

KQTGYGVAAPALADMSLDEPEIIRHGSRFGVKLKAVAPSIHMIKVDVESTFEPIIGTEKQ

SEELVRYLMQDFEDDPLSIWNSDIFGRSLSSIVREGIQAKLSLMPENARYKLKETLERII

NEGSGGLIAIIL

*B. halodurans*

(SEQ ID NO: 22)

MEKIDIFKDIAERTGGDIYLGVVGAVRTGKSTFIKKFMELVVLPNIENEADKARAQDELP

QSAAGKTIMTTEPKFVPNQAVSIHVDEGLDVNVRLVDCVGYAVPGAKGYEDENGPRMINT

PWYEEPIPFQEAAEIGTRKVIQEHSTLGVVITTDGSIGEIPRYDYIESETRVIEELKEVG

KPFIIVINSVRPHHPETEQLRRDLQEEHDIPVLAMSIESMGEQDINNVLREVLFEFPVHE

VNVNLPSWVMVLKEEHWLRQNYEQSVRDTVQDIKRLRDVDRVVGHFAEYEFIDDARLAGI

EMGQGIAEIDLYAPDDLYDQILKEVVGVEIRGKDHLLHLMQEFAHAKSEYDQVADALRMV

KQTGYGIAAPALSDMSLDEPEIIRQGSRFGVRLKAVAPSIHMIKVDVESEFAPIIGTEKQ

SEELVRYLMQDFEENPLSIWNSDIFGRSLNSIVREGISAKLSLMPENARYKLKETLERII

NEGSGGLIAIIL

*B. thuringiensis*

(SEQ ID NO: 23)

MEKVDIFKDIAERTGGDIYFGVVGAVRTGKSTFIKKFMELVVIPNIENESDRQRAQDELP

QSAAGRTIMTTEPKFVPNQAVSIEVDEGLEVNIRLVDCVGYTVPGAKGYEDENGPRMINT

PWYEEPIPFHEAAEIGTRKVIQEHSTIGVVITTDGTIGEIPRRDYIEAEERVVNELKEVG

KPFIMIINTVQPYHPDTEQLRQSLSEEYDIPVIAMSVESLRETDVYNVLREALFEFPVLE

VNVNLPSWVMVLNEGHWLRQSYQEAVQETVKDIKRLRDVDRVVWQFSQYEFIDRASLAGI

DMGQGVAEIDLYAPDELYDQILKEVVGVEIRGKDHLLKLMLDLSHAKIEYDQVADALRMV

KQTGYGVAAPALADMSLDEPEIIRHGSRFGVKLKAVAPSIHMIKVDVESTFEPIIGTEKQ

SEELVRYLMQDFEDDPLSIWNSDIFGRSLSSIVREGIQAKLSLMPENARYKLKETLERII

NEGSGGLIAIIL

*Carboxydibrachium pacificum*

(SEQ ID NO: 24)

MEGYDIYRDIAERTQGDIYIGVVGPVRTGKSTFIKRFMDILVLPNLEEAPLKERIRDELP

QSAAGKTVMTTEPKFVPEKAVEITINENTKFKVRLVDCVGYMVKGALGYMEGDKPRMVST

PWYDYEIPFEEAAEIGTRKVISDHSTIGLVVTIDGSITEIPRENYVPAEERVIKELKELN

KPFIILLNTTHPQNTETMNLASELEKKYDTPVIVVNVMQMEIKDIYKILEKVLFEFPIRE

IAIDLPTWVDALDKNHWFKENVLSTVKESVKDLYRLRDISNLVGGLKANENFSEVFIKKI

APGEGSANIEIKTHEGLFFKILSDESGLTIKNDKELMSVIKELAHAKRQYDRIKEAFLKA

QETGVGVVPASLEEMKFEKPEIVRQGGRFAVRLKASAPSYHIFRTDITAEVTPVVGTEKQ

```
SEDFVKYITEQFENAPEKIWESNIFGKTLSDLVKEGMQNKVSAIPENLSHKLRDTLEKVV

NDSGGGIIFIII
```

Geobacillus kaustophilus
(SEQ ID NO: 25)
```
MEKVDIFKDIAERTGGDIYLGVVGAVRTGKSTFIKRFMELVVIPNIKNEADKARAQDELP

QSAAGKTIMTTEPKFVPNQAVTVKVDEGLEVNIRLVDCVGYAVPGAKGYEDENGPRMIHT

PWYEEPIPFQEAAEIGTRKVIQEHSTIGVVITTDGTIGEIPRQDYVEAEERVISELKEVG

KPFIMIVNTVRPHHPETEALRRELAEKYDIPVLAMSVESMREADVYNVLREALYEFPVLE

VNVNLPSWVMVLREDHWLRESYQEAVRDTVKDIKRLRDVDRVVQQFAEYDFIEKAALAGI

EMGQGIAEIDLYAPDELYDQILKEIVGVEIRGKDHLLQLMQDFAHAKAEYDQIADALKMV

KQTGYGIAAPALSDMSLDEPEIIRQGSREGVRLKAVAPSIHMIKVDVESEFAPIIGTEKQ

SEELVRYLMQDFEDDPLSIWNSDIFGRSLSSIVREGIQAKLALMPENARYKLKETLERII

NEGSGGLIAIIL
```

Anoxybacillus flavithermus
(SEQ ID NO: 26)
```
MHIVSSYVLNIREGRQLEKVDLFKDIAERIGGDIYLGVVGAVRTGKSTFIKKFMELVVIP

NIQNEADKARAQDELPQSAAGKTIMTTEPKFVPNQAVKVKVDDGLEVNIRLVDCVGYTVQ

GAKGFEDENGPRMIHTPWYEEPIPFQEAAEIGTRKVIQEHSTIGVVITTDGSIGEIPREN

YVEAEERVVNELKEVGKPFIMIINTVRPQHPETETLKQQLSEKYDIPVLALSVEGMREAD

VYQVLREALYEFPVLEVNVNLPNWVMVLRENHWLRESYQDAVRDTVKDIKRLRDVDRVVQ

QFSEYDFIDEARLAGIEMGQGIAEIDLYAPDELYDQILKEVVGVEIRGKDHLLQLMQDFA

YAKAEYDQIADALRMVKQTGYGIAAPSLSDMSLDEPEIIRQGSRFGVRLKAVAPSIHMIK

VDVESEFAPIIGTEKQSEELVRYLMQDFEDDPLSIWNSDIFGRSLSSIVREGIQAKLALM

PENARYKLKETLERIINEGSGGLIAIIL
```

Heliobacterium modesticaldum
(SEQ ID NO: 27)
```
MEKLDIFRDISDRTGGDIYIGVVGPVRTGKSTFIKRFMEHLVLPNIKNIHDKERARDELP

QSGAGRTIMTTEPKFIPNEAVEIGVKNGLKMRIRMVDCVGYTVDGALGYEEEEGPRMVMT

PWAEAEMPFQDAAEIGTRKVIADHSTIGLVVTTDGSITDLPRESYVEAEERVIEELRELH

KPFVVILNSMRPHSRETAELAYTLESQYQVPVLPLNVSELNQDDILKLLEEALFEFPVTE

VNVNLPLWIEELDVKHPLRQKFESAVRETISQVKRLRDIDIAVETLGEYDFVEEVFLQQM

NLGTGSASIEMTAPDSMFYTVLQEESGFTITGEHDLLRLMKELSKAKREYDKVSTALEDV

RQNGYGVVNPSLEEMYLEEPELIKQGNREGVKLKASAPSLHIIRADITTEITPIIGTEKQ

CEELVRYILEEFEENPQKIWESNIFGKSLHDLVREGVQNKLQRMPENVQGKLQETLQRIV

NEGNGGLICIII
```

Clostridium acetobutylicum
(SEQ ID NO: 28)
```
MENFNIYKDIAERTDGDIYVGVVGPVRTGKSTFIKRFMDTMVIPNIDNPHKKERAKDELP

QSSSGKTIHTTEPKFVPNEAVDISLSEGIKLKVRLVDCVGYIVKSALGYAEADKPKMVST

PWFDHEIPFEKAAEIGTKKVIDEHSTIGLVVTTDGSITGIPREDYVEAEERVVKELKEIK

KPFVIILNSSQVDDPKTIELRDELEKKYDVSVQVLDVQNMVEEDIIKVFSKILREFPVRE

INIDMPEWIEKLSTKHWLKDNFMNIIKEICIKVNKVRDISKIVASYSGMDYLDKADMTEM

DMGSGVGRIVFTPKRDMFYKVLSEECECDIDGENKLLSIMKEMHEAKVQYDRISEALKDV
```

-continued

```
REKGYGLVAPQLTEMKLEEPKIVKSGARYEVKLKASAPSFHFIRADIETEVSPIMGSERE

SEELVRSLLEQFENDPSEIWESNMFGKSLEVLVKEGLQKKLYKMPDDVQAKIQKTLEKII

NEGNGGLICIIL
```

The SpoIVA can comprise the amino acid sequence set forth as any one of SEQ ID NOs: 13-28, modified to include a cysteine at the N-terminus or within 20 amino acids of the N-terminus, such as within 19, 18, 17, 16, 15, 14, 13, 12, 11, 10, 9, 8, 7, 6, 5, 4, 3, 2 amino acids of the N-terminus, wherein the cysteine is exposed at a surface of the particle. In other specific non-limiting examples, the SpoIVA comprises a cysteine at the N-terminus, as the second residue following the N-terminal methionine, or within 10 amino acids of the N-terminus.

In additional embodiments, the SpoIVA comprises an amino acid sequence at least 91%, 92%, 93%, 94%, 95%, 96%, 97%, 98%, or 99% identical to one of SEQ ID NOs: 13-28. In other embodiments, SpoIVA comprises or consists of the amino acid sequence set forth as one of SEQ ID NOs: 13-28. In yet other embodiments, the SpoIVA comprises or consists of the amino acid sequence set forth as one of SEQ ID NOs: 13-28 with the N-terminal methionine removed. In further embodiments, the SpoIVA comprises the amino acid sequence set forth as one of SEQ ID NOs: 13-28, with at most 1, 2, 3, 4, or 5 conservative amino acid substitutions.

The SpoIVA and SpoM utilized in the particle construct can be from the same or different bacteria. In some embodiments, the SpoIVA and SpoVM are both from *B. subtilis*. In other embodiments, any of the SpoIVA and SpoVM proteins listed above can be used in any combination, provided the SpoIVA will adsorb to the SpoVM.

In some embodiments, the lipid bilayer including SpoVM is contacted with SpoIVA in appropriate reaction conditions such that the SpoIVA will adsorb to the SpoVM. In specific non-limiting examples, the SpoVM is at least 90%, 91%, 92%, 93%, 94%, 95%, 96%, 97%, 98%, 99% or 100% saturated with SpoIVA. In other non-limiting examples, the ratio of SpoVM to SpoIVA is from about 1.5:1 to about 1:1.5, or from about 1.1:1 to about 1:1.1, such as about 1:1. In specific, non-limiting examples, the reaction medium include adenosine tri-phosphate (ATP). The concentration of ATP is sufficient such that that SpoVA forms protrusions on the surface of the particle. Suitable concentrations of ATP include, but are not limited to, about 1 mM to about 20 mM ATP, such as about 2 mM to about 10 mM ATP, such as about 3 mM to about 5 mM ATP, for example, about 4 mM ATP. The reaction can also include MgCl$_2$, for example about 1 to about 30 mM MgCl$_2$, such as about 5 to about 20 mM MgCl$_2$, for example 7 to about 15 mM MgCl$_2$, or about 9 to about 11 mM MgCl$_2$, such as about 10 mM MgCl$_2$.

In yet other embodiments, the concentration of NaCl is about 100 mM to about 500 mM NaCl, such as about 250 mM to about 450 mM NaCl, such as about 350 mM to about 400 mM NaCl, for example about 400 mM NaCl. An exemplary buffer is buffer a disclosed in the Examples section.

In some embodiments, this reaction is conducted at room temperature (about 25° C.). However, the reaction can be conducted at other temperatures, such as 4° C., or temperatures above ° C., such as about 20° C. to about 27° C. The reaction can be performed at a pH of about 7.0 to about 7.7, such as a pH of about 7.2 to about 7.5, such as a pH of about 7.4.

More than one SpoIVA can be utilized, such as a modifiable and unmodifiable SpoIVA. Thus, the ratio of modifiable and unmodifiable SpoIVA can be adjusted on the particle construct. The ratio can be, for example, 1,000:1, 100:1, 10:1, 1:1, 1:10, 1:100, or 1:1,000. In other examples, the ratio is 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, or 1:10.

Any agent can be delivered using the disclosed particle constructs. In some embodiments, the agent is covalently linked to the SpoIVA by any means. In further embodiments, the agent of interest can be covalently linked to a cysteine at the N-terminus of SpoIVA, or a cysteine within 1, 2, 3, 4, 5, 6, 7, 8, 9, 10, 11, 12, 13, 14 15, 16, 17, 18, 19, or 20 amino acids of the N-terminus of SpoIVA.

The disclosed particle constructs include one or more agents of interest linked to the SpoVA. Several agents of interest can be included on the surface of the disclosed particle constructs, for example, by incorporating a streptavidin-fused SpoIVA in the particle construct, which can then interact with multiple biotin-conjugated molecules of interest. Alternatively, a biotin-fused SpoIVA can be included in the particle construct, which can then interact with multiple avident-conjugated agents of interest.

In specific, non-limiting examples, click chemistry can be used to covalently link an agent of interest to the SpoIVA. Click chemistry includes, but is not limited to, [3+2] cycloadditions, such as the Huisgen 1,3-dipolar cycloaddition, thiol-ene click reactions' Diels-Alder reaction, inverse electron demand Diels-Alder reaction, [4+1] cycloadditions between isonitriles (isocyanides) and tetrazines nucleophilic substitution especially to small strained rings like epoxy and aziridine compounds, carbonyl-chemistry-like formation of ureas, and addition reactions to carbon-carbon double bonds such as dihydroxylation or the alkynes in the thiol-yne reaction.

In some embodiments, SpoIVA is modified with trans-cyclooctene, tetrazine, dibenzocyclooctyne (DBCO), or azide so that an agent of interest can be covalently linked to the SpoVIA. The SpoIVA can be modified prior to adsorption to SpoVM, or after adsorption to SpoVM.

In specific non-limiting examples, a cysteine at the N-terminus or within 20 amino acids of the N-terminus of the SpoIVA, such as within 20, 19, 18, 17, 16, 15, 14, 13, 12, 11, 10, 9, 8, 7, 6, 5, 4, 3, or 2 amino acids of the N-terminus, or at the N-terminus, is modified with trans-cyclooctene, tetrazine, DBCO, or azide prior to incubating the supported lipid bilayer with SpoIVA. In specific non-limiting examples, the cysteine at the N-terminus or within 20, 19, 18, 17, 16, 15, 14, 13, 12, 11, 10, 9, 8, 7, 6, 5, 4, 3, or 2 amino acids of SpoIVA is modified with trans-cyclooctene, and the agent of interest is labeled with tetrazine, such that reaction of the trans-cyclooctene with the tretrazine covalently links the agent of interest to the SpoIV. In additional non-limiting examples, the cysteine at the N-terminus or within 20, 19, 18, 17, 16, 15, 14, 13, 12, 11, 10, 9, 8, 7, 6, 5, 4, 3, or 2 amino acids of SpoIVA is modified with tretrazine, and the agent of interest is labeled with trans-cyclooctene, such that reaction of the trans-cyclooctene with the tretrazine covalently links the agent of interest to the SpoIVA. In further examples, the cysteine at the N-terminus or within 20, 19, 18, 17, 16, 15, 14, 13, 12, 11, 10, 9, 8, 7, 6, 5, 4, 3, or 2 amino acids of the N-terminus of SpoIVA is modified with azide, the agent of interest is labeled with a DBCO, such that reaction of the azide with the DBCO covalently links the agent of interest to the SpoIVA. In yet other examples, the cysteine at the N-terminus or within 20, 19, 18, 17, 16, 15, 14, 13, 12, 11, 10, 9, 8, 7, 6, 5, 4, 3, or 2 amino acids of the N-terminus of SpoIVA is modified with DBCO, and the agent of interest is labeled with an azide, such that reaction of the azide with the dibenzocyclooctyne covalently links the agent of interest to the SpoIVA.

In specific non-limiting examples, the SpoIVA has a cysteine at the N-terminus or within 10 amino acids of the N-terminus of the SpoIVA with trans-cyclooctene, tetrazine, DBCO, or azide prior to incubating the supported lipid bilayer with SpoIVA. In additional non-limiting examples: (a) the cysteine at the N-terminus or within 10 amino acids of SpoIVA is modified with trans-cyclooctene, and wherein the method further comprises contacting the particle with an agent of interest labeled with tetrazine, wherein reaction of the trans-cyclooctene with the tretrazine covalently links the agent of interest to the SpoIVA; or (b) the cysteine at the N-terminus or within 10 amino acids of SpoIVA is modified with tretrazine, and wherein the method further comprises contacting the particle with an agent of interest labeled with trans-cycooctene, wherein reaction of the trans-cyclooctene with the tretrazine covalently links the agent of interest to the SpoIVA.

In yet other examples (a) the cysteine at the N-terminus or within 10 amino acids of the N-terminus of SpoIVA is modified with azide, and wherein the method further comprises contacting the particle with an agent of interest labeled with a DBCO, wherein reaction of the azide with the DBCO covalently links the agent of interest to the SpoIVA; or (b) the cysteine at the N-terminus or within 10 amino acids of the N-terminus of SpoIVA is modified with DBCO, and wherein the method further comprises contacting the particle with an agent of interest labeled with an azide, wherein reaction of the azide with the DBCO covalently links the agent of interest to the SpoIVA.

The reactions listed above are exemplary. In some embodiments, copper-free click chemistry is also of use to link an agent of interest to SpoIVA. An example is phosphine-azide ligation wherein agents of interest, such as fluorescent dyes, DNA, peptides, oligonucleotides, or sugars are modified with phosphine and/or azide (Staudinger-Bertozzi ligation, see the Sigma Aldrich website). In addition, azide modified SpoIV can be covalently linked to an agent of interest using MOFO: monofluorinated cyclooctyne (MOFO), Difluorinated cyclooctyne (DIFO), Aryl-cyclooctyne, dibenzocyclooxtyne (MO), aza-dibenzocyclooctyne (DIBAC), biarylazacyclooctynone (BARAC), or bicycle [6.1.0]nonyne (BCN). In other embodiments, tetrazine-modified SpoIVA can be covalently linked to an agent of interest conjugated with TCO or Norbornene.

In yet other embodiments, copper(I)-catalyzed click chemistry can be used, wherein one molecule (SpoIVA or the agent of interest) is conjugated with an alkyne and the other is conjugated to an azide. Alkyne derivatives include Alkyne-PEG4-NHS Ester, Propargyl-NHS Ester, Alkyne-PEG4-Amine, Alkyne-PEG4-Maleimide, Propargyl-Maleimide, biotinlyated alkyne (eg: Biotin-PEG4-Alkyne), fluorescent alkyne (eg. Cy3 Alkyne). Azide derivatives include: Azido-PEG4-NHS Ester, Azido-PEG3-Amine, Azido-PEG3-Maleimide, biotinylated azide (eg: Biotin-PEG3-Azide, TAMRA-Azide-Biotin), fluorescent azide (eg. Cy5 Azide) (see the Click Chemistry Tools website, available on the internet clickchemistrytools.com/products/click_chemistry_toolbox/alkyne_reagents/ and clickchemistrytools.com/products/click_chemistry_toolbox/azides_reagents/). Molecular probes such as DNA, sugar, lipid that have already been modified with azide or alkyne for ligation are commercially available, see the Life Technologies website (lifetechnologies.com/us/en/home/references/molecular-probes-the-handbook/tables/molecular-probes-azide-and-alkyne-derivatives.html).

Thus, one of skill in the art can readily produce the disclosed particle construct using the guidance provided herein. In some embodiments, the methods include coating a synthetic core with a solid surface (see above) with a lipid bilayer to form a supported lipid bilayer, saturating the surface of the supported lipid bilayer with SpoVM, and incubating the supported lipid bilayer with SpoIVA, generally in the presence of adenosine triphosphate (ATP), thereby producing the particle. One of more agents of interest is then covalently attached to the SpoIV, such as by using click chemistry or using other binding partners such as streptavidin/biotin.

An agent of interest can be any molecule that is desired to be delivered to an environment or a subject. An agent of interest can be an enzyme, a detectable marker, a pharmaceutical compound, an immunosuppressant, a growth factor or a vaccine.

An agent of interest can be an antibody, including, but not limited to, monoclonal antibodies, antigen binding fragments such as a Fab, Fab', SCA, Fv, scFv, or a nanobody. The antibody can also be a humanized, fully human, or chimeric antibody.

In one embodiment, an agent of interest is a pharmaceutical compound. Specific non-limiting examples of a pharmaceutical compound are a chemotherapeutic agent, a radionucleotide, an analgesic, an anti-inflammatory agent, an anti-arrhythmic agent, an anti-coagulant, an anti-hypertensive agent, a lipid regulating agent, an anti-bacterial agent, an anti-viral agent, an anti-fungal agent, an anti-malarial agent, an anti-neoplastic agent, an immunosuppressant, an anti-protozoal agent, a psychotropic agent, a steroid, a diuretic, a histamine receptor antagonist, an anti-anginal agents, a nutritional compound, a protease inhibitor, a hormone, a stimulant, a muscle relaxant, a vaccine, an immunotoxin or an anti-osteoporosis agent.

In some non-limiting examples, the agent is a vaccine, such as an antigenic molecule, such as, but not limited to, a viral, bacterial or fungal antigen. The viral antigen can be, for example, an antigen from a dengue virus, a human immunodeficiency virus, an influenza virus, a metapneumovirus, a norovirus, a papillomavirus, a parvovirus, a SARS virus, a smallpox virus, a picornaviruses, a respiratory syncitial virus, a parainfluenza virus, a measles virus, a hepatitis virus, an Ebola virus, a varicella zoster virus, a rabies virus or a West Nile virus. Bacterial and fungal species are listed below. In yet other embodiments, the particle construct includes a vaccine and an immunostimulatory molecule, such as for use as an adjuvant.

The agent of interest can be a polypeptide, a nucleic acid, a chemical, such as a small molecule or drug, a steroid, a proteoglycan, a lipid, a carbohydrate and combinations or conjugates thereof. The agent can be a prodrug that is metabolized and thus converted in vivo to its active (and/or stable) form. The agent of interest can be a tumor antigen, a self or autoimmune antigen, a microbial antigen, an allergen, or an environmental antigen. The antigen can be peptide, lipid, or carbohydrate, but it is not so limited.

Examples of polypeptides include antibodies, single chain antibodies, antigen binding antibody fragments, Fc domains, enzymes, co-factors, receptors, ligands, transcription factors and other regulatory factors, antigens, cytokines, chemokines, and the like. These peptide-based agents can be naturally or non-naturally occurring.

The agent of interest can be an immunomodulatory agents such as immunostimulatory agents and immunoinhibitory agents, antigens, adjuvants, cytokines, chemokines, anticancer agents, anti-infective agents, nucleic acids, antibodies or fragments thereof, fusion proteins such as cytokine-antibody fusion proteins, Fc-fusion proteins Immunostimulatory agents stimulate an immune response (including enhancing a pre-existing immune response) when administered to a subject alone or in combination with another agent. Examples of immunostimulatory agents are adjuvants (imiquimod and resiquimod and other imidazoquinolines), Toll-like receptor ligands, oligonucleotides including an unmethylated CpG dinucleotide (D-type CpG and K-type CpG oligodeoxynucleotides), monophosphoryl lipid A (MPLA) and other lipopolysaccharide derivatives, single-stranded or double-stranded RNA, flagellin, muramyl dipeptide), interleukins (for example, IL-2, IL-7, IL-15), and other cytokines (such as interferon (IFN)-γ, IFN-α, granulocyte macrophage colony stimulating factor (GM-CSF), tumor necrosis factor (TNF)-α, TNF-β), immunostimulatory antibodies (for example, anti-CTLA-4, anti-CD28, anti-CD3, anti-programmed death (PD)-1, anti-PD-L1, and or single chain and antigen binding fragments of these antibodies), amongst others. In some embodiments, the agent of interest is a PD-1 antagonist, such as antibody that specifically binds PD-1 or PD-L1, such as MPDL3280A.

The agent can be a chemokine. Chemokines are biochemical signaling molecules that act to attract other particular molecules, including but not limited to cells, to a specific site. The chemokine can be a CC chemokine, CXC chemokine, C chemokine, or CX3C chemokine. Exemplary chemokines are CCL1, CCL2, CCL3, CCL4, CCL5, CCL6, CCL7, CCL8, CCL9/CCL10, CCL11, CCL12, CCL13, CCL14, CCL15, CCL16, CCL17, CCL18, CCL19, CCL20, CCL21, CCL22, CCL23, CCL24, CCL25, CCL26, CCL27, CCL28, CCL29, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCL17, CXCL18, CXCL19, CXCL20, CXCL21, CXCL22, XCL1, XCL2, XCL3, XCL4, XCL5, CX3CL1, CX3CL2, and CX3CL3.

Immunosuppressive agents include a non-steroidal anti-inflammatory agent, such as diclofenac, diflunisal, etodolac, flurbiprofen, ibuprofen, indomethacin, ketoprofen, ketorolac, nabumetone, naproxen, oxaprozin, piroxicam, sulindac, tolmetin, celecoxib, or rofecoxib, a steroid, such as cortisone, dexamethasone, hydrocortisone, methylprednisolone, prednisolone, prednisone, or triamcinolone, or an immunosuppressive agent, for example cyclosporin, tacrolimus, mycophenolic acid, or sirolimus. Immunosuppressive agents include KINERET® (anakinra), ENBREL® (etanercept), or REMICADE® (infliximab), a disease-modifying antirheumatic drug (DMARD), such as ARAVA® (leflunomide), a nonsteroidal anti-inflammatory drug (NSAIDs), specifically a Cyclo-Oxygenase-2 (COX-2) inhibitor, such as CELEBREX® (celecoxib) and VIOXX® (rofecoxib), or another product, such as HYALGAN® (hyaluronan) and SYNVISC® (hylan G-F20).

In some non-limiting examples, the agent is a tumor antigen. Optionally, a particle construct can include the tumor antigen and an immunostimulatory molecule. A tumor antigen is expressed preferentially by tumor cells (i.e., it is expressed at higher levels in tumor cells than on non-tumor cells) and in some instances it is expressed solely by tumor cells.

Exemplary tumor antigens include, but are not limited to, MART-1/Melan-A, gp100, adenosine deaminase-binding protein (ADAbp), FAP, cyclophilin b, colorectal associated antigen (CRC)--0017-1A/GA733, carcinoembryonic antigen (CEA), CAP-1, CAP-2, etv6, AML1, prostate specific antigen (PSA), PSA-1, PSA-2, PSA-3, prostate-specific membrane antigen (PSMA), T cell receptor/CD3-zeta chain, and CD20. Additional tumor antigens include, but are not limited to, MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5). Tumor antigens also include, but are not limited to GAGE-1, GAGE-2, GAGE-3, GAGE-4, GAGE-5, GAGE-6, GAGE-7, GAGE-8, GAGE-9. The tumor antigen can also be BAGE, RAGE, LAGE-1, NAG, GnT-V, MUM-1, CDK4, tyrosinase, p53, MUC family, HER2/neu, p21ras, RCAS1, .alpha.-fetoprotein, E-cadherin, α-catenin, .β.-catenin, γ-catenin, p120ctn, gp100.sup.Pmel117, PRAME, NY-ESO-1, cdc27, adenomatous polyposis coli protein (APC), fodrin, Connexin 37, Ig-idiotype, p15, gp75, GM2 ganglioside, GD2 ganglioside, human papilloma virus proteins, a member of the Smad family of tumor antigens, lmp-1, P1A, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, CD20, and c-erbB-2.

Tumor antigens can also be classified according to the cancer or tumor they are associated with (i.e., expressed by). Tumors associated with specific antigens include acute lymphoblastic leukemia (etv6; aml1; cyclophilin b), B cell lymphoma (Ig-idiotype); Burkitt's (Non-Hodgkin's) lymphoma (CD20); glioma (E-cadherin; .alpha.-catenin; .beta.-catenin; .gamma.-catenin; p120ctn), bladder cancer (p21ras), biliary cancer (p21ras), breast cancer (MUC family; HER2/neu; c-erbB-2), cervical carcinoma (p53; p21ras), colon carcinoma (p21ras; HER2/neu; c-erbB-2; MUC family), colorectal cancer (Colorectal associated antigen (CRC)--0017-1A/GA733; APC), choriocarcinoma (CEA), epithelial cell-cancer (cyclophilin b), gastric cancer (HER2/neu; c-erbB-2; ga733 glycoprotein), hepatocellular cancer (α-fetoprotein), Hodgkin's lymphoma (lmp-1; EBNA-1), lung cancer (CEA; MAGE-3; NY-ESO-1), lymphoid cell-derived leukemia (cyclophilin b), melanoma (p15 protein, gp75, oncofetal antigen, GM2 and GD2 gangliosides), myeloma (MUC family; p21ras), non-small cell lung carcinoma (HER2/neu; c-erbB-2), nasopharyngeal cancer (lmp-1; EBNA-1), ovarian cancer (MUC family; HER2/neu; c-erbB-2), prostate cancer (Prostate Specific Antigen (PSA) and its immunogenic epitopes PSA-1, PSA-2, and PSA-3; PSMA; HER2/neu; c-erbB-2), pancreatic cancer (p21ras; MUC family; HER2/neu; c-erbB-2; ga733 glycoprotein), renal (HER2/neu; c-erbB-2), squamous cell cancers of cervix and esophagus (viral products such as human papilloma virus proteins and non-infectious particles), testicular cancer (NY-ESO-1), T cell leukemia (HTLV-1 epitopes), and melanoma (Melan-A/MART-1; cdc27; MAGE-3; p21ras; gp100.sup.Pmel1117).

The agent of interest can be a microbial antigens such as without limitation an antigen from a bacterial, viral, fungal, parasitic or mycobacterial species. Thus, microbial antigens include bacterial antigens, viral antigens, fungal antigens, parasitic antigens, and mycobacterial antigens. Examples of bacterial, viral, fungal, parasitic and mycobacterial species are provided herein, without limitation. Optionally, the particle constructs can include one or more microbial antigens and an immunostimulatory molecule.

Exemplary bacterial antigens are from *E. coli, Staphylococcal, Streptococcal, Pseudomonas, Clostridium difficile, Legionella, Pneumococcus, Haemophilus, Klebsiella, Enterobacter, Citrobacter, Neisseria, Shigella, Salmonella, Listeria, Pasteurella, Streptobacillus, Spirillum, Treponema, Actinomyces, Borrelia, Corynebacterium, Nocardia, Gardnerella, Campylobacter, Spirochaeta, Proteus, Bacteroides, H. pylori*, and *B. anthracis* A viral antigen can be derived from any viral species, such as, but not limited to, a dengue virus, a human immunodeficiency virus, an influenza virus, a metapneumovirus, a norovirus, a papillomavirus, a parvovirus, a SARS virus, a smallpox virus, a picornaviruses, a respiratory syncitial virus, a parainfluenza virus, a measles virus, a hepatitis virus, an Ebola virus, a herpes simplex virus, a varicella zoster virus, a rabies virus or a West Nile virus.

Exemplary fungal antigens are from any fungal species that causes an infection, such as, but not limited to, candidiasis, ringworm, histoplasmosis, blastomycosis, paracoccidioidomycosis, crytococcosis, aspergillosis, chromomycosis, mycetoma infections, pseudallescheriasis, and tinea *versicolor* infection. Exemplary parasitic antigens are from amebiasis, *Trypanosoma cruzi, Fascioliasis, Leishmaniasis, Plasmodium, Onchocerciasis, Paragonimiasis, Trypanosoma brucei, Pneumocystis, Trichomonas vaginalis, Taenia, Hymenolepsis, Echinococcus, Schistosomiasis, neurocysticercosis, Necator americanus*, and *Trichuris trichiura*. Exemplary mycobacterial antigens are from *M. tuberculosis* and *M. leprae*, but is not so limited.

The agent of interest can be an allergen. Allergens include without limitation pollens, insect venoms, animal dander dust, fungal spores and drugs (such as penicillin). Examples of natural, animal and plant allergens include but are not limited to proteins specific to the following genera: Canine (*Canis familiaris*); *Dermatophagoides* (e.g. *Dermatophagoides farinae*); *Felis* (*Felis domesticus*); *Ambrosia* (*Ambrosia artemiisfolia; Lolium* (e.g. *Lolium perenne* or *Lolium multiflorum*); *Cryptomeria* (*Cryptomeria japonica*); *Alternaria* (*Alternaria alternata*); Alder; *Alnus* (*Alnus gultinoasa*); *Betula* (*Betula verrucosa*); *Quercus* (*Quercus alba*); *Olea* (*Olea europa*); *Artemisia* (*Artemisia vulgaris*); *Plantago* (e.g. *Plantago lanceolata*); *Parietaria* (e.g. *Parietaria officinalis* or *Parietaria judaica*); *Blattella* (e.g. *Blattella germanica*); *Apis* (e.g. *Apis multiflorum*); *Cupressus* (e.g. *Cupressus sempervirens, Cupressus arizonica* and *Cupressus macrocarpa*); *Juniperus* (e.g. *Juniperus sabinoides, Juniperus virginiana, Juniperus communis* and *Juniperus ashei*); *Thuya* (e.g. *Thuya orientalis*); *Chamaecyparis* (e.g. *Chamaecyparis obtusa*); *Periplaneta* (e.g. *Periplaneta americana*); *Agropyron* (e.g. *Agropyron repens*); *Secale* (e.g. *Secale cereale*); *Triticum* (e.g. *Triticum aestivum*); *Dactylis* (e.g. *Dactylis glomerata*); *Festuca* (e.g. *Festuca elatior*); *Poa* (e.g. *Poa pratensis* or *Poa compressa*); *Avena* (e.g. *Avena sativa*); *Holcus* (e.g. *Holcus lanatus*); *Anthoxanthum* (e.g. *Anthoxanthum odoratum*); *Arrhenatherum* (e.g. *Arrhenatherum elatius*); *Agrostis* (e.g. *Agrostis alba*); *Phleum* (e.g. *Phleum pratense*); *Phalaris* (e.g. *Phalaris arundinacea*); *Paspalum* (e.g. *Paspalum notatum*); *Sorghum* (e.g. *Sorghum halepensis*); and *Bromus* (e.g. *Bromus inermis*). Thus, in some embodiments, the agent of interest is a tolerogenic antigen.

In yet other embodiments, the agent of interest is an enzyme. Suitable enzymes include any bioremediation enzyme that metabolizes an environmental pollutant. In some embodiments, the enzyme is laccase, a hydrolase, a dehalogenase, a transferase, or an oxidoreductase, a lyase, a lipase, a cellualse, a hemicullulase, a petinase, and an isomerase, or a ligase. In other embodiments, the enzyme is a phosphotriesterase, an amidase, a protease, a carbohydrase, a cellulase, an amylase, a depolymerase, a lipase, a mono-oxygenase, a di-oxygenase, a reductase, a cytochrome P450 monoxygenase, a phenoloxidase, or a peroxidase. In specific non-limiting examples, the enzyme can aid in bioremediation of petroleum, such as, but not limited to bioremediation of petroleum-contaminated soils or water. In some embodiments, the enzyme is a bacterial or fungal enzyme. The enzyme can be, for example, from *Pseudomonas putida, Dechloromonas aromatica, Nitorsomas europea, Nitrobacter hamburgensis, Paracoccus denitrificans, Phanerochaete chrysosporium, Deinococcus radiodurans, Comamona acidovorans*, or *Methylibium petroleiphilum*. The enzyme can be used in the degradation of, for example, polychlorinated biphenyls, polycyclic aromatic compounds, pesticides, synthetic dyes, chlorphenols, wastewater effluents, or polyurethane. Suitable enzymes also include those involved in biotechnology and industrial applications, such as food or fuel production. The enzyme can be an amylase, a lipoprotein lipase, a pectinase, pepsin, trypsin. The enzyme can be a laccase.

The agent of interest can be a detectable label. Detectable labels include radioisotopes, fluorescent labels, and enzymes that form a detectable reaction product.

In some embodiments, the detectable marker is a radioisotope. The radioisotope can be any of the radioisotopes known in the art. In some embodiments, the radioisotope has half-life sufficient for detecting a nanoparticle over a significant period of time, for example, the radioisotope has a half-life of at least 25, 50, 75, 100, 150, 200, 250, 300, 350 days, or a half-life of at least 1, 2, 3, 4, 5, or 10 years. Some particular examples of radioisotopes having half-lives of at least 25 days include carbon-14, technetium-97, technetium-99, potassium-40, iodine-125, iodine-129, cesium-135, cesium-137, palladium-107, cadmium-113, strontium-90, europium-55, and tin-126.

In other embodiments, the radioisotope has a shorter half-life, such as up to 20, 15, 10, or 5 days, or up to 1 day, or less than 1 day. The radioisotope can have a half-life of greater than 1, 2, 3, 6, or 12 hours, or at least or greater than 1, 2, 2.5, 3, 5, or 10 days. Some examples include phosphorus-32, phosphorus-33, technetium-99m, technetium-97m, technetium-94m, technetium-94, iodine-123, iodine-124, iodine-131, fluorine-18, tin-121, gallium-67, gallium-68, rhenium-186, and rhenium-188. Such radioisotopes are suitable in such diagnostic techniques as positron emission tomography (PET). In particular embodiments, the radioisotope is one that is not toxic, such that it is medically useful, for example for medical imaging applications).

In additional embodiments, the detectable label is a fluorophore. A "fluorophore" is any species possessing a fluorescent property when appropriately stimulated. The stimulation that elicits fluorescence is typically illumination, although other types of stimulation (e.g., collisional) can also be used. Bioluminescent markers are also of use, such as luciferase, Green fluorescent protein (GFP) and Yellow fluorescent protein (YFP).

In particular embodiments, the fluorophore is an organic fluorophore (organofluorophore). The organic fluorophore can be, for example, a charged (i.e., ionic) molecule (e.g., sulfonate or ammonium groups), uncharged (i.e., neutral) molecule, saturated molecule, unsaturated molecule, cyclic molecule, bicyclic molecule, tricyclic molecule, polycyclic molecule, acyclic molecule, aromatic molecule, and/or heterocyclic molecule (i.e., by being ring-substituted by one or more heteroatoms selected from, for example, nitrogen, oxygen and sulfur). The unsaturated fluorophores may contain one or more carbon-carbon and/or carbon-nitrogen double and/or triple bonds. In some embodiments, the fluorophore is a fused polycyclic aromatic hydrocarbon (PAH) containing at least two, three, four, five, or six rings (e.g., naphthalene, pyrene, anthracene, chrysene, triphenylene, tetracene, azulene, and phenanthrene) wherein the PAH can be optionally ring-substituted or derivatized by one, two, three or more heteroatoms or heteroatom-containing groups.

The organic fluorophore may also be a xanthene derivative, such as fluorescein, rhodamine, or eosin; cyanine, or its derivatives or subclasses, such as the streptocyanines, hemicyanines, closed chain cyanines, phycocyanins, allophycocyanins, indocarbocyanines, oxacarbocyanines, thiacarbocyanines, merocyanins, and phthalocyanines; naphthalene derivatives, such as the dansyl and prodan derivatives; coumarin and its derivatives; oxadiazole and its derivatives, such as the pyridyloxazoles, nitrobenzoxadiazoies, and benzoxadiazoles; pyrene and its derivatives; oxazine and its derivatives, such as Nile Red, Nile Blue, and cresyl violet; acridine derivatives, such as proflavin, acridine orange, and acridine yellow; arylmethine derivatives, such as auramine, crystal violet, and malachite green; and the tetrapyrrole derivatives, such as the porphyrins and bilirubins. Some particular families of dyes considered herein are the CY® family of dyes (e.g., CY® 2, CY® 3, CY® 3B, CY® 3.5, CY® 5, CY® 5.5, and CY® 7), the ALEXA® family of dyes (e.g., ALEXA FLUOR® 350, 405, 430, 488, 500, 514, 532, 546, 555, 568, 594, 610, 633, 647, 660, 680, 700, 750, and 790), the ATTO® family of dyes (e.g., ATTO® 390, 425, 465, 488, 495, 520, 532, 550, 565, 590, 594, 601, 615, 619, 629, 635, 645, 663, 680, 700, 729, and 740), and the DY® family of dyes (e.g., DY® 530, 547, 548, 549, 550, 554, 556, 560, 590, 610, 615, 630, (331, 631, (332, 633, (334, 635, 636, 647, 648, 649, 650, 651, 652, 675, 676, 677, 680, 681, 682, 700, 701, 730, 731, 732, 734, 750, 7511, 752, 776, 780, 7811, 782, and 831), The ATTO® dyes, in particular, can have several structural motifs, including, coumarin-based, rhodamine-based, carbopyronin-based, and oxazine-based structural motifs. In particular embodiments, the fluorophore is selected from a sulfonated aminocoumarin, rhodamine, or carbocyanine dye, any of which may be an ALEXA FLUOR® dye, in some embodiments, the fluorophore is pH-sensitive. A particular class of pH-sensitive fluorophores considered herein is the seminaphthorhodafluor (SNARF®) class of fluorophores.

The detectable label can also be an enzyme that has a detectable reaction product, such as horseradish peroxidase, β-galactosidase, luciferase, alkaline phosphatase, glucose oxidase and the like. In these embodiments, the particle construct can be detected by adding additional reagents that the enzyme uses to produce a reaction product that can be discerned. For example, when horseradish peroxidase is present the addition of hydrogen peroxide and diaminobenzidine leads to a colored reaction product, which is visually detectable. The agent of interest can be biotin, which can be detected through indirect measurement of avidin or streptavidin binding. It should be noted that the avidin itself can be conjugated to an enzyme or a fluorescent label. The agent of interest also can be avidin, which can be detected through measurement of biotin binding. The biotin itself can be conjugated to an enzyme or a fluorescent label.

The agent of interest can be a paramagnetic agent, such as gadolinium. Paramagnetic agents such as superparamagnetic iron oxide are also of use as labels. Antibodies can also be conjugated with lanthanides (such as europium and dysprosium), and manganese. The agent of interest also can be a predetermined polypeptide epitope recognized by a secondary reporter (such as leucine zipper pair sequences, binding sites for secondary antibodies, metal binding domains, epitope tags).

The agent of interest can be a chemotherapeutic agent. Examples of chemotherapeutic agents are alkylating agents, antimetabolites, natural products, or hormones and their antagonists. Examples of alkylating agents include nitrogen mustards (such as mechlorethamine, cyclophosphamide, melphalan, uracil mustard or chlorambucil), alkyl sulfonates (such as busulfan), nitrosoureas (such as carmustine, lomustine, semustine, streptozocin, or dacarbazine). Examples of antimetabolites include folic acid analogs (such as methotrexate), pyrimidine analogs (such as 5-fluorouracil or cytarabine), and purine analogs, such as mercaptopurine or thioguanine. Examples of natural products include vinca alkaloids (such as vinblastine, vincristine, or vindesine), epipodophyllotoxins (such as etoposide or teniposide), antibiotics (such as dactinomycin, daunorubicin, doxorubicin, bleomycin, plicamycin, or mitomycin C), and enzymes (such as L-asparaginase). Examples of additional agents include platinum coordination complexes (such as cis-diamine-dichloroplatinum II also known as cisplatin), substituted ureas (such as hydroxyurea), methyl hydrazine derivatives (such as procarbazine), and adrenocrotical suppressants (such as mitotane and aminoglutethimide). Non-limiting examples of hormones and antagonists include adrenocorticosteroids (such as prednisone), progestins (such as hydroxyprogesterone caproate, medroxyprogesterone acetate, and magestrol acetate), estrogens (such as diethylstilbestrol and ethinyl estradiol), antiestrogens (such as tamoxifen), and androgens (such as testerone proprionate and fluoxymesterone). Non-limiting examples of the commonly used chemotherapy drugs include Adriamycin, Alkeran, Ara-C, BiCNU, Busulfan, CCNU, Carboplatinum, Cisplatinum, Cytoxan, Daunorubicin, DTIC, 5-FU, Fludarabine, Hydrea, Idarubicin, Ifosfamide, Methotrexate, Mithramycin, Mitomycin, Mitoxantrone, Nitrogen Mustard, Taxol (or other taxanes, such as docetaxel), Velban, Vincristine, VP-16, while some more newer drugs include Gemcitabine (Gemzar), Herceptin, Irinotecan (Camptosar, CPT-11), Leustatin, Navelbine, Rituxan STI-571, Taxotere, Topotecan (Hycamtin), Xeloda (Capecitabine), Zevelin and calcitriol. Non-limiting examples of immunomodulators that can be used include AS-101 (Wyeth-Ayerst Labs.), bropirimine (Upjohn), interferon (IFN)-γ (Genentech), GM-CSF (granulocyte macrophage colony stimulating factor; Genetics Institute), IL-2 (Cetus or Hoffman-LaRoche), human immune globulin (Cutter Biological), IMREG (from Imreg of New Orleans, La.), SK&F 106528, and tumor necrosis factor (TNF, Genentech).

Additional non-limiting examples of products of use are ALIMTA® (Pemetrexed Disodium), AVASTIN® (Bevacizumab), Gefitinib, GILOTRIF® (Afatinib Dimaleate), GEMZAR® (Gemcitabine Hydrochloride), IRESSA® (Gefitinib), Methotrexate, TAXOL® (Paclitaxel), ABRAXANE® (Paclitaxel Albumin-stabilized Nanoparticle Formulation), PARAPLAT® (Carboplatin), PARAPLATIN® (Carboplatin), Pemetrexed Disodium, PLATINOL® (Cisplatin), PLATINOL-AQ® (Cisplatin), TARCEVA® (Erlotinib Hydrochloride), TAXOTERE® (Docetaxel), XALKORI® (Crizotinib), and ZYKADIA® (Ceritinib), ABITREXATE® (Methotrexate), ETOPOPHOS (Etoposide Phosphate), Etoposide, Etoposide Phosphate, FOLEX® (Methotrexate). FOLEX PFS® (Methotrexate), HYCAMTIN® (Topotecan Hydrochloride), Methotrexate, METHOTREXATE LPF® (Methotrexate), MEXATE (Methotrexate), MEXATE-AQ® (Methotrexate), TOPOSAR® (Etoposide), Topotecan Hydrochloride, and VEPESID® (Etoposide).

The agent of interest can be an immunosuppressant, such as a glucocorticoid, a cytostatic (alkylating agents, antimetabolites, methotrexate, azathioprine, or mercaptopurine), and antibody (for example, an antibody that specifically binds CD3 such as muronomab, an antibody that specifically binds the IL-2 receptor such as daclizumab or basiliximab), an interferon, a cyclosporine (for example, Cyclosporine A or ciclosporin), tacrolimus, Sirolimus, a cyclosporine, an opioid, a TNF binding protein, mycophenolate, a small molecule (for example, fingolimod or myriocin).

In some embodiments, only one agent of interest is included in the particle construct. However, the particle construct can also include 2, 3, 4, 5, 6, 7, 8, 9 or 10 agents of interest. In specific non-limiting examples the particle construct includes two agents of interest, such as two different chemotherapeutics, or an antigen and an immunostimulatory agent, such as a tumor antigen and an immunostimulatory agent such as an adjuvant, or an antigen from a pathogen (for example, a virus, a bacteria, or a fungus) and an immunostimulatory agent. In some embodiments, an adjuvant is not utilized.

Methods of Treatment

The particle constructs disclosed herein can be used in any subject, including those with a tumor, an infection with a pathogen, an autoimmune disease, or an allergy. However, the particle constructs can also be administered to healthy subjects, such as those in need of vaccination. Thus, any subject can be treated using the particle constructs disclosed herein.

Generally the agent of interest is selected for the treatment of the particular subject. The subject can be a human or a veterinary subject. Thus, subjects also include animals such as household pets (such as dogs, cats, rabbits and ferrets), livestock or farm animals (such as cows, pigs, sheep, chickens and other poultry), horses (such as thoroughbred, Arabian or Saddlebred horses), laboratory animals (such as mice, rats, rabbits, etc.), zoo or wild animals (such as giraffes, zebras, lions and tigers) and birds (such as chickens, turkeys, pigeons parrots and parakeets). Subjects also include fish and other aquatic species. The subject can have a specific disease or disorder, or can be at risk of developing the disease or disorder. Treating a disorder or disease can include reducing or eliminating one or more symptoms of the condition. Administration can be local or systemic. The subject is administered a therapeutically effective amount of one or more particle constructs disclosed herein.

Tests for diagnosing the conditions are known in the art and will be familiar to the ordinary medical practitioner. These laboratory tests include without limitation microscopic analyses, cultivation dependent tests (such as cultures), and nucleic acid detection tests. These include wet mounts, stain-enhanced microscopy, immune microscopy (e.g., FISH), hybridization microscopy, particle agglutination, enzyme-linked immunosorbent assays, urine screening tests, DNA probe hybridization, and serologic test. A practitioner can take a medical history and conduct a complete physical examination in addition to running the laboratory tests to select a subject for treatment.

In some embodiments, the subject will benefit from immune stimulation, particularly and an antigen specific immune response. Such a response may be a humoral or a cellular immune response. A subject can be treated that has a tumor (a solid tumor or non-solid tumor such as leukemias), an infections (such as bacterial, viral or fungal infection), an autoimmune disorder, an allergy or allergic condition, asthma, or has transplant rejection. The subject can have an autoimmune disorder.

In some embodiments, the subject has a tumor or is at risk for developing a tumor. These subjects include, for instance, subjects having a genetic abnormality that has been demonstrated to be associated with a higher likelihood of developing a cancer, subjects having a familial disposition to cancer, subjects exposed to cancer causing agents (i.e., carcinogens) such as tobacco, asbestos, or other chemical toxins, and subjects previously treated for cancer and in apparent remission. In some embodiments these subject are administered a therapeutically effective amount of a particle construct disclosed herein, wherein the agent of interest is a tumor antigen and/or a chemotherapeutic agent. Suitable tumor antigens and chemotherapeutics are disclosed above. In other embodiments, these subject are administered a therapeutically effective amount of a particle construct disclosed herein, wherein the agent of interest is an immunostimulatory molecule, such as, but not limited to, an antibody that specifically binds PD-1 or PD-L1. It should be noted that these embodiments are not mutually exclusive; a subject can be administered more than one particle construct, each with a different agent of interest, or a particle construct including more than one agent of interest.

The subject can have, or be at risk for developing, a hematological tumor. Examples of hematological tumors that can be treated using the methods disclosed herein include leukemias, such as acute leukemias (such as 11q23-positive acute leukemia, acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

The subject can have, or be at risk for developing, a solid tumor. Examples of solid tumors that can be treated using the methods disclosed herein include sarcomas and carcinomas, such as fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer (including basal breast carcinoma, ductal carcinoma and lobular breast carcinoma), lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyngioma, ependymoma, pinealoma, hemangioblastoma, acoustic neuroma, oligodendroglioma, meningioma, melanoma, neuroblastoma and retinoblastoma). In several examples, a tumor is melanoma, lung cancer, lymphoma breast cancer or colon cancer.

The subject can have an infection or be at risk of contracting an infection due to a risk of exposure to a pathogen. These subjects include those that live in an area where such pathogens are known to exist and where such infections are common. These subjects also include those that engage in high risk activities such as sharing of needles, engaging in unprotected sexual activity, routine contact with infected samples of subjects (e.g., medical practitioners), people who have undergone surgery, including but not limited to abdominal surgery. Thus, the subject may have or may be at risk of developing an infection such as a bacterial infection, a viral infection, a fungal infection, a parasitic infection or a mycobacterial infection. In some embodiments, these subjects are administered a therapeutically effective amount of a particle construct disclosed herein, wherein the agent of interest is a tumor antigen. Subjects can also be administered additional agents, such as chemotherapeutic agents.

In some embodiments, a therapeutically effective amount of a particle construct is administered to the subject, wherein the agent of interest is a microbial antigen and/or an adjuvant. The subject can have, or be at risk of having, a viral infection, a fungal infection, a parasitic infection or a mycobacterial infection. Thus, the microbial antigen may be a bacterial antigen, a viral antigen, a fungal antigen, a parasitic antigen, or a mycobacterial antigen. In addition, the subjects may be administered anti-infective agents such as anti-bacterial agents, anti-viral agents, anti-fungal agents, anti-parasitic agents, and anti-mycobacterial agents. The agent of interest can be a vaccine.

In some embodiments, the subject has or is at risk of having, a bacterial infection, such as an *E. coli* infection, a Staphylococcal infection, a Streptococcal infection, a *Pseudomonas* infection, *Clostridium difficile* infection, *Legionella* infection, *Pneumococcus* infection, *Haemophilus* infection, *Klebsiella* infection, *Enterobacter* infection, *Citrobacter* infection, *Neisseria* infection, *Shigella* infection, *Salmonella* infection, *Listeria* infection, *Pasteurella* infection, *Streptobacillus* infection, *Spirillum* infection, *Treponema* infection, *Actinomyces* infection, *Borrelia* infection, *Corynebacterium* infection, *Nocardia* infection, *Gardnerella* infection, *Campylobacter* infection, *Spirochaeta* infection, *Proteus* infection, *Bacteroides* infection, *H. pylori* infection, or *B. anthracis* infection.

In some embodiments, the subject has or is at risk of having, a mycobacterial infection such as a tuberculosis or leprosy, respectively caused by *M. tuberculosis* or *M. leprae*.

In additional embodiments, the subject has or is at risk of having, a viral infection such as a Herpes simplex virus 1 infection, a Herpes simplex virus 2 infection, cytomegalovirus infection, hepatitis A virus infection, hepatitis B virus infection, hepatitis C virus infection, human papilloma virus infection, Epstein Barr virus infection, rotavirus infection, adenovirus infection, influenza virus infection, influenza A virus infection, H1N1 (swine flu) infection, respiratory syncytial virus infection, measles, varicella-zoster virus infections, small pox infection, monkey pox infection, SARS infection or avian flu infection.

In other embodiments, the subject has or is at risk of having, a Candidiasis, ringworm, histoplasmosis, blastomycosis, paracoccidioidomycosis, crytococcosis, aspergillosis, chromomycosis, mycetoma infections, pseudallescheriasis, or tinea versicolor infection. In yet other embodiments, the subject has or is at risk of having, a parasite infection such as an infection with an amoeba, *Trypanosoma cruzi*, *Fascioliasis*, *Leishmaniasis*, *Plasmodium* infections, *Onchocerciasis*, *Paragonimiasis*, *Trypanosoma brucei* infection, *Pneumocystis*, *Trichomonas vaginalis* infection, *Taenia* infection, *Hymenolepsis*, *Echinococcus*, *Schistosomiasis*, neurocysticercosis, *Necator americanus* infection, or *Trichuris trichiura* infection.

The subject can have, or be at risk of developing, an allergy or asthma. An allergy is an acquired hypersensitivity to an allergen. Allergic conditions include but are not limited to eczema, allergic rhinitis or coryza, hay fever, bronchial asthma, urticaria (hives) and food allergies, and other atopic conditions. Asthma is a disorder of the respiratory system characterized by inflammation, narrowing of the airways and increased reactivity of the airways to inhaled agents.

The agent of interest can be an agent that stimulate a Th1 response, immunoinhibitory or immunosuppressant agents including agents that inhibit a Th2 response, anti-inflammatory agents, leukotriene antagonists, IL-4 receptors, anti-IL-4 antibodies, IL-4 antagonists, anti-IL-5 antibodies, soluble IL-13 receptor-Fc fusion proteins, anti-IL-9 antibodies, CCR3 antagonists, CCR5 antagonists, VLA-4 inhibitors, and other downregulators of IgE, such as but not limited to anti-IgE, cytokines such as IL-12 and IFN-gamma, steroids including corticosteroids such as prednisolone.

In some embodiments, the subject has an autoimmune disease, and the particle construct includes an immunosuppressive agent (see above). Autoimmune diseases include, but are not limited to inflammatory arthritis, Crohne's disease, irritable bowel syndrome, Hashimoto's thyroiditis, pernicious anemia, Addison's disease, type I diabetes, systemic lupus erythematosus, dermatomyositis, Sjogren's syndrome, dermatomyositis, lupus erythematosus, multiple sclerosis, myasthenia gravis, Reiter's syndrome, and Grave's disease, among others. In additional embodiments, the subject has a hormonal disorder, and the particle construct includes a hormone. In one non-limiting example, the subject has diabetes, and the particle construct includes insulin as the agent of interest. In another non-limiting example, the subject has Addison's disease and the particle construct includes a steroid such as cortisol, a glucocorticoid, hydrocortisone, or prednisone.

The foregoing lists are not intended to be exhaustive but rather exemplary. Those of ordinary skill in the art will identify other examples of each condition type that are amenable to prevention and treatment using the particle constructs disclosed herein.

Generally, a therapeutically effective amount of a particle construct is administered to the subject, in a dosage sufficient to provide a desirable result. The therapeutically effective amount will vary with the desired outcome, the particular condition being treated or prevented, the age and physical condition of the subject being treated, the severity of the condition, the duration of the treatment, the nature of the concurrent or combination therapy (if any), the specific route of administration and like factors within the knowledge and expertise of the health practitioner. The particle construct can be administered with or without an adjuvant.

In specific non-limiting examples, an adjuvant is not utilized. Thus, the particle constructs can be administered in the absence of an adjuvant. The particle constructs can also not include an adjuvant.

In other embodiments, an adjuvant is used with the particle constructs. Adjuvants, such as aluminum hydroxide (ALHYDROGEL®, available from Brenntag Biosector, Copenhagen, Denmark and AMPHOGEL®, Wyeth Laboratories, Madison, N.J.), Freund's adjuvant, MPL™ (3-O-deacylated monophosphoryl lipid A; Corixa, Hamilton, Ind.), IL-12 (Genetics Institute, Cambridge, Mass.) TLR agonists (such as TLR-9 agonists), CpG oligodeoxynucleotides, and other suitable adjuvants well known in the art. An adjuvant can include a Tol-like receptor (TLR) agonist.

For example, the TLR agonist can be a TLR-4 agonist such as a synthetic derivative of lipid A (see, e.g., WO 95/14026, and WO 01/46127) an alkyl Glucosaminide phosphate (AGP; see, e.g., WO 98/50399 or U.S. Pat. Nos. 6,303,347; 6,764,840). Other suitable TLR-4 ligands, capable of causing a signaling response through TLR-4 are, for example, lipopolysaccharide from gram-negative bacteria and its derivatives, or fragments thereof, in particular a non-toxic derivative of LPS (such as 3D-MPL). Other suitable TLR agonists are: heat shock protein (HSP) 10, 60, 65, 70, 75 or 90; surfactant Protein A, hyaluronan oligosaccharides, heparan sulphate fragments, fibronectin fragments, fibrinogen peptides and β-defensin-2, and muramyl dipeptide (MDP). In one embodiment the TLR agonist is HSP 60, 70 or 90. Other suitable TLR-4 ligands are as described in WO 2003/011223 and in WO 2003/099195.

Additional TLR agonists (such as an agent that is capable of causing a signaling response through a TLR signaling pathway) are also useful as adjuvants, such as agonists for TLR2, TLR3, TLR7, TLR8 and/or TLR9. Accordingly, in one embodiment, the composition further includes an adjuvant which is selected from the group consisting of: a TLR-1 agonist, a TLR-2 agonist, TLR-3 agonist, a TLR-4 agonist, TLR-5 agonist, a TLR-6 agonist, TLR-7 agonist, a TLR-8 agonist, TLR-9 agonist, or a combination thereof.

In one embodiment, a TLR agonist is used that is capable of causing a signaling response through TLR-1, for example one or more of from: Tri-acylated lipopeptides (LPs); phenol-soluble modulin; *Mycobacterium tuberculosis* LP; 5-(2, 3-bis(palmitoyloxy)-(2-RS)-propyl)-N-palmitoyl-(R)-Cys-(S)-Ser-(S)-L-ys(4)--OH, trihydrochloride (Pam3Cys) LP which mimics the acetylated amino terminus of a bacterial lipoprotein and OspA LP from *Borrelia burgdorferi*. In another embodiment, a TLR agonist is used that is capable of causing a signaling response through TLR-2, such as one or more of a lipoprotein, a peptidoglycan, a bacterial lipopeptide from *M tuberculosis, B burgdorferi* or *T pallidum*; peptidoglycans from species including *Staphylococcus aureus*; lipoteichoic acids, mannuronic acids, *Neisseria* porins, bacterial fimbriae, *Yersinia* virulence factors, CMV virions, measles haemagglutinin, and zymosan from yeast. In some embodiments, a TLR agonist is used that is capable of causing a signaling response through TLR-3, such as one or more of double stranded RNA (dsRNA), or polyinosinic-polycytidylic acid (Poly IC), a molecular nucleic acid pattern associated with viral infection. In further embodiments, a TLR agonist is used that is capable of causing a signaling response through TLR-5, such as bacterial flagellin. In additional embodiments, a TLR agonist is used that is capable of causing a signaling response through TLR-6, such as one or more of mycobacterial lipoprotein, di-acylated LP, and phenol-soluble modulin. Additional TLR6 agonists are described in WO 2003/043572. In an embodiment, a TLR agonist is used that is capable of causing a signaling response through TLR-7, such as one or more of a single stranded RNA (ssRNA), loxoribine, a guanosine analogue at positions N7 and C8, or an imidazoquinoline compound, or derivative thereof. In one embodiment, the TLR agonist is imiquimod. Further TLR7 agonists are described in WO 2002/085905. In some embodiments, a TLR agonist is used that is capable of causing a signaling response through TLR-8. Suitably, the TLR agonist capable of causing a signaling response through TLR-8 is a single stranded RNA (ssRNA), an imidazoquinoline molecule with anti-viral activity, for example resiquimod (R848); resiquimod is also capable of recognition by TLR-7. Other TLR-8 agonists which can be used include those described in WO 2004/071459.

In further embodiments, an adjuvant includes a TLR agonist capable of inducing a signaling response through TLR-9. For example, the adjuvant can include HSP90, bacterial or viral DNA, and/or DNA containing unmethylated CpG nucleotides (e.g., a CpG oligonucleotide). For example, CpG-containing oligonucleotides induce a predominantly Th1 response. Such oligonucleotides are well known and are described, for example, in WO 95/26204, WO 96/02555, WO 99/33488 and U.S. Pat. Nos. 5,278,302, 5,666,153, and 6,008,200 and 5,856,462. Accordingly, oligonucleotides for use as adjuvants in the disclosed compositions include CpG containing oligonucleotides, for example, containing two or more dinucleotide CpG motifs. Also included are oligonucleotides with mixed internucleotide linkages.

Other adjuvants that can be used in immunogenic compositions include saponins, such as QS21. In some examples, saponins are used as an adjuvant, e.g., for systemic administration. Use of saponins (e.g., use of Quil A, derived from the bark of the South American tree *Quillaja Saponaria* Molina) as adjuvants is familiar to the person of ordinary skill in the art (see, e.g., U.S. Pat. No. 5,057,540 and EP 0 362 279 B1. EP 0 109 942 B1; WO 96/11711; WO 96/33739). The haemolytic saponins QS21 and QS17 (HPLC purified fractions of Quil A) have been described as potent systemic adjuvants, and the method of their production is disclosed in U.S. Pat. No. 5,057,540 and EP 0 362 279 B1.

Mineral salts such as an aluminum or calcium salts, in particular aluminum hydroxide, aluminum phosphate and calcium phosphate, can be used as adjuvants.

Another class of suitable Th1 biasing adjuvants for use in compositions includes outer membrane proteins (OMP)-based immunostimulatory compositions. OMP-based immunostimulatory compositions are particularly suitable as mucosal adjuvants, e.g., for intranasal administration. OMP-based immunostimulatory compositions are a genus of preparations of (OMPs, including some porins) from Gram-negative bacteria, e.g., *Neisseria* species, which are useful as a carrier or in compositions for immunogens, such as bacterial or viral antigens (see, e.g., U.S. Pat. Nos. 5,726, 292; 4,707,543). Further, proteosomes have the capability to auto-assemble into vesicle or vesicle-like OMP clusters of about 20 nm to about 800 nm, and to noncovalently incorporate, coordinate, associate (e.g., electrostatically or hydrophobically), or otherwise cooperate with protein antigens (Ags), particularly antigens that have a hydrophobic moiety. Proteosomes can be prepared, for example, as described in the art (see, e.g., U.S. Pat. Nos. 5,726,292 or 5,985,284; 2003/0044425.).

Proteosomes are composed primarily of chemically extracted outer membrane proteins (OMPs) from *Neisseria meningitidis* (mostly porins A and B as well as class 4 OMP), maintained in solution by detergent (Lowell G H. Proteosomes for Improved Nasal, Oral, or Injectable Vaccines. In: Levine M M, Woodrow G C, Kaper J B, Cobon G S, eds, New Generation Vaccines. New York: Marcel Dekker, Inc. 1997; 193-206). Proteosomes can be formulated with a variety of antigens such as purified or recombinant proteins derived from viral sources. The gradual removal of detergent allows the formation of particulate hydrophobic complexes of approximately 100-200 nm in diameter (Lowell G H. Proteosomes for Improved Nasal, Oral, or Injectable Vaccines. In: Levine M M, Woodrow G C, Kaper J B, Cobon G S, eds, New Generation Vaccines. New York: Marcel Dekker, Inc. 1997; 193-206).

Combinations of different adjuvants can also be used in compositions with the disclosed particle constructs in the composition. For example, QS21 can be formulated together with 3D-MPL. The ratio of QS21:3D-MPL will typically be in the order of 1:10 to 10:1; such as 1:5 to 5:1, and often substantially 1:1. Typically, the ratio is in the range of 2.5:1 to 1:1 3D-MPL:QS21 (such as AS01 (GlaxoSmithKline). Another combination adjuvant formulation includes 3D-MPL and an aluminum salt, such as aluminum hydroxide (such as AS04 (GlaxoSmithKline). When formulated in combination, this combination can enhance an antigen-specific Th1 immune response.

In some instances, the adjuvant formulation a mineral salt, such as a calcium or aluminum (alum) salt, for example calcium phosphate, aluminum phosphate or aluminum hydroxide. In some embodiments, the adjuvant includes an oil and water emulsion, e.g., an oil-in-water emulsion (such as MF59 (Novartis) or AS03 (GlaxoSmithKline). One example of an oil-in-water emulsion comprises a metabolisable oil, such as squalene, a tocol such as a tocopherol, e.g., alpha-tocopherol, and a surfactant, such as sorbitan trioleate (SPAN® 85) or polyoxyethylene sorbitan monooleate (TWEEN®80), in an aqueous carrier.

In some embodiments, the subject has a tumor, and an amount is administered that reduces the tumor volume or load (as for example determined by imaging the tumor). Effective amounts may also be assessed by the presence and/or frequency of tumor cells in the blood or other body fluid or tissue (e.g., a biopsy). If the tumor is impacting the normal functioning of a tissue or organ, then the effective amount may be assessed by measuring the normal functioning of the tissue or organ. The particle construct can reduce tumor volume, and/or decrease metastasis.

In some embodiments, a therapeutically effective amount is the amount required to lessen or eliminate one or more, and preferably all, symptoms. For example, in a subject having an allergy or experiencing an asthmatic attack, an effective amount of an agent may be that amount that lessens or eliminates the symptoms associated with the allergy or the asthmatic attack. They may include sneezing, hives, nasal congestion, and labored breathing. Similarly, in a subject with an infection, an effective amount of an agent may be that amount that lessens or eliminate the symptoms associated with the infection. These may include fever and malaise.

The disclosed particle constructs can be used for imaging. Thus, in some embodiments, the agent of interest is a detectable marker. If the agent is a diagnostic agent, an effective amount may be an amount that allows visualization of the body region or cells of interest.

If the agent of interest is an antigen, the effective amount may be that amount that triggers an immune response against the antigen and preferably provides short and even more preferably long term protection against the pathogen from which the antigen derives.

The disclosed methods include a single administration of a particle construct, or multiple administrations. As an example, a particle construct can be administered in a prime dose and a boost dose.

For prophylactic and therapeutic purposes, the immunogenic composition including the particle construct can be administered to the subject in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the immunogenic composition can be provided as repeated doses within a prolonged prophylaxis or treatment regimen that will yield clinically significant results to alleviate one or more symptoms or detectable conditions associated with a targeted disease or condition as set forth herein. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, porcine, feline, ferret, non-human primate, and other accepted animal model subjects known in the art. Alternatively, effective dosages can be determined using in vitro models (for example, immunologic and histopathologic assays). Using such models, only ordinary calculations and adjustments are required to determine an appropriate concentration and dose to administer a therapeutically effective amount of the immunogenic composition (for example, amounts that are effective to elicit a desired immune response or alleviate one or more symptoms of a targeted disease). In alternative embodiments, an effective amount or effective dose of the immunogenic composition may simply inhibit or enhance one or more selected biological activities correlated with a disease or condition, as set forth herein, for either therapeutic or diagnostic purposes.

In one embodiment, a suitable immunization regimen includes at least three separate inoculations with one or more immunogenic compositions including a particle construct, with a second inoculation being administered more than about two, about three to eight, or about four, weeks following the first inoculation. Generally, the third inoculation is administered several months after the second inoculation, and in specific embodiments, more than about five months after the first inoculation, more than about six months to about two years after the first inoculation, or about eight months to about one year after the first inoculation. Periodic inoculations beyond the third are also desirable to enhance the subject's "immune memory." The adequacy of the vaccination parameters chosen, e.g., formulation, dose, regimen and the like, can be determined by taking aliquots of serum from the subject and assaying antibody titers during the course of the immunization program. If such monitoring indicates that vaccination is sub-optimal, the subject can be boosted with an additional dose of immunogenic composition, and the vaccination parameters can be modified in a fashion expected to potentiate the immune response. It is contemplated that there can be several boosts, and that each boost can include the same or a different particle construct.

For prime-boost protocols, the prime can be administered as a single dose or multiple doses, for example two doses, three doses, four doses, five doses, six doses or more can be administered to a subject over days, weeks or months. The boost can be administered as a single dose or multiple doses, for example two to six doses, or more can be administered to a subject over a day, a week or months. Multiple boosts can also be given, such one to five, or more. Different dosages can be used in a series of sequential inoculations.

For example a relatively large dose in a primary inoculation and then a boost with relatively smaller doses. The immune response against the selected antigenic surface can be generated by one or more inoculations of a subject with an immunogenic composition disclosed herein.

The actual dosage will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the particle construct for eliciting the desired activity or biological response in the subject. Dosage regimens can be adjusted to provide an optimum prophylactic or therapeutic response. As described above in the forgoing listing of terms, an effective amount is also one in which any toxic or detrimental side effects of the disclosed antigen and/or other biologically active agent is outweighed in clinical terms by therapeutically beneficial effects.

Thus pharmaceutical compositions are provided that include a therapeutically effective amount of a particle construct and a pharmaceutically acceptable carrier, such as a non-naturally occurring carrier. Exemplary non-limiting therapeutically effective doses of the particle construct are 0.01 to 10.0 µg/gm, such as 0.1 to 1.0 µg/gm. Additional exemplary therapeutically effective doses are 0.25 to 0.75 µg/gm such as 0.4 to 0.6 µg/gm. One of skill in the art can readily determine the absolute dose based on the weight of the subject, such as a human subject weighing from 50 kg to 100 kg, such as a 70 kg subject. Thus, for a 70 kg subject, 700 µg to 700 mg, 7 mg to 70 mg, 17.5 mg to 52.5 mg, or 28 mg to 42 mg, for example 35 mg, can be administered. In one non-limiting example, the particle construct includes a synthetic core of mesoporous silica.

In some embodiments, the pharmaceutical composition does not include an adjuvant. In specific non-limiting examples, the subject is not administered an adjuvant, either as part of the particle construct or separately.

In additional embodiments, the pharmaceutical can be administered as a prime of the immunogenic composition and a boost of the immunogenic composition.

In further embodiments, the pharmaceutical is formulated for intranasal administration. Thus, the method can include administering the therapeutically effective amount of the composition intra-nasally. In some examples, the pharmaceutical composition does not include an adjuvant. In additional examples, the subject is not administered an adjuvant, either as part of the particle construct or separately. In further examples, the pharmaceutical can be administered as a prime of the immunogenic composition and a boost of the immunogenic composition.

The components of the pharmaceutical compositions are commingled in a manner that precludes interaction that would substantially impair their desired pharmaceutical efficiency. Suitable buffering agents include acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); and parabens (0.01-0.25% w/v).

The disclosed particle constructs can be administered systemically or locally. The particular mode selected will depend, of course, upon the particular active agent selected, the particular condition being treated and the dosage required for therapeutic efficacy. Any mode of administration can be utilized that is medically acceptable, such that the desired response is induced without causing clinically unacceptable adverse effects. One mode of administration is a parenteral route. The term "parenteral" includes subcutaneous injections, intravenous, intramuscular, intraperitoneal, intra sternal injection or infusion techniques. Other modes of administration include oral, mucosal, rectal, vaginal, sublingual, intranasal, intratracheal, inhalation, ocular, and transdermal. Additional modes of administration are to a mucosa, such as nasal, vaginal or rectal administration.

The disclosed particle constructs can be formulated for oral administration. Such carriers enable formulation as tablets, pills, dragees, capsules, liquids, gels, syrups, slurries, films, suspensions and the like, for oral ingestion by a subject to be treated. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). Optionally the oral formulations may also be formulated in saline or buffers for neutralizing internal acid conditions or may be administered without any carriers. These compositions include capsules made of gelatin, as well as soft, sealed capsules made of gelatin and a plasticizer, such as glycerol or sorbitol. The capsules can contain the disclosed particle constructs suspended in suitable liquids, such as aqueous solutions, buffered solutions, fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner. For intranasal administration, the compositions can be used in intranasal drops, aerosols, and mists, and employ a protocol or device adapted to this delivery. An applicable method for direct delivery upper third of the nasal cavity is intranasal intubation. Applicable delivery methods include aerosols, power aerosols, spray aerosols, metered spray and suspension spays, see PCT Application No. 2008/016729, incorporated herein by reference. For administration by inhalation, the particle constructs can be delivered in the form of an aerosol spray presentation from pressurized packs or a nebulizer, with the use of a suitable propellant, such as dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount.

When it is desirable to deliver the compositions of the invention systemically, they may be formulated for parenteral administration by injection, e.g., by bolus injection or continuous infusion. Formulations for injection may be presented in unit dosage form, e.g., in ampoules or in multi-dose containers. Pharmaceutical parenteral formulations include aqueous solutions of the ingredients. Aqueous injection suspensions may contain substances which increase the viscosity of the suspension, such as sodium carboxymethyl cellulose, sorbitol, or dextran. Alternatively, suspensions of particles may be prepared as oil-based suspensions. Suitable lipophilic solvents or vehicles include fatty oils such as sesame oil, or synthetic fatty acid esters, such as ethyl oleate or triglycerides.

The disclosed particle construct also may be in powder form or lyophilized form for constitution with a suitable vehicle, e.g., sterile pyrogen-free water, before use. The compositions may also be formulated in rectal or vaginal compositions such as suppositories or retention enemas, for example containing conventional suppository bases such as cocoa butter or other glycerides.

Kits can also be produced that include the particle constructs. The particle constructs may be supplied in a container in the kit, and optionally the kit can include one or more antigens, adjuvants, or other therapeutic agents. In some embodiments, the kit does not include an adjuvant. The particle constructs can be supplied in various forms depending on the type of functionalized lipid bilayer component, on the type of adjuvant, on the type of core polymer, and the type of agent included in the construct. The particles may be provided in a buffer or in a lyophilized form. In several embodiments the container may have a sterile access port (for example the container may be an intravenous solution bag or a vial having a stopper pierceable by a hypodermic injection needle). The kit can include a means for mucosal administration, such as a spray bottle or device for intranasal administration. Instructions for use, in written form or on a computer-readable medium, also can be included in the kit. The label or package insert can indicate that the composition is used for treating the particular condition. The package insert typically includes instructions customarily included in commercial packages of therapeutic products that contain information about the indications, usage, dosage, administration, contraindications and/or warnings concerning the use of such therapeutic products. The kits may also include additional components to facilitate the particular application for which the kit is designed. For example, the kits may additionally include buffers and other reagents routinely used for the practice of a particular method. The kit may include several doses, such as suitable for use in a prime boost strategy.

Environmental Use

The disclosed particle constructs can include an enzyme, wherein the enzyme is a bioremediation enzyme that metabolizes an environmental pollutant. In some embodiments, the enzyme is laccase, a hydrolase, a dehalogenase, a transferase, or an oxidoreductase, a lyase, and isomerase, or a ligase. In yet other embodiments, the enzyme is a phosphotriesterase, an amidase, a protease, a carbohydrase, a cellulase, an amylase, a depolymerase, a lipase, a monooxygenase, a di-oxygenase, a reductase, a cytochrome P450 monooxygenase, a phenoloxidase, or a peroxidase. In specific non-limiting examples, the enzyme is a peroxidase, such as lignin peroxidase (LiP), manganese-dependant peroxidase (MnP), or versatile peroxidase (VP).

Thus, methods are provided herein for degrading an environmental pollutant from an environment, wherein the method includes introducing into the environment an effective amount of the particle construct to degrade the environmental pollutant.

The environment can includes at least one of water, soil, food product, or air or other gas. In some embodiments, the environment includes ground water, surface water, effluent, or wastewater. In additional embodiments, the water includes at least one of a lake, river, stream, sludge, slurry, sewage, ocean, fountain, or other water. In yet other embodiments, the environment includes water contained in an at least partially enclosed space (e.g., septic tank, lagoon, dam, wastewater treatment vessel, etc.).

In some embodiments, the agent of interest degrades or converts at least one hydrocarbon source. For example, alkanes, alkenes, alkynes, polyalkenes, polyalkynes, chlorinated, volatile, or aliphatic hydrocarbons are common contaminants in soil, or ground water. Such hydrocarbons are a common constituent in solvents, degreasers, and other compounds. Other non-limiting examples of hydrocarbon compounds include chlorinated aliphatic hydrocarbons, chlorinated aromatic hydrocarbons, or non-chlorinated aromatic hydrocarbons. Non-limiting examples of hydrocarbon contaminants or other contaminants that can be degraded include methylene chloride, 1,1-dichloroethane, chloroform, 1,2-dichloropropane, dibromochloromethane, 1,1,2-trichloroethane, 2-chloroethylvinyl ether, tetrachloroethene (PCE), chlorobenzene, 1,2-dichloroethane, 1,1,1-trichloroethane, bromodichloromethane, trans-1,3-dichloropropene, cis-1,3-dichloropropene, bromoform, benzene, toluene, ethylbenzene, xylenes, chloromethane, bromomethane, vinyl chloride, chloroethane, 1,1-dichloroethene, trans-1,2-dichloroethene, trichloroethene (TCE), dichlorobenzenes, cis-1,2-dichloroethene, dibromomethane, 1,4-dichlorobutane, 1,2,3-trichloropropane, bromochloromethane, 2,2-dichloropropane, 1,2-dibromoethane, 1,3-dichloropropane, bromobenzene, chlorotoluenes, trichlorobenzenes, trimethylbenzenes, trans-1,4-dichloro-2-butene, butylbenzenes, methyl tertiary butyl ether, polychlorinated biphenyl, or polycyclic aromatic hydrocarbon.

In another example, the enzyme degrades nitrogen-based aromatic compounds, pesticides, esters, ethers, aldehydes, amines, dioxins, herbicides, ketones, phenols, alcohols, sulfur-containing compounds, ethylene dibromide, chlorophenolic compounds, chlorate, cyanide, halogenated compounds, radioactive compounds, or other contaminants.

Bioremediation of an environmental medium, such as removing contaminant hydrocarbons or other substances from an environment, can be performed by inducing a particle construct directly into the environmental medium directly or by introduction to batches of contaminated components of the environment (such as soil or water) in an at least partially enclosed space (e.g., a bioreactor). In some examples, at least a partial vacuum is maintained within the substrate to be treated in order to confine the hydrocarbon source. In additional examples, a venting system provides additional oxygenation for degradation.

Methods are provided for degrading persistent organic pollutants (POPs) present in soils and sediments and wastewater. The methods include exposing contaminated soil or sediment or wastewater to a particle construct. This extraction also can be extended using methods such as solid liquid phase extraction and/or washing.

An exemplary in-situ method of degrading POPs present in soils or sediments or wastewater, includes (a) pretreating the soil or sediment or wastewater with acidic or base extraction method by means of a delivery system (i.e., vertical well field, horizontal well field or injection gallery; (b) exposing the soil or sediment or wastewater to a particle construct that includes an enzyme that can degrade aromatic hydrocarbons; (c) monitoring the degradation of the POPs.

The disclosure is illustrated by the following non-limiting Examples.

EXAMPLES

The spore coat of *Bacillus* has resisted detailed biochemical analysis due to its complexity, and the high levels of cross-linking between the proteins that comprise it have made extraction of individual coat proteins historically difficult. During sporulation, the rod-shaped bacterium elaborates a spherical inner cell called the forespore, which will eventually become the mature spore. Approximately seventy different proteins are produced in the outer cell and are deposited on the surface of the forespore to form the "coat," a hardy structure which is the outermost layer of the *B. subtilis* spore, which protects the mature spore from environmental insults. Coat morphogenesis initiates with the assembly of a basement layer, a platform on top of which the other coat proteins deposit.

The structural component of the basement layer is composed of SpoIVA, an exceptional cytoskeletal protein that hydrolyzes ATP to drive its irreversible polymerization. SpoIVA is anchored to the surface of the forespore by SpoVM, a small amphipathic α-helical protein that localizes properly by sensing the positive membrane curvature of the forespore surface. It is disclosed herein that these two spore coat components can be used with spherical supported lipid bilayers to form artificial spore-like particles. The stable assembly of the basement layer of the coat requires the anchoring protein SpoVM and SpoIVA. These spore-like particles can be covalently and specifically decorated with small molecules and proteins of interest. Thus, particle constructs can be produced that are versatile display platforms for drugs and vaccines in clinical settings, or for enzymes that neutralize pollutants for environmental remediation Example 1

Methods

Strain Construction:

All *B. subtilis* strains are isogeneic derivatives of PY79[45]. Strains KR160 (thrC::gfp-spoIVA spec), KR178 (AspoVM:: tetR thrC::gfp-spoIVA spec), and KR394 (thrC::gfp-spoIVA$^{K30A}$ spec), and construction of His-tagged SpoIVA$^{K30A}$ have been described Ramamurthi and Losick, *Mol Cell* 31, 406-414 (2008) and Ramamurthi et al., *Mol Microbiol* 62, 1547-1557 (2006)). A His6-tagged cysteineless SpoIVA variant (C98S was substituted with Ser because it occurs at this position in other SpoIVA orthologs) (Castaing et al., *Proc Natl Acad Sci USA* 110, E151-160 (2013)) with an extra cysteine engineered into the N-terminus was constructed by the QUIKCHANGE® Lightning Site-Directed Mutagenesis kit (Agilent) using plasmid pKR145$^{t2}$ as the template to produce plasmid pJP120. Plasmid pIL3, encoding superfolder GFP (sfGFP) for purification was PCR amplified from pBAD24-sfGFPX1 (Malagon, *RNA* 19, 1200-1207 (2013)) and cloned into pET28a (Novagen) using NheI and HindIII restriction sites. Surface exposed cysteine (S147C) (Nathani et al., *Chembiochem* 13, 1283-1285 (2012)) was introduced into sfGFP by site-directed mutagenesis using pIL3 as a template to generate pIL4.

Protein Purification and Labeling:

SpoIVA and sfGFP variants were overproduced in *E. coli* BL21(DE3) and purified using Ni$^{2+}$ affinity chromatography (Qiagen) (Castaing et al., *Proc Natl Acad Sci USA* 110, E151-160 (2013)). SpoIVA was additionally purified by ion-exchange chromatography (MonoQ; Pharmacia) (Castaing et al., *Proc Natl Acad Sci USA* 110, E151-160 (2013)). SpoIVA was labeled with ALEXA FLUOR® 488 C5-maleimide (Life Technologies) following the manufacturer's protocol. For click chemistry conjugation, SpoIVA and sfGFP were labeled with Trans-Cyclooctene-PEG$_3$-Maleimide, Azido-PEG$_3$-Maleimide Kit, or DBCO-PEG$_4$-Maleimide as described by the manufacturer (Click Chemistry Tools). Briefly, 20-fold molar excess of maleimide reagent was added to the protein samples and incubated for overnight at 4° C. and the excess reagent was removed by PD-10 desalting column (GE Healthcare).

SSLB Preparation:

SSLBs were made largely as described (Bayerl and Bloom, *Biophys J* 58, 357-362 (1990) and Gopalakrishnan and Rouiller, *Langmuir* 25, 5455-5458 (2009)). Briefly, liposomes were produced by the sonication method using 100 μl (10 mg/mL) *E. coli* polar lipid extract (Avanti) that were first evaporated under vacuum overnight at room temperature and hydrated in 1 mL ultrapure water. Resuspended lipids were subjected to five freeze-thaw cycles between methanol-dry ice bath and 42° C. water bath, followed by sonication until the suspension became transparent. Debris was removed by centrifugation at 13,000×g for 10 minutes and the supernatant containing unilamellar vesicles was retained. Silica beads (2 μm, 10 mg/mL) (PolySciences, Inc.) were prepared for coating by washing three times each in 1 mL ultrapure water, followed by methanol, and 1M NaOH. The beads were rinsed and resuspended in 200 μL ultrapure water. The SSLBs were constructed by mixing the silica beads with 200 μL prepared liposomes and 1 mM CaCl$_2$, and incubated at 42° C. for 30 minutes. After vortexing, SSLBs were collected by centrifugation at 13,000×g for 1 minute, washed three times with ultrapure water, and resuspended in 1 mL buffer A (50 mM Tris and 400 mM NaCl at pH7.5).

SSHEL Particle Construction:

SpoVM was synthesized as 26 amino acid peptide (Biomatik Corp.) and incubated at 10 μM (final concentration) with 2.5 mg/mL 2 μm-diameter SSLBs in buffer A, overnight at 25° C. following a program of alternate shaking and resting every 5 minutes. SpoVM-coated SSLBs were collected by centrifugation at 13,000×g for 1 minute, and then were incubated with varying concentrations of SpoIVA$^{AF488}$ in a final volume of 100 μL buffer A containing 10 mM MgCl$_2$ and 4 mM ATP, overnight at room temperature with gentle inversion. SSHEL particles were collected by centrifugation and resuspended in 100 μL buffer A for microscopy. For competition assays, SpoVM-SSLBs were incubated with 0.006 μM SpoIVA$^{A488}$ in the presence or absence of 4 mM ATP in buffer A containing 10 mM MgCl$_2$. The fluorescent SSLBs were collected by centrifugation, and resuspended with 100 μL buffer A containing 5 μM unlabeled SpoIVA. 5 μL aliquots were taken at indicated time points for microscopy.

Epifluorescence Microscopy:

Overnight cultures of *B. subtilis* harboring GFP-SpoIVA and variants were induced to sporulate by the resuspension method (Sterlini and Mandelstam, *Biochem J* 113, 29-37 (1969)) in medium containing 1 ug mL$^{-1}$ of the fluorescent membrane dye FM4-64 (Life Technologies). Cells were harvested and prepared for microscopy using an 1% agarose pad made with distilled water and viewed with a DeltaVision Core microscope system (Applied Precision) (Eswaramoorthy et al., *PLoS Genet* 10, e1004526 (2014)). Images were captured with a Photometrics Coolsnap HQ2 camera and deconvolved using SoftWorx software (Applied Precision). ImageJ was used to quantify the fluorescence located in the cells and forespores. For microscopy of SSLBs, 5 μL suspensions were placed on a glass bottom culture dish (Mattek Corp.) and covered by the agarose pad as described above. Thirty planes were acquired every 0.2 μm at room temperature; the data were deconvolved using SoftWorx software. The fluorescence intensities were then projected onto a single plane, quantified using SoftWorx software, and reported as fluorescence micron$^{-2}$ of SSLB surface area.

Scanning Electron Microscopy:

SSHEL particles were washed with PBS and fixed in 4% formaldehyde, 2% glutaraldehyde in 0.1M cacodylate buffer and post fixed using a 1% osmium tetroxide solution. They were then dehydrated in a series of graded alcohols and air dried after a final dehydration course of tetramethylsilane. The samples were subsequently coated with a thin layer of Au/Pd using an EMITECH K575X high resolution sputter coater set at 5 mA deposition current and imaged in a Zeiss NVision40 at a working distance of 5.0-8.2 mm; the SEM was operated at 3 keV landing energy, and secondary electrons were recorded at the SE2 detector. The images were acquired with a fast dwell time of 50 ns with 10× line averaging, and at a pixel sampling of 5 nm.

Surface Modification of SSHEL Particles:

Clickable SSHEL particles were constructed by incubating SpoVM-SSLBs with 0.2 μM SpoIVA$^{TCO}$ or SpoIVA$^{Azido}$ as described above. SSHEL particles were collected by centrifugation and resuspended in click buffer (50 mM Tris, 150 mM NaCl at pH7.5) containing 1 μM Cy3-Tetrazine or Cy5-DBCO (Click Chemistry Tools), inverting at room temperature for 2 hours. Dye-coupled SSHEL particles were collected by centrifugation, washed, and resuspended in click buffer, and a 5 μL aliquot was taken for microscopy. For stepwise ligation, SSHEL particles were constructed with 0.1 μM SpoIVA$^{TCO}$ and 0.1 μM SpoIVA$^{Azido}$ as described above, collected and resuspended in click buffer with 0.5 μM Cy3-Tetrazine, and incubated as described above. Cy3-SSHEL particles were collected and resuspended in click buffer containing 0.5 μM Cy5-DBCO and incubated similarly. The dual-fluorescent SSHELs were collected, washed and resuspended in click buffer for microscopy. To incorporate sfGFP onto SSHEL particles, 0.3 μM sfGFP$^{DBCO}$ was added into SpoIVA$^{Azido}$-SSHEL particles in click buffer containing 1 mM TCEP (Sigma) to prevent non-specific binding and incubated at room temperature for one hour. The sfGFP coupled-SSHEL particles were collected and resuspended with click buffer inverting at room temperature for one hour to wash off non-specific binding. The particles were then collected by centrifugation and resuspended in click buffer for microscopy.

Example 2

SpoVM is Necessary and Sufficient to Anchor SpoIVA

Proper localization of SpoIVA in vivo depends on SpoVM (Price and Losick, *J Bacteriol* 181, 781-790 (1999)). In a current model of spore coat basement layer assembly, the hydrophobic SpoVM spontaneously inserts preferentially into convex membranes to mark the forespore surface as the site for coat assembly (Ramamurthi, *Curr Opin Microbiol* 13, 753-757 (2010)), whereupon at least one residue in the N-terminus of SpoVM directly interacts with a C-terminal SpoIVA residue to recruit and anchor SpoIVA to the surface of the developing forespore (Ramamurthi et al., *Mol Microbiol* 62, 1547-1557 (2006)). Consistent with this model, in wild type cells GFP-SpoIVA localized uniformly around the forespore in vivo in those cells that had completed engulfment, and as arcs in those cells undergoing engulfment (FIG. 1B) (Price and Losick, *J Bacteriol* 181, 781-790 (1999)). In contrast, in the absence of SpoVM, GFP-SpoIVA localized instead as a single focus near the mother cell-proximal face of the forespore and failed to encase the forespore (Ramamurthi et al., *Mol Microbiol* 62, 1547-1557 (2006) and Price and Losick, *J Bacteriol* 181, 781-790 (1999)) (FIG. 1b).

Figure 1E:
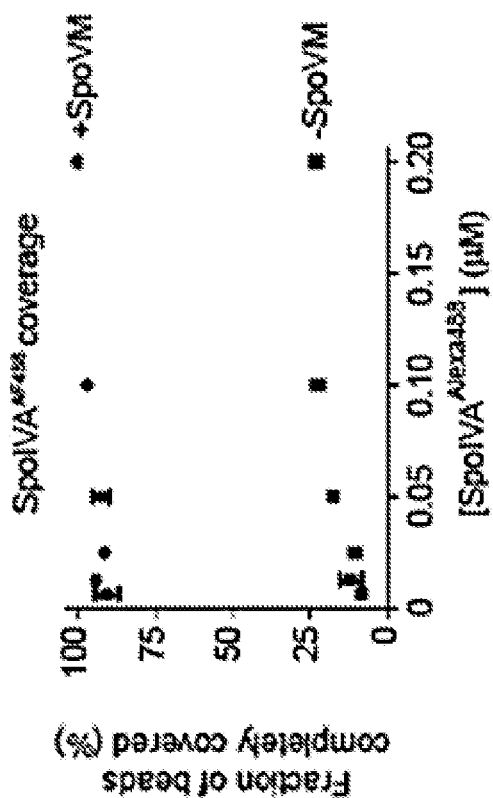

To test this model of basement layer assembly in vitro, spherical supported lipid bilayers (SSLBs) were constructed by coating 2 μm-diameter silica beads with a phospholipid bilayer (Bayerl and Bloom, *Biophys J* 58, 357-362 (1990) and Gopalakrishnan and Rouiller, *Langmuir* 25, 5455-5458 (2009)) to mimic the surface of the forespore. Next, SpoVM peptide was synthesized and was adsorbed to the SSLBs at concentrations that saturated the surface of the SSLBs. A cysteine-less variant of SpoIVA was produced that harbored a single engineered cysteine at the N-terminus, which was modified with the fluorescent dye ALEXA FLUOR® 488. *B. subtilis* cells producing this cysteine-less variant of SpoIVA as the only version of SpoIVA sporulated at 109±15% (s.d.; n=3) efficiency relative to wild type, indicating that it was largely functional in vivo. The SpoVM-coated SSLBs were then incubated with increasing concentrations of SpoIVA$^{AF488}$ and measured its adsorption using fluorescence microscopy (FIG. 1C). At the lowest concentration of SpoIVA$^{AF488}$ that was tested, some beads displayed obvious qualitative fluorescence that was distributed roughly uniformly around the SSLBs (FIG. 1c, arrow) whereas others displayed little or no fluorescence (FIG. 1C, arrowheads). At higher concentrations of SpoIVA$^{AF488}$ the heterogeneity in fluorescence between SSLBs was reduced and SpoIVA$^{AF488}$ adsorption approached saturation (FIG. 1C, 1E). In the absence of SpoVM, increasing concentrations of SpoIVA$^{AF488}$ again resulted in increasing fluorescence intensity on the SSLBs (FIG. 1E), but the pattern of adsorption was markedly different. Rather than uniform coating of SSLBs, SpoIVA$^{AF488}$ localized as patches on the SSLB surfaces (FIG. 1D) in a manner that was reminiscent of the distribution of GFP-SpoIVA in vivo on the surface of the forespore in the absence of SpoVM (FIG. 1B).

Figure 1F:
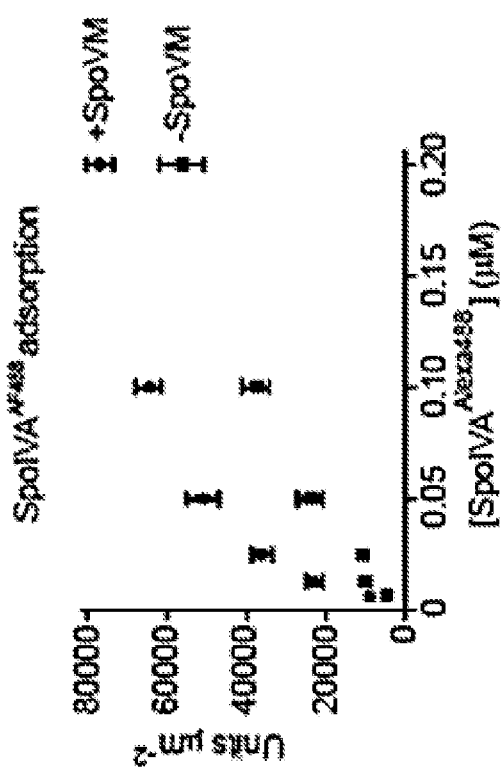

Quantification of distribution patterns of SpoIVA$^{AF488}$ on multiple SSLBs in vitro in the presence and absence of SpoVM revealed that, while approximately 100% of SSLBs were qualitatively encased completely with SpoIVA$^{AF488}$ in the presence of SpoVM at all concentrations of SpoIVA$^{AF488}$ that were tested, less than 20% of SSLBs were encased even at the highest SpoIVA$^{AF488}$ concentration in the absence of SpoVM (FIG. 1F). It was concluded that SpoIVA likely has an intrinsic affinity for membranes that allows it to initially localize to the surface of the forespore in vivo and to the surface of SSLBs in vitro, but that uniform coverage of SpoIVA atop either surface requires the localization of SpoVM to uniformly tether it to the membrane. Further, the similarity in the patterns of SpoIVA adsorption observed in vivo and in vitro indicates that SpoVM is sufficient for anchoring and uniformly distributing SpoIVA around a spherical membrane surface such as the forespore.

Example 3

Stable Association of SpoIVA with the Forespore Requires ATP

Figure 2C:
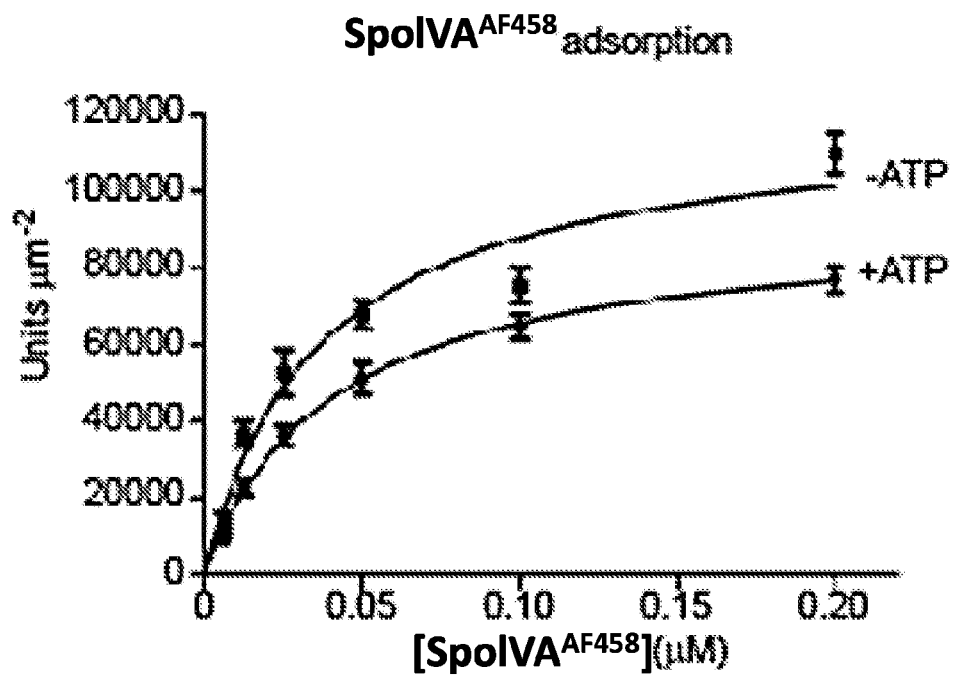
Figure 2D:
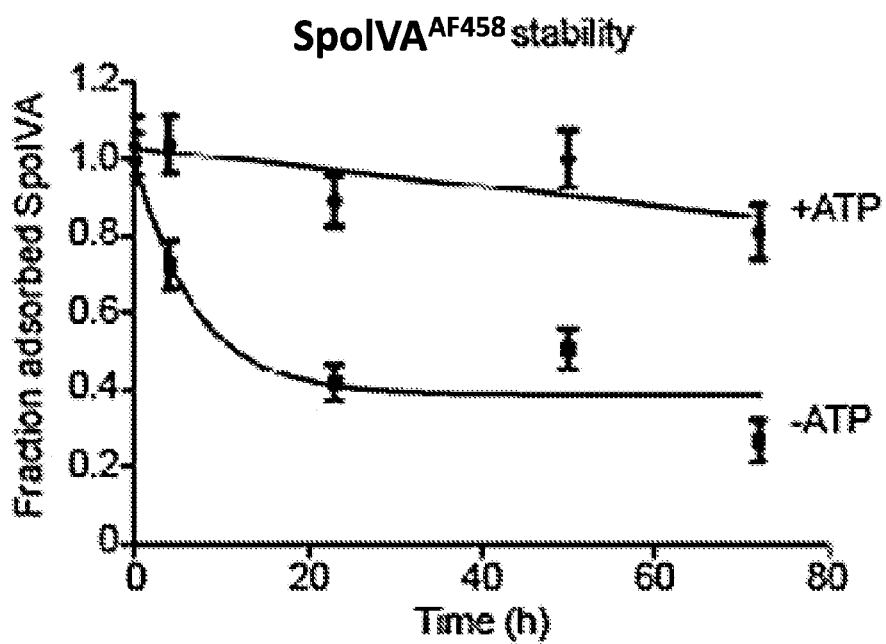

Unlike dynamic cytoskeleton proteins (Pollard and Cooper, *Science* 326, 1208-1212 (2009) and Kueh and Mitchison *Science* 325, 960-963 (2009)) intermediate filaments (Koster et al., *Curr Opin Cell Biol* 32C, 82-91 (2015)), the static polymerization of SpoIVA requires both ATP binding and hydrolysis (Ramamurthi and Losick, *Mol Cell* 31, 406-414 (2008)), which drives a conformational change that places the protein in a polymerization-competent state (Castaing et al., *Proc Natl Acad Sci USA* 110, E151-160 (2013)). In vivo, GFP-SpoIVA$^{K30A}$, a variant that harbors a disruption in the Walker A motif that abrogates ATP binding, largely localized at the forespore surface, indicated by 71±0.6% (s.e.m.; n=50) of the total fluorescence intensity that was associated with the forespore (with 83% (n=115) of engulfed forespores completely encased with GFP-SpoIVA$^{K30A}$), compared with 93±0.6% (n=50) (with 92% of engulfed forespores completely encased with GFP-SpoIVA) for GFP-SpoIVA (FIG. 2a) (Ramamurthi and Losick, *Mol Cell* 31, 406-414 (2008)). However, the increased amount of cytosolic GFP-SpoIVA$^{K30A}$ (~29% of the total for SpoIVA$^{K30A}$ versus only ~7% for WT SpoIVA) suggested that, in the absence of polymerization, its association with the forespore may be reversible. To investigate the role of ATP in basement layer assembly, varying concentrations of SpoIVA$^{AF488}$ was incubated with SpoVM-coated SSLBs in the presence and absence of ATP and measured its adsorption. At all concentrations tested, SpoIVA$^{AF488}$ adsorption onto SSLBs was similar in the presence and absence of ATP (FIG. 2b-c), similar to the behavior of GFP-SpoIVA$^{K30A}$ in comparison to GFP-SpoIVA in vivo (FIG. 2a). To test if ATP could be required for the irreversible association of SpoIVA on the membrane, SpoIVA$^{AF488}$ was first absorbed on the surface of SpoVM-coated SSLBs in the presence or absence of ATP, added an 800-fold excess of unlabeled SpoIVA, then monitored the association of SpoIVA$^{AF488}$ with the SSLBs over time (FIG. 2d). The competition assay revealed that, in the presence of ATP, 81%±7% (n>35 SSLBs) of the initial amount of SpoIVA$^{AF488}$ remained adsorbed on the SSLBs even after 72 h, suggesting that polymerized SpoIVA formed a stable shell atop the beads. However, in the absence of ATP, the initially bound SpoIVA$^{AF488}$ was rapidly competed off from SSLBs and only 72%±6% (n>35 SSLBs) remained associated with the SSLBs after just 4 h; after 72 h, only 26%±5% (n>35 SSLBs) remained associated (FIG. 2d), indicating a dynamic exchange between surface-bound SpoIVA$^{AF488}$ and unlabeled SpoIVA in solution. Thus, the kinetic measurement performed in vitro demonstrating desorption of SpoIVA$^{AF488}$ in the absence of ATP, likely mimicked the incomplete association of GFP-SpoIVA$^{K30A}$ observed in vivo. It was concluded that after SpoVM tethers SpoIVA onto the membrane surface, SpoIVA polymerization, driven by ATP, ensures the static association of the spore coat basement layer on the forespore surface. The data are also consistent with a model (Castaing et al., *Proc Natl Acad Sci USA* 110, E151-160 (2013)) in which recruitment of SpoIVA by SpoVM increases the local concentration of SpoIVA at a membrane surface to exceed the threshold concentration for SpoIVA polymerization, thereby ensuring the preferential polymerization of SpoIVA on the forespore surface, and not elsewhere.

Example 4

Ultrastructure of SSHEL Particles

It was previously shown that SpoIVA polymerizes into filaments in solution in the presence of ATP (Ramamurthi and Losick, *Mol Cell* 31, 406-414 (2008) and Castaing et al., *Proc Natl Acad Sci USA* 110, E151-160 (2013)), but its detailed ultrastructure upon assembly on a two dimensional surface has not been reported. Additionally, although several recent studies have employed atomic force microscopy to visualize the different layers of the coat in cells of mutants arrested at particular stages of coat assembly (Plomp et al., *PLoS One* 9, e108560 (2014), Ghosh et al., *J Bacteriol* 190, 6741-6748 (2008), and Plomp et al., *Langmuir* 21, 10710-10716 (2005)), it has been difficult to identify which proteins make up which particular feature in the context of the milieu of proteins in the coat—a problem that is amplified when examining the basement layer that is buried under the other layers of the coat. Since the behavior of SpoIVA recruitment and stability in our in vitro system mimicked that of SpoIVA in vivo, the topography of SSHEL particles was examined by scanning electron microscopy (SEM) to understand the ultrastructure of the basement layer of the coat. In the absence of any proteins, the surfaces of SSLBs were largely smooth, displaying only characteristic shallow ridges formed by membranes when viewed by SEM (FIG. 3a, 3f). Addition of SpoVM alone did not significantly alter the surface of the SSLBs (FIG. 3b, 3g). However, upon addition of SpoVM and SpoIVA in the presence of ATP, the surface of the beads assumed a more rough appearance (FIG. 3c). Closer examination of these surfaces (FIG. 3h) revealed non-uniformly shaped protrusions that were spaced irregularly (FIG. 3h, arrows), which were qualitatively reminiscent of the "pitted" surface reported on the surface of mature mutant spores (spoIVD) examined by AFM that did not assemble outer layers of the coat (Plomp et al., *PLoS One* 9, e108560 (2014)). Interestingly, these surfaces also frequently displayed short filaments (FIG. 3c, 3h; arrowheads) that were reminiscent of SpoIVA filaments detected by transmission electron microscopy that formed in solution in the presence of ATP (Ramamurthi and Losick, *Mol Cell* 31, 406-414 (2008)). In contrast, the surface of SSLBs incubated with SpoVM and SpoIVA in the absence of ATP (FIG. 3d, i), or SSLBs incubated with SpoVM, SpoIVA$^{K30A}$, and ATP (FIG. 3e, 3j) did not display such features. Taken together, it can be concluded that the SSHEL particles that were constructed harbor a static polymerized protein shell that displays a qualitatively differently textured surface than one which simply contains adsorbed proteins.

Example 5

Covalent Decoration of SSHELs with Molecules of Interest

Bacterial spore surfaces have been reported to be modified with a variety of proteins, and the use of spores modified in this manner has been proposed as a display system for ligands of interest that may be used as vaccine display platforms and for drug delivery (Pan et al., *Biotechnol* 30, 610-612 (2012), Nguyen et al., *FEMS Microbiol Lett* 358, 202-208 (2014), Lian et al., *Curr Microbiol* 68, 463-471 (2014), and Sibley et al., *FEMS Microbiol Lett* 358, 170-179 (2014)), for the display of enzymes to neutralize environmental pollution (Knecht et al., *Anal Bioanal Chem* 400, 977-989 (2011) and Hinc et al., *Res Microbiol* 161, 757-764 (2010)), and to screen for novel binding partners (Lusvarghi et al., *Org Biomol Chem* 7, 1815-1820 (2009)). However, these techniques often rely on the use of genetically modified organisms and, since they are built upon a viable spore, contain thousands of extraneous factors that, depending on the situation, could potentially interfere with the function of a displayed molecule of interest. Since SpoVM and SpoIVA alone were able to assemble into a stable shell in vitro with a distinct morphology whose behavior mimicked the coat basement layer in vivo, experiments were performed to covalently link small molecules and proteins to the surface of SSHEL particles using copper-free click chemistry (McKay et al., *Chem Biol* 21, 1075-1101 (2014), and Jewett and Bertozzi *Chem Soc Rev* 39, 1272-1279 (2010)). To this end, SSHEL particles were first assembled using a cysteine-less variant of SpoIVA harboring a single engineered cysteine at the N-terminus that was modified with trans-cyclooctene (TCO), which could be selectively labeled by tetrazine (Selvaraj et al., *Curr Opin Chem Biol* 17, 753-760 (2013)). Incubation of tetrazine-labeled fluorescent dye Cy3 with SSHEL particles constructed with SpoIVA without modification by TCO did not result in appreciable fluorescence, but SSHEL particles decorated with TCO-modified SpoIVA were able to be decorated with Cy3$^{Tet}$ (FIG. 4a, b, j, k). Similarly, SSHEL particles constructed with SpoIVA modified with azide was specifically able to be conjugated with the fluorescent dye Cy5 modified with the cognate click molecule dibenzocyclooctynes (DBCO) (Liang et al., J Am Chem Soc 134, 17904-17907 (2012)) (FIG. 4c, d, l, m). To test if multiple molecules may be clicked onto the surface of SSHELs, SSHEL particles were first constructed with a mix of SpoIVA modified with either TCO or azide, and then incubated them stepwise with Cy3$^{Tet}$ and Cy5$^{DBCO}$. When viewed under different microscope filters to detect Cy3 and Cy5 fluorescence, the same SSHEL particles were labeled with both Cy3$^{Tet}$ and Cy5$^{DBCO}$ (FIG. 4e-g, n-p), each at roughly half the fluorescence intensity as SSHELs constructed with a single modified version of SpoIVA (FIG. 4b, d), indicating that SSHEL particles may display at least two different covalently attached molecules using this strategy. To test if a protein of interest may be similarly covalently linked to the surface of SSHELs, green fluorescent protein (GFP) was first conjugated with DBCO. Whereas SSHEL particles constructed with unmodified SpoIVA displayed minimal fluorescence, the fluorescence from SSHEL particles constructed with SpoIVA$^{Azido}$ was almost 9-fold higher, indicating that proteins of interest may be specifically and covalently coupled to the surface. Thus, SSHEL particles, composed of a minimal defined set of components, may be covalently decorated with a combination of small molecules and proteins of interest and may serve as an alternate display platform for spore-based vaccines, biocatalysts, or drug delivery.

Spore formation in Bacillus subtilis is an attractive model system to elucidate mechanisms that underlie morphogenesis. However, to reconstitute morphogenetic events in vitro is difficult due to the complexity of a living organism. It was demonstrated that the initiation of spore coat assembly can be recapitulated atop SSLBs with defined protein components to build SSHEL particles. This system can be used as a robust in vitro assay to study the morphogenesis of complex structures such as the spore coat and to test the specific proposed predictions concerning the network of protein-protein interactions in the spore coat (McKenney et al., Curr Biol 20, 934-938 (2010)) beyond the basement layer. In addition, SSHEL particles are a versatile display platforms that can be used for delivery of drugs, vaccines, enzymes that neutralize pollutants for environmental remediation, and any other molecule of interest.

Example 6

Mucosal Administration in an In Vivo Model

Figure 6:
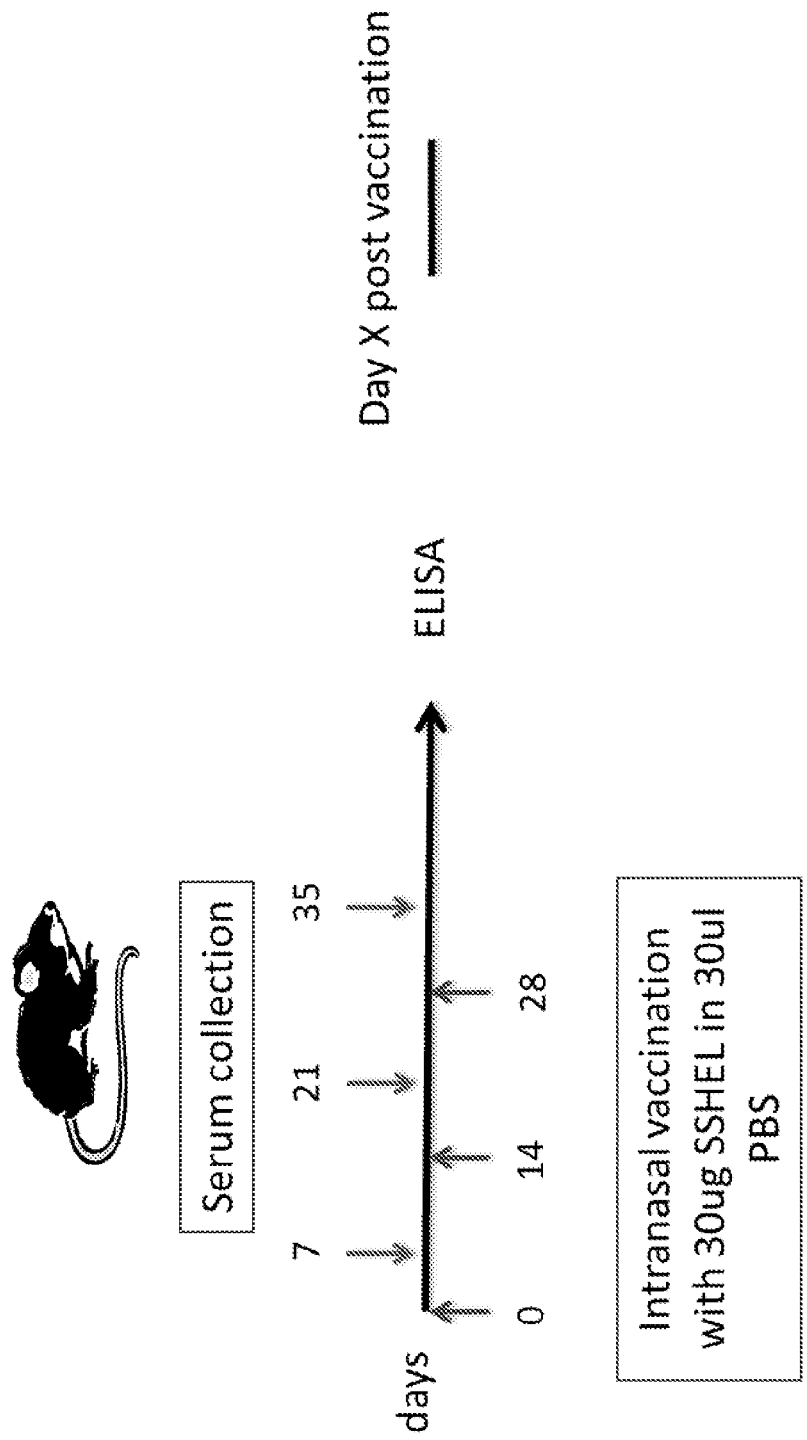
FIG. 6. Schematic diagram of a vaccination schedule. Mice were immunized 3 times, two-weeks apart, on days 0, 14 and 35. Serum samples were collected every other week and serum titers were assessed by ELISA. Plates were coated with 100 ng protein(s) without beads. Spleens (and lymphnodes) of mice are collected and re-stimulated with CD3/CD28 and with protein to assess type of T cell response by Flow Cytometry (e.g., CD4/CD8 and cytokine profile).

Mice were immunized via the nasal route (mucosal) three times, two-weeks apart on days 0, 14 and 35 with 30 micrograms of SSHEL particles (see FIG. 6) with 1) synthetic oligonucleotide CpG adjuvant, 2) Monophosphoryl Lipid A (MPL-A) adjuvant, or 3) no adjuvant. Serum samples were collected every other week and serum titers were assessed by ELISA using plates that were coated with 100 ng purified SpoIVA to assess antibody response to the surface protein exposed on the SSHEL particles.

Figure 7:
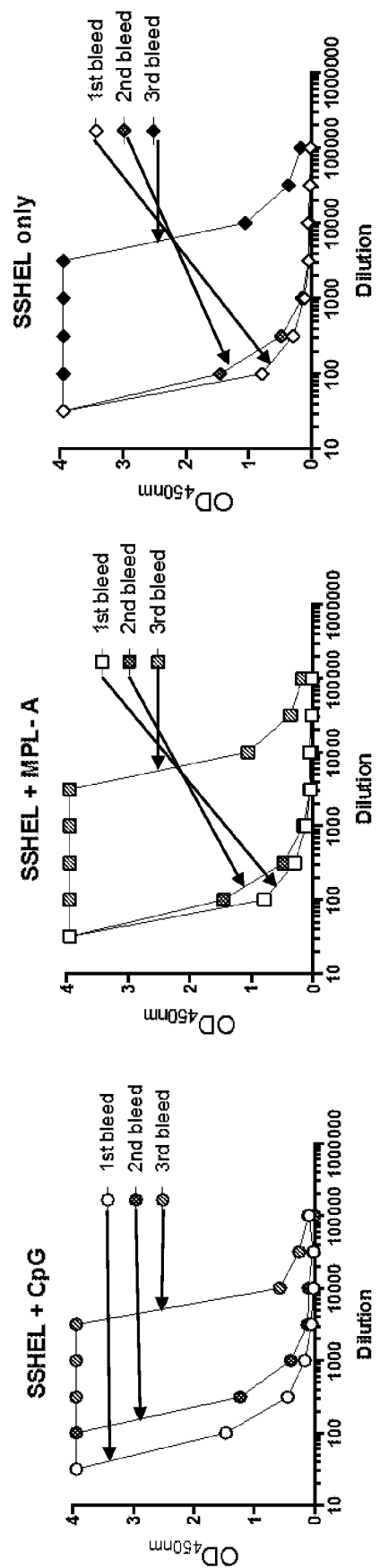
FIG. 7. Immunogenicity of SSHEL with and w/o adjuvants. SSHEL induced antibody response in the presence and absence of adjuvants. The third immunization elicited a robust antibody response. 1$^{st}$ bleed: serum antibody titers measured 7 days after 1$^{st}$ immunization. 2$^{nd}$ bleed: serum antibody titers measured 7 days after 2$^{nd}$ immunization. 3$^{rd}$ bleed: serum antibody titers measured 7 days after 3$^{rd}$ immunization

ELISAs performed with blood harvested after each immunization revealed that an equivalent antibody response was obtained from mice immunized with SSHELs along with either adjuvant. Surprisingly, an equivalent robust response was obtained when mice were immunized with SSHEL particles without any adjuvant at all (see FIG. 7). Without being bound by theory, these results are consistent with a model in which the highly concentrated, particulate nature of the SSHELs may elicit a strong immune response even without the need for stimulating the immune system with an adjuvant.

In further studies, an antigen (for example, ovalbumin) is conjugated to the surface of the SSHELs and the response is measure to confirm that a strong antibody response can be elicited to this protein without an adjuvant, and/or that a response to SpoIVA is elicited when the SSHEL surface is coated with ovalbumin.

In view of the many possible embodiments to which the principles of our invention may be applied, it should be recognized that illustrated embodiments are only examples of the invention and should not be considered a limitation on the scope of the invention. Rather, the scope of the invention is defined by the following claims. We therefore claim as our invention all that comes within the scope and spirit of these claims.

We claim:

1. A particle construct, comprising:
a synthetic core with a solid surface coated with a lipid bilayer;
SpoVM adhered to the lipid bilayer; and
SpoIVA adsorbed to the SpoVM, wherein
a) the SpoIVA has an N-terminus and a C-terminus, and wherein the SpoIVA comprises the amino acid sequence of one of:
   i) SEQ ID NOs: 1 or 12-28;
   ii) SEQ ID NOs: 1 or 12-28 without the N-terminal methionine;
   iii) SEQ ID NOs: 1 or 12-28 with a cysteine at the N-terminus;
   iv) SEQ ID NOs: 1 or 12-28 with a cysteine as the second residue following the methionine at the N-terminus; or
   v) SEQ ID NOs: 1 or 12-28 with a cysteine within 10 amino acids of the N-terminus, wherein the cysteine is exposed at a surface of the particle;
and wherein:
b) the SpoVM has an N-terminus and a C-terminus, and wherein the SpoVM comprises the amino acid sequence of one of:
   i) SEQ ID NOs: 2-11;
   ii) SEQ ID NOs: 2-11 without the N-terminal methionine;
   iii) SEQ ID NOs: 2-11 with a cysteine at the N-terminus;
   iv) SEQ ID NOs: 2-11 with a cysteine as the second residue following the methionine at the N-terminus; or
   v) SEQ ID NOs: 2-11 with a cysteine within 10 amino acids of the N-terminus, wherein the cysteine is exposed at a surface of the particle.

2. The particle construct of claim 1, wherein the SpoIVA comprises:
   i) one of SEQ ID NOs: 12-28;
   ii) one of SEQ ID NOs: 12-28 without the N-terminal methionine;
   iii) one of SEQ ID NOs: 12-28 with a cysteine at the N-terminus;
   iv) one of SEQ ID NOs: 12-28 with a cysteine as the second residue following the methionine at the N-terminus; or
   v) one of SEQ ID NOs: 12-28 with a cysteine within 10 amino acids of the N-terminus, wherein the cysteine is exposed at a surface of the particle.

3. The particle construct of claim 1, wherein the SpoIVA comprises
   SEQ ID NO: 1, without the N-terminal methionine;
   SEQ ID NO: 1 with a cysteine at the N-terminus;
   SEQ ID NO: 1 with a cysteine as the second residue following the methionine at the N-terminus; or
   SEQ ID NO: 1 with a cysteine within 10 amino acids of the N-terminus, wherein the cysteine is exposed at a surface of the particle.

4. The particle construct of claim 1, wherein the SpoIVA comprises the amino acid sequence set forth as SEQ ID NO: 1.

5. The particle construct of claim 1, wherein the SpoVM comprises:
   i) one of SEQ ID NOs: 3-11;
   ii) one of SEQ ID NOs: 3-11 without the N-terminal methionine;
   iii) one of SEQ ID NOs: 3-11 with a cysteine at the N-terminus;
   iv) one of SEQ ID NOs: 3-11 with a cysteine as the second residue following the methionine at the N-terminus; or
   v) one of SEQ ID NOs: 3-11 with a cysteine within 10 amino acids of the N-terminus, wherein the cysteine is exposed at a surface of the particle.

6. The particle construct of claim 1, wherein the SpoVM comprises
   SEQ ID NO: 2 without the N-terminal methionine;
   SEQ ID NO: 2 with a cysteine at the N-terminus;
   SEQ ID NO: 2 with a cysteine as the second residue following the methionine at the N-terminus;
   SEQ ID NO: 2 with a cysteine within 10 amino acids of the N-terminus; or
   the amino acid sequence set forth as SEQ ID NO: 2.

7. The particle construct of claim 1, further comprising an agent of interest covalently linked to the SpoIVA.

8. The particle construct of claim 3, further comprising an agent of interest covalently linked to the cysteine in SpoIVA.

9. The particle construct of claim 1, wherein the cysteine residue of the SpoIVA is modified with trans-cyclooctene, tetrazine, dibenzocyclooctyne (DBCO), or azide.

10. The particle construct of claim 7, wherein the agent of interest is an enzyme, a detectable marker, a pharmaceutical compound, an immunosuppressant or a vaccine.

11. The particle construct of claim 10, wherein the pharmaceutical compound is a chemotherapeutic agent, a radionucleotide, an analgesic, an anti-inflammatory agent, an anti-arrhythmic agent, an anti-coagulant, an anti-hypertensive agent, a lipid regulating agent, an anti-bacterial agent, an anti-viral agent, an anti-fungal agent, an anti-malarial agent, an anti-neoplastic agent, an immunosuppressant, an anti-protozoal agent, a psychotropic agent, a steroid, a diuretic, a histamine receptor antagonist, an anti-anginal agents, a nutritional compound, a protease inhibitor, a hormone, a stimulant, a muscle relaxant, a vaccine, an immunotoxin or an anti-osteoporosis agent.

12. The particle construct of claim 10, wherein the vaccine comprises an antigenic molecule.

13. The particle construct of claim 12, wherein the antigenic molecule is a viral, bacterial or fungal antigen.

14. The particle construct of claim 13, wherein the viral antigen is an antigen from a dengue virus, a human immunodeficiency virus, an influenza virus, a metapneumovirus, a norovirus, a papillomavirus, a parvovirus, a SARS virus, a smallpox virus, a picornaviruses, a respiratory syncitial virus, a parainfluenza virus, a measles virus, a hepatitis virus, an Ebola virus, a varicella zoster virus, a rabies virus or a West Nile virus.

15. The particle construct of claim 1, wherein the particle is a) less than one µm in diameter or b) 1-5 µm in diameter.

16. The particle construct of claim 1, wherein the particle is 100 nm to 8 µm in diameter.

17. The particle construct of claim 10, wherein the enzyme is a bioremediation enzyme that metabolizes an environmental pollutant.

18. The particle construct of claim 17, wherein the enzyme is laccase, a hydrolase, a dehalogenase, a transferase, or an oxidoreductase, a lyase, and isomerase, or a ligase.

19. The particle construct of claim 17, wherein the enzyme is a phosphotriesterase, an amidase, a protease, a carbohydrase, a cellulase, an amylase, a depolymerase, a lipase, a mono-oxygenase, a di-oxygenase, a reductase, a cytochrome P450 monoxygenase, a phenoloxidase, or a peroxidase.

20. The particle construct of claim 17, wherein the enzyme is a peroxidase, and wherein the enzyme is lignin peroxidase (LiP), manganese-dependant peroxidase (MnP), or versatile peroxidase (VP).

21. The particle construct of claim 1, wherein the synthetic core is silica, mesoporous silica, glass or a plastic resin.

22. The particle construct of claim 20, wherein the plastic resin is polystyrene, polypropylene, or polyethylene.

23. The particle construct of claim 1, wherein the synthetic core is a biodegradable polymer.

24. The particle construct of claim 23, wherein the biodegradable polymer is poly (D,L-lactide-co-glycolide) (PLGA), poly(ε-caprolactone) (PCL), or poly(lactic acid) (PLA).

25. The particle construct of claim 1, wherein the synthetic core is a metal core.

26. The particle construct of claim 25, wherein the metal core comprises magnetic iron, gold, or silver.

27. A composition comprising an effective amount of the particle construct of claim 1 and a carrier.

28. A method for producing a synthetic particle construct, comprising
   coating a synthetic core with a solid surface of about 0.1 to 100 µm diameter with a lipid bilayer to form a supported lipid bilayer;
   saturating the surface of the supported lipid bilayer with SpoVM, wherein the SpoVM has an N-terminus and a C-terminus, and wherein the SpoVM comprises the amino acid sequence of one of:
   i) SEQ ID NOs: 2-11;
   ii) SEQ ID NOs: 2-11 without the N-terminal methionine;
   iii) SEQ ID NOs: 2-11 with a cysteine at the N-terminus;
   iv) SEQ ID NOs: 2-11 with a cysteine as the second residue following the methionine at the N-terminus; or v) SEQ ID NOs: 2-11 with a cysteine within 10 amino acids of the N-terminus;
incubating the supported lipid bilayer with SpoIVA in the presence of adenosine triphosphate (ATP), wherein SpoIVA has an N-terminus and a C-terminus, and wherein the SpoIVA comprises the amino acid sequence of one of:
i) SEQ ID NOs: 1 or 12-28;
ii) SEQ ID NOs: 1 or 12-28 without the N-terminal methionine, or one of SEQ ID NOs: 12-28 without the N-terminal methionine;
iii) SEQ ID NOs: 1 or 12-28 with a cysteine at the N-terminus;
iv) SEQ ID NOs: 1 or 12-28 with a cysteine as the second residue following the methionine at the N-terminus; or
v) SEQ ID NOs: 1 or 12-28 with a cysteine within 10 amino acids of the N-terminus, wherein the cysteine is exposed at a surface of the particle,
thereby producing the particle.

29. A particle construct, comprising:
a synthetic core with a solid surface coated with a lipid bilayer;
SpoVM adhered to the lipid bilayer; and
SpoIVA adsorbed to the SpoVM, wherein:
a) the SpoIVA comprises the amino acid sequence of SEQ ID NO: 1 or SEQ ID NO: 1 without the N-terminal methionine; and
b) the SpoVM comprises the amino acid sequence of SEQ ID NO: 2 or SEQ ID NO: 2 without the N-terminal methionine.

30. A method for inducing an immune response to a bacterial antigen in a subject, comprising:
administering to the subject an effective amount of the particle construct of claim 29 covalently linked to an agent of interest, wherein the agent of interest is the bacterial antigen, thereby inducing the immune response to the bacterial antigen.

31. The method of claim 30, wherein the bacterial antigen is from a *Staphylococcus aureus*.

32. A method for treating a subject with breast cancer or ovarian cancer, comprising:
administering to the subject a therapeutically effective amount of the particle construct of claim 29 covalently linked to a chemotherapeutic agent, or an antibody specific to a tumor antigen expressed on the breast cancer cells or the ovarian cancer cells of the subject, thereby treating the breast cancer or the ovarian cancer in the subject.

33. The method of claim 32, wherein the chemotherapeutic agent is an antibody or doxorubicin.

34. The method of claim 32, wherein the method treats the ovarian cancer in the subject.

* * * * *

SEQUENCE LISTING

```
<160> NUMBER OF SEQ ID NOS: 28

<210> SEQ ID NO 1
<211> LENGTH: 516
<212> TYPE: PRT
<213> ORGANISM: Bacillus subtilis

<400> SEQUENCE: 1

Met Cys Gly Ser Ser His His His His His His Ser Ser Gly Leu Val
1               5                   10                  15

Pro Arg Gly Ser His Met Ala Ser Met Glu Lys Val Asp Ile Phe Lys
            20                  25                  30

Asp Ile Ala Glu Arg Thr Gly Gly Asp Ile Tyr Leu Gly Val Val Gly
        35                  40                  45

Ala Val Arg Thr Gly Lys Ser Thr Phe Ile Lys Lys Phe Met Glu Leu
    50                  55                  60

Val Val Leu Pro Asn Ile Ser Asn Glu Ala Asp Arg Ala Arg Ala Gln
65                  70                  75                  80
```

-continued

```
Asp Glu Leu Pro Gln Ser Ala Ala Gly Lys Thr Ile Met Thr Thr Glu
                85                  90                  95

Pro Lys Phe Val Pro Asn Gln Ala Met Ser Val His Val Ser Asp Gly
            100                 105                 110

Leu Asp Val Asn Ile Arg Leu Val Asp Ser Val Gly Tyr Thr Val Pro
        115                 120                 125

Gly Ala Lys Gly Tyr Glu Asp Glu Asn Gly Pro Arg Met Ile Asn Thr
130                 135                 140

Pro Trp Tyr Glu Glu Pro Ile Pro Phe His Glu Ala Ala Glu Ile Gly
145                 150                 155                 160

Thr Arg Lys Val Ile Gln Glu His Ser Thr Ile Gly Val Val Ile Thr
                165                 170                 175

Thr Asp Gly Thr Ile Gly Asp Ile Ala Arg Ser Asp Tyr Ile Glu Ala
            180                 185                 190

Glu Glu Arg Val Ile Glu Glu Leu Lys Glu Val Gly Lys Pro Phe Ile
        195                 200                 205

Met Val Ile Asn Ser Val Arg Pro Tyr His Pro Glu Thr Glu Ala Met
    210                 215                 220

Arg Gln Asp Leu Ser Glu Lys Tyr Asp Ile Pro Val Leu Ala Met Ser
225                 230                 235                 240

Val Glu Ser Met Arg Glu Ser Asp Val Leu Ser Val Leu Arg Glu Ala
                245                 250                 255

Leu Tyr Glu Phe Pro Val Leu Glu Val Asn Val Asn Leu Pro Ser Trp
            260                 265                 270

Val Met Val Leu Lys Glu Asn His Trp Leu Arg Glu Ser Tyr Gln Glu
        275                 280                 285

Ser Val Lys Glu Thr Val Lys Asp Ile Lys Arg Leu Arg Asp Val Asp
    290                 295                 300

Arg Val Val Gly Gln Phe Ser Glu Phe Glu Phe Ile Glu Ser Ala Gly
305                 310                 315                 320

Leu Ala Gly Ile Glu Leu Gly Gln Gly Val Ala Glu Ile Asp Leu Tyr
                325                 330                 335

Ala Pro Asp His Leu Tyr Asp Gln Ile Leu Lys Glu Val Val Gly Val
            340                 345                 350

Glu Ile Arg Gly Arg Asp His Leu Leu Glu Leu Met Gln Asp Phe Ala
        355                 360                 365

His Ala Lys Thr Glu Tyr Asp Gln Val Ser Asp Ala Leu Lys Met Val
    370                 375                 380

Lys Gln Thr Gly Tyr Gly Ile Ala Ala Pro Ala Leu Ala Asp Met Ser
385                 390                 395                 400

Leu Asp Glu Pro Glu Ile Ile Arg Gln Gly Ser Arg Phe Gly Val Arg
                405                 410                 415

Leu Lys Ala Val Ala Pro Ser Ile His Met Ile Lys Val Asp Val Glu
            420                 425                 430

Ser Glu Phe Ala Pro Ile Ile Gly Thr Glu Lys Gln Ser Glu Glu Leu
        435                 440                 445

Val Arg Tyr Leu Met Gln Asp Phe Glu Asp Pro Leu Ser Ile Trp
    450                 455                 460

Asn Ser Asp Ile Phe Gly Arg Ser Leu Ser Ser Ile Val Arg Glu Gly
465                 470                 475                 480

Ile Gln Ala Lys Leu Ser Leu Met Pro Glu Asn Ala Arg Tyr Lys Leu
                485                 490                 495
```

```
Lys Glu Thr Leu Glu Arg Ile Ile Asn Glu Gly Ser Gly Gly Leu Ile
            500                 505                 510

Ala Ile Ile Leu
        515

<210> SEQ ID NO 2
<211> LENGTH: 26
<212> TYPE: PRT
<213> ORGANISM: Bacillus subtilis

<400> SEQUENCE: 2

Met Lys Phe Tyr Thr Ile Lys Leu Pro Lys Phe Leu Gly Gly Ile Val
1               5                   10                  15

Arg Ala Met Leu Gly Ser Phe Arg Lys Asp
            20                  25

<210> SEQ ID NO 3
<211> LENGTH: 26
<212> TYPE: PRT
<213> ORGANISM: Bacillus amyloliquefaciens

<400> SEQUENCE: 3

Met Lys Phe Tyr Thr Ile Lys Leu Pro Lys Phe Leu Gly Gly Ile Val
1               5                   10                  15

Arg Ala Met Leu Gly Ser Phe Arg Lys Glu
            20                  25

<210> SEQ ID NO 4
<211> LENGTH: 26
<212> TYPE: PRT
<213> ORGANISM: Bacillus fordii

<400> SEQUENCE: 4

Met Lys Phe Tyr Thr Ile Lys Leu Pro Arg Phe Leu Gly Gly Ile Val
1               5                   10                  15

Arg Ala Met Leu Gly Thr Phe Lys Lys Asp
            20                  25

<210> SEQ ID NO 5
<211> LENGTH: 25
<212> TYPE: PRT
<213> ORGANISM: Geobacillus stearothermophilus

<400> SEQUENCE: 5

Met Lys Phe Tyr Thr Ile Lys Leu Pro Lys Phe Leu Gly Gly Ile Val
1               5                   10                  15

Arg Ala Met Leu Asn Thr Phe Lys Lys
            20                  25

<210> SEQ ID NO 6
<211> LENGTH: 25
<212> TYPE: PRT
<213> ORGANISM: Tuberibacillus calidus

<400> SEQUENCE: 6

Met Lys Phe Tyr Thr Ile Lys Leu Pro Arg Phe Leu Gly Gly Phe Ile
1               5                   10                  15

Arg Ala Ile Leu Gly Ser Phe Lys Lys
            20                  25

<210> SEQ ID NO 7
<211> LENGTH: 25
```

-continued

```
<212> TYPE: PRT
<213> ORGANISM: Thalassobacillus devorans

<400> SEQUENCE: 7

Met Lys Phe Tyr Thr Ile Lys Leu Pro Lys Phe Ile Gly Gly Phe Val
1               5                   10                  15

Arg Ala Val Ile Gly Thr Phe Lys Lys
            20                  25

<210> SEQ ID NO 8
<211> LENGTH: 26
<212> TYPE: PRT
<213> ORGANISM: Paenibacillus pinihumi

<400> SEQUENCE: 8

Met Lys Phe Tyr Thr Ile Lys Leu Pro Lys Phe Leu Gly Gly Phe Val
1               5                   10                  15

Lys Ala Val Leu Asn Thr Phe Gln Lys Asn
            20                  25

<210> SEQ ID NO 9
<211> LENGTH: 26
<212> TYPE: PRT
<213> ORGANISM: Clostridium perfringens

<400> SEQUENCE: 9

Met Arg Ile Met Thr Ile Lys Leu Pro Lys Phe Leu Ala Lys Ile Val
1               5                   10                  15

Arg Met Phe Lys Gly Asn Lys Lys Ser Asp
            20                  25

<210> SEQ ID NO 10
<211> LENGTH: 24
<212> TYPE: PRT
<213> ORGANISM: Clostridium acetobutylicum

<400> SEQUENCE: 10

Met Lys Ile Val Ala Ile Lys Leu Pro Lys Phe Leu Ser Asn Ile Ile
1               5                   10                  15

Lys Phe Phe Phe Arg Lys Lys Ser
            20

<210> SEQ ID NO 11
<211> LENGTH: 24
<212> TYPE: PRT
<213> ORGANISM: Clostridium botulinum

<400> SEQUENCE: 11

Met Lys Ile Val Ala Ile Lys Leu Pro Lys Phe Leu Ser Asn Ile Ile
1               5                   10                  15

Lys Phe Phe Phe Arg Lys Lys Ser
            20

<210> SEQ ID NO 12
<211> LENGTH: 492
<212> TYPE: PRT
<213> ORGANISM: Bacillus subtilis

<400> SEQUENCE: 12

Met Glu Lys Val Asp Ile Phe Lys Asp Ile Ala Glu Arg Thr Gly Gly
1               5                   10                  15

Asp Ile Tyr Leu Gly Val Val Gly Ala Val Arg Thr Gly Lys Ser Thr
```

```
                        20                  25                  30
        Phe Ile Lys Lys Phe Met Glu Leu Val Val Leu Pro Asn Ile Ser Asn
                    35                  40                  45

Glu Ala Asp Arg Ala Arg Ala Gln Asp Glu Leu Pro Gln Ser Ala Ala
        50                  55                  60

Gly Lys Thr Ile Met Thr Thr Glu Pro Lys Phe Val Pro Asn Gln Ala
        65                  70                  75                  80

Met Ser Val His Val Ser Asp Gly Leu Asp Val Asn Ile Arg Leu Val
                        85                  90                  95

Asp Cys Val Gly Tyr Thr Val Pro Gly Ala Lys Gly Tyr Glu Asp Glu
                    100                 105                 110

Asn Gly Pro Arg Met Ile Asn Thr Pro Trp Tyr Glu Pro Ile Pro
                115                 120                 125

Phe His Glu Ala Ala Glu Ile Gly Thr Arg Lys Val Ile Gln Glu His
                130                 135                 140

Ser Thr Ile Gly Val Val Ile Thr Thr Asp Gly Thr Ile Gly Asp Ile
        145                 150                 155                 160

Ala Arg Ser Asp Tyr Ile Glu Ala Glu Glu Arg Val Ile Glu Glu Leu
                        165                 170                 175

Lys Glu Val Gly Lys Pro Phe Ile Met Val Ile Asn Ser Val Arg Pro
                    180                 185                 190

Tyr His Pro Glu Thr Glu Ala Met Arg Gln Asp Leu Ser Glu Lys Tyr
                    195                 200                 205

Asp Ile Pro Val Leu Ala Met Ser Val Glu Ser Met Arg Glu Ser Asp
                    210                 215                 220

Val Leu Ser Val Leu Arg Glu Ala Leu Tyr Glu Phe Pro Val Leu Glu
        225                 230                 235                 240

Val Asn Val Asn Leu Pro Ser Trp Val Met Val Leu Lys Glu Asn His
                        245                 250                 255

Trp Leu Arg Glu Ser Tyr Gln Glu Ser Val Lys Glu Thr Val Lys Asp
                    260                 265                 270

Ile Lys Arg Leu Arg Asp Val Asp Arg Val Val Gly Gln Phe Ser Glu
                    275                 280                 285

Phe Glu Phe Ile Glu Ser Ala Gly Leu Ala Gly Ile Glu Leu Gly Gln
                    290                 295                 300

Gly Val Ala Glu Ile Asp Leu Tyr Ala Pro Asp His Leu Tyr Asp Gln
        305                 310                 315                 320

Ile Leu Lys Glu Val Val Gly Val Glu Ile Arg Gly Arg Asp His Leu
                        325                 330                 335

Leu Glu Leu Met Gln Asp Phe Ala His Ala Lys Thr Glu Tyr Asp Gln
                    340                 345                 350

Val Ser Asp Ala Leu Lys Met Val Lys Gln Thr Gly Tyr Gly Ile Ala
                    355                 360                 365

Ala Pro Ala Leu Ala Asp Met Ser Leu Asp Glu Pro Glu Ile Ile Arg
                    370                 375                 380

Gln Gly Ser Arg Phe Gly Val Arg Leu Lys Ala Val Ala Pro Ser Ile
        385                 390                 395                 400

His Met Ile Lys Val Asp Val Glu Ser Glu Phe Ala Pro Ile Ile Gly
                        405                 410                 415

Thr Glu Lys Gln Ser Glu Glu Leu Val Arg Tyr Leu Met Gln Asp Phe
                    420                 425                 430

Glu Asp Asp Pro Leu Ser Ile Trp Asn Ser Asp Ile Phe Gly Arg Ser
                    435                 440                 445
```

-continued

Leu Ser Ser Ile Val Arg Glu Gly Ile Gln Ala Lys Leu Ser Leu Met
    450                 455                 460

Pro Glu Asn Ala Arg Tyr Lys Leu Lys Glu Thr Leu Glu Arg Ile Ile
465                 470                 475                 480

Asn Glu Gly Ser Gly Gly Leu Ile Ala Ile Ile Leu
                485                 490

<210> SEQ ID NO 13
<211> LENGTH: 503
<212> TYPE: PRT
<213> ORGANISM: Bacillus amyloliquefaciens

<400> SEQUENCE: 13

Met Ile Arg Ile Gly Ser Pro Gly Gly Asp His Leu Glu Lys Val Asp
1               5                   10                  15

Ile Phe Lys Asp Ile Ala Glu Arg Thr Gly Gly Asp Ile Tyr Leu Gly
                20                  25                  30

Val Val Gly Ala Val Arg Thr Gly Lys Ser Thr Phe Ile Lys Lys Phe
            35                  40                  45

Met Glu Leu Val Val Leu Pro Asn Ile Ser Asn Glu Ala Asp Arg Ala
50                  55                  60

Arg Ala Gln Asp Glu Leu Pro Gln Ser Ala Ala Gly Lys Thr Ile Met
65                  70                  75                  80

Thr Thr Glu Pro Lys Phe Val Pro Asn Gln Ala Met Ser Val His Val
                85                  90                  95

Ala Glu Gly Leu Asp Val Asn Ile Arg Leu Val Asp Cys Val Gly Tyr
            100                 105                 110

Thr Val Pro Gly Ala Lys Gly Tyr Glu Asp Glu Asn Gly Pro Arg Met
        115                 120                 125

Ile Asn Thr Pro Trp Tyr Glu Glu Pro Ile Pro Phe His Glu Ala Ala
130                 135                 140

Glu Ile Gly Thr Arg Lys Val Ile Gln Glu His Ser Thr Ile Gly Val
145                 150                 155                 160

Val Ile Thr Thr Asp Gly Ser Ile Gly Asp Ile Ala Arg Gly Asp Tyr
                165                 170                 175

Val Glu Ala Glu Glu Arg Val Ile Asp Glu Leu Lys Glu Val Gly Lys
            180                 185                 190

Pro Phe Ile Met Val Ile Asn Ser Val Lys Pro Tyr His Pro Glu Thr
        195                 200                 205

Glu Ala Leu Arg Ala Glu Leu Ser Ala Lys Tyr Asp Ile Pro Val Leu
210                 215                 220

Ala Met Ser Val Glu Ser Met Arg Glu Thr Asp Val Leu Ser Val Leu
225                 230                 235                 240

Arg Glu Ala Leu Tyr Glu Phe Pro Val Leu Glu Val Asn Val Asn Leu
                245                 250                 255

Pro Ser Trp Val Met Val Leu Lys Glu Asn His Trp Leu Arg Glu Ser
            260                 265                 270

Tyr Gln Glu Ser Val Lys Glu Thr Val Lys Asp Ile Lys Arg Leu Arg
        275                 280                 285

Asp Val Asp Arg Val Val Gly His Phe Ser Glu Phe Glu Phe Ile Glu
290                 295                 300

Ser Ala Gly Leu Ala Gly Ile Glu Leu Gly Gln Gly Val Ala Glu Ile
305                 310                 315                 320

Asp Leu Tyr Ala Pro Asp His Leu Tyr Asp Gln Ile Leu Lys Glu Val

```
                325                 330                 335
Val Gly Val Glu Ile Arg Gly Lys Asp His Leu Leu Glu Leu Met Gln
            340                 345                 350

Asp Phe Ala His Ala Lys Lys Glu Tyr Asp Gln Val Ser Asp Ala Leu
            355                 360                 365

Lys Met Val Lys Gln Thr Gly Tyr Gly Ile Ala Ala Pro Ala Leu Ala
            370                 375                 380

Asp Met Ser Leu Asp Glu Pro Glu Ile Ile Arg Gln Gly Ser Arg Phe
385                 390                 395                 400

Gly Val Arg Leu Lys Ala Val Ala Pro Ser Ile His Met Ile Lys Val
                405                 410                 415

Asp Val Glu Ser Glu Phe Ala Pro Ile Ile Gly Thr Glu Lys Gln Ser
            420                 425                 430

Glu Glu Leu Val Arg Tyr Leu Met Gln Asp Phe Glu Asp Asp Pro Leu
            435                 440                 445

Ser Ile Trp Asn Ser Asp Ile Phe Gly Arg Ser Leu Ser Ser Ile Val
            450                 455                 460

Arg Glu Gly Ile Ser Ala Lys Leu Ser Leu Met Pro Glu Asn Ala Arg
465                 470                 475                 480

Tyr Lys Leu Lys Glu Thr Leu Glu Arg Ile Ile Asn Glu Gly Ser Gly
                485                 490                 495

Gly Leu Ile Ala Ile Ile Leu
            500

<210> SEQ ID NO 14
<211> LENGTH: 492
<212> TYPE: PRT
<213> ORGANISM: Bacillus licheniformis

<400> SEQUENCE: 14

Met Glu Lys Val Asp Ile Phe Lys Asp Ile Ala Glu Arg Thr Gly Gly
1               5                   10                  15

Asp Ile Tyr Leu Gly Val Val Gly Ala Val Arg Thr Gly Lys Ser Thr
            20                  25                  30

Phe Ile Lys Lys Phe Met Glu Leu Val Val Leu Pro Asn Ile Asn Asn
        35                  40                  45

Glu Ala Asp Arg Ala Arg Ala Gln Asp Glu Leu Pro Gln Ser Ala Ala
    50                  55                  60

Gly Lys Thr Ile Met Thr Thr Glu Pro Lys Phe Val Pro Asn Gln Ala
65                  70                  75                  80

Met Ser Val His Val Ser Asp Gly Leu Asp Val Asn Ile Arg Leu Val
                85                  90                  95

Asp Cys Val Gly Tyr Thr Val Pro Gly Ala Lys Gly Tyr Glu Asp Glu
            100                 105                 110

Asn Gly Pro Arg Met Ile Asn Thr Pro Trp Tyr Glu Glu Pro Ile Pro
        115                 120                 125

Phe His Glu Ala Ala Glu Ile Gly Thr Arg Lys Val Ile Gln Glu His
    130                 135                 140

Ser Thr Ile Gly Val Val Ile Thr Thr Asp Gly Thr Ile Gly Glu Ile
145                 150                 155                 160

Ala Arg Gln Asp Tyr Val Glu Ala Glu Glu Arg Val Ile Asp Glu Leu
                165                 170                 175

Lys Glu Val Gly Lys Pro Phe Ile Met Val Ile Asn Ser Val Arg Pro
            180                 185                 190
```

```
Tyr His Pro Glu Thr Glu Ala Leu Arg Gln Gly Leu Met Glu Lys Tyr
            195                 200                 205

Asp Ile Pro Val Leu Ala Met Ser Val Glu Ser Met Arg Glu Ala Asp
210                 215                 220

Val Leu Ser Val Leu Arg Glu Ala Leu Tyr Glu Phe Pro Val Leu Glu
225                 230                 235                 240

Val Asn Val Asn Leu Pro Ser Trp Val Met Val Leu Lys Glu Asn His
                245                 250                 255

Trp Leu Arg Glu Asn Tyr Gln Asp Ser Val Lys Glu Thr Val Lys Asp
            260                 265                 270

Ile Lys Arg Leu Arg Asp Val Asp Arg Val Val Gly His Phe Ser Glu
        275                 280                 285

Phe Asp Phe Ile Glu Arg Ala Ser Leu Ala Gly Ile Glu Met Gly Gln
    290                 295                 300

Gly Ile Ala Glu Ile Asp Leu Tyr Ala Pro Asp Tyr Leu Tyr Asp Glu
305                 310                 315                 320

Ile Leu Arg Glu Val Val Gly Val Glu Ile Arg Gly Lys Asp His Leu
                325                 330                 335

Leu Gln Leu Met Gln Asp Phe Ala His Ala Lys Thr Glu Tyr Asp Gln
            340                 345                 350

Val Ser Asp Ala Leu Lys Met Val Lys Gln Thr Gly Tyr Gly Ile Ala
        355                 360                 365

Ala Pro Ala Leu Thr Asp Met Ser Leu Asp Glu Pro Glu Ile Ile Arg
    370                 375                 380

Gln Gly Ser Arg Phe Gly Val Arg Leu Lys Ala Val Ala Pro Ser Ile
385                 390                 395                 400

His Met Ile Lys Val Asp Val Glu Ser Glu Phe Ala Pro Ile Ile Gly
                405                 410                 415

Thr Glu Lys Gln Ser Glu Gly Leu Val Arg Tyr Leu Met Gln Asp Phe
            420                 425                 430

Glu Asp Asp Pro Leu Ser Ile Trp Asn Ser Asp Ile Phe Gly Arg Ser
        435                 440                 445

Leu Ser Ser Ile Val Arg Glu Gly Ile Gln Ala Lys Leu Ser Leu Met
    450                 455                 460

Pro Glu Asn Ala Arg Tyr Lys Leu Lys Glu Thr Leu Glu Arg Ile Ile
465                 470                 475                 480

Asn Glu Gly Ser Gly Gly Leu Ile Ala Ile Ile Leu
                485                 490
```

<210> SEQ ID NO 15
<211> LENGTH: 492
<212> TYPE: PRT
<213> ORGANISM: Bacillus anthracis

<400> SEQUENCE: 15

```
Met Glu Lys Val Asp Ile Phe Lys Asp Ile Ala Glu Arg Thr Gly Gly
1               5                   10                  15

Asp Ile Tyr Phe Gly Val Val Gly Ala Val Arg Thr Gly Lys Ser Thr
            20                  25                  30

Phe Ile Lys Lys Phe Met Glu Leu Val Val Ile Pro Asn Ile Glu Asn
        35                  40                  45

Glu Ser Asp Arg Gln Arg Ala Gln Asp Glu Leu Pro Gln Ser Ala Ala
    50                  55                  60

Gly Arg Thr Ile Met Thr Thr Glu Pro Lys Phe Val Pro Asn Gln Ala
65                  70                  75                  80
```

```
Val Ser Ile Glu Val Asp Gly Leu Glu Val Asn Ile Arg Leu Val
                85                  90                  95

Asp Cys Val Gly Tyr Thr Val Pro Gly Ala Lys Gly Tyr Glu Asp Glu
                100                 105                 110

Asn Gly Pro Arg Met Ile Asn Thr Pro Trp Tyr Glu Pro Ile Pro
            115                 120                 125

Phe His Glu Ala Ala Glu Ile Gly Thr Arg Lys Val Ile Gln Glu His
        130                 135                 140

Ser Thr Ile Gly Val Val Ile Thr Thr Asp Gly Thr Ile Gly Glu Ile
145                 150                 155                 160

Pro Arg Arg Asp Tyr Ile Glu Ala Glu Arg Val Val Asn Glu Leu
                165                 170                 175

Lys Glu Val Gly Lys Pro Phe Ile Met Ile Ile Asn Thr Val Gln Pro
                180                 185                 190

Tyr His Pro Asp Thr Glu Gln Leu Arg Gln Ser Leu Ser Glu Glu Tyr
            195                 200                 205

Asp Ile Pro Val Ile Ala Met Ser Val Glu Ser Leu Arg Glu Thr Asp
        210                 215                 220

Val Tyr Asn Val Leu Arg Glu Ala Leu Phe Glu Phe Pro Val Leu Glu
225                 230                 235                 240

Val Asn Val Asn Leu Pro Ser Trp Val Met Val Leu Asn Glu Gly His
                245                 250                 255

Trp Leu Arg Gln Ser Tyr Gln Glu Ala Val Gln Glu Thr Val Lys Asp
                260                 265                 270

Ile Lys Arg Leu Arg Asp Val Asp Arg Val Val Trp Gln Phe Ser Gln
            275                 280                 285

Tyr Glu Phe Ile Asp Arg Ala Ser Leu Ala Gly Ile Asp Met Gly Gln
        290                 295                 300

Gly Val Ala Glu Ile Asp Leu Tyr Ala Pro Asp Glu Leu Tyr Asp Gln
305                 310                 315                 320

Ile Leu Lys Glu Val Val Gly Val Glu Ile Arg Gly Lys Asp His Leu
                325                 330                 335

Leu Lys Leu Met Leu Asp Leu Ser His Ala Lys Ile Glu Tyr Asp Gln
            340                 345                 350

Val Ala Asp Ala Leu Arg Met Val Lys Gln Thr Gly Tyr Gly Val Ala
        355                 360                 365

Ala Pro Ala Leu Ala Asp Met Ser Leu Asp Glu Pro Glu Ile Ile Arg
370                 375                 380

His Gly Ser Arg Phe Gly Val Lys Leu Lys Ala Val Ala Pro Ser Ile
385                 390                 395                 400

His Met Ile Lys Val Asp Val Glu Ser Thr Phe Glu Pro Ile Ile Gly
                405                 410                 415

Thr Glu Lys Gln Ser Glu Glu Leu Val Arg Tyr Leu Met Gln Asp Phe
            420                 425                 430

Glu Asp Asp Pro Leu Ser Ile Trp Asn Ser Asp Ile Phe Gly Arg Ser
        435                 440                 445

Leu Ser Ser Ile Val Arg Glu Gly Ile Gln Ala Lys Leu Ser Leu Met
450                 455                 460

Pro Glu Asn Ala Arg Tyr Lys Leu Lys Glu Thr Leu Glu Arg Ile Ile
465                 470                 475                 480

Asn Glu Gly Ser Gly Gly Leu Ile Ala Ile Ile Leu
                485                 490
```

<210> SEQ ID NO 16
<211> LENGTH: 492
<212> TYPE: PRT
<213> ORGANISM: Bacillus pumilus

<400> SEQUENCE: 16

```
Met Glu Lys Val Asp Ile Phe Lys Asp Ile Ala Glu Arg Thr Gly Gly
  1               5                  10                  15

Asp Ile Tyr Leu Gly Val Val Gly Ala Val Arg Thr Gly Lys Ser Thr
             20                  25                  30

Phe Ile Lys Lys Phe Met Glu Leu Val Val Leu Pro Asn Ile Asn Asn
         35                  40                  45

Glu Ala Asp Arg Ala Arg Ala Gln Asp Glu Leu Pro Gln Ser Ala Ala
     50                  55                  60

Gly Lys Thr Ile Met Thr Thr Glu Pro Lys Phe Val Pro Asn Gln Ala
 65                  70                  75                  80

Ala Ser Ile His Val Ser Asp Gly Leu Asp Val Asn Ile Arg Leu Val
                 85                  90                  95

Asp Cys Val Gly Tyr Thr Val Pro Gly Ala Arg Gly Tyr Glu Asp Glu
            100                 105                 110

Asn Gly Pro Arg Met Ile Asn Thr Pro Trp Tyr Glu Pro Ile Pro
        115                 120                 125

Phe His Glu Ala Ala Glu Ile Gly Thr Arg Lys Val Ile Gln Glu His
    130                 135                 140

Ser Thr Ile Gly Val Val Ile Thr Thr Asp Gly Ser Ile Gly Glu Ile
145                 150                 155                 160

Pro Arg His Asp Tyr Ile Glu Ser Glu Glu Arg Val Ile Asp Glu Leu
                165                 170                 175

Lys Glu Val Gly Lys Pro Phe Ile Met Val Ile Asn Ser Val Arg Pro
            180                 185                 190

Tyr His Pro Glu Thr Glu Ala Leu Arg Gln Glu Leu Ser Gln Lys Tyr
        195                 200                 205

Asp Ile Pro Val Leu Ala Met Ser Val Glu Ser Met Arg Glu Gln Asp
    210                 215                 220

Val Leu Ser Val Leu Arg Glu Ala Leu Tyr Glu Phe Pro Val Leu Glu
225                 230                 235                 240

Val Asn Val Asn Leu Pro Ser Trp Val Met Val Leu Lys Glu Asp His
                245                 250                 255

Trp Leu Arg Glu Ser Tyr Gln Asp Ser Val Lys Glu Thr Val Lys Asp
            260                 265                 270

Ile Lys Arg Leu Arg Asp Val Asp Arg Val Val Gly Gln Phe Ser Glu
        275                 280                 285

Phe Asp Phe Ile Glu Arg Ala Gly Leu Ala Gly Ile Glu Met Gly Gln
    290                 295                 300

Gly Ile Ala Glu Ile Asp Leu Tyr Ala Pro Asp Asp Leu Tyr Asp His
305                 310                 315                 320

Ile Leu Lys Glu Val Val Gly Val Glu Ile Arg Gly Lys Asp His Leu
                325                 330                 335

Leu Glu Leu Met Gln Asp Phe Ala His Ala Lys Thr Gly Tyr Asp Gln
            340                 345                 350

Val Ser Asp Ala Leu Lys Met Val Lys Gln Thr Gly Tyr Gly Ile Ala
        355                 360                 365

Ala Pro Ala Leu Ser Asp Met Ser Leu Asp Glu Pro Glu Ile Ile Arg
    370                 375                 380
```

```
Gln Gly Ser Arg Phe Gly Val Arg Leu Lys Ala Val Ala Pro Ser Ile
385                 390                 395                 400

His Met Ile Lys Val Asp Val Glu Ser Glu Phe Ala Pro Ile Ile Gly
            405                 410                 415

Thr Glu Lys Gln Ser Glu Glu Leu Val Arg Tyr Leu Met Gln Asp Phe
        420                 425                 430

Glu Asp Asp Pro Leu Ser Ile Trp Asn Ser Asp Ile Phe Gly Arg Ser
            435                 440                 445

Leu Ser Ser Leu Val Arg Glu Gly Ile Gln Ala Lys Leu Ser Leu Met
    450                 455                 460

Pro Glu Asn Ala Arg Tyr Lys Leu Lys Glu Thr Leu Glu Arg Ile Ile
465                 470                 475                 480

Asn Glu Gly Ser Gly Gly Leu Ile Ala Ile Ile Leu
                485                 490
```

<210> SEQ ID NO 17
<211> LENGTH: 493
<212> TYPE: PRT
<213> ORGANISM: Clostridium botulinum

<400> SEQUENCE: 17

```
Met Glu Asn Phe Asn Ile Tyr Lys Asp Ile Ala Glu Arg Thr Gln Gly
1               5                   10                  15

Asp Ile Tyr Val Gly Val Val Gly Pro Val Arg Thr Gly Lys Ser Thr
                20                  25                  30

Phe Ile Lys Lys Phe Met Glu Lys Met Val Ile Pro Lys Ile Glu Asn
            35                  40                  45

Ser Tyr Lys Lys Gln Arg Ala Lys Asp Glu Leu Pro Gln Ser Ser Ser
        50                  55                  60

Gly Lys Ala Ile His Thr Thr Glu Pro Lys Phe Val Pro Asn Glu Ala
65                  70                  75                  80

Val Glu Val Ser Leu Glu Asn Asp Thr Lys Phe Lys Val Arg Met Val
                85                  90                  95

Asp Cys Val Gly Tyr Ile Val Asn Gly Ala Leu Gly Tyr Met Glu Glu
            100                 105                 110

Glu Asp Lys Pro Lys Met Val Thr Thr Pro Trp Tyr Asp Tyr Glu Ile
        115                 120                 125

Pro Phe Glu Glu Ala Ala Glu Ile Gly Thr Lys Lys Val Ile Asn Glu
    130                 135                 140

His Ser Thr Ile Gly Leu Leu Ile Thr Thr Asp Gly Ser Ile Thr Asp
145                 150                 155                 160

Ile Asp Arg Glu Asn Tyr Val Glu Val Glu Arg Val Val Glu Glu
                165                 170                 175

Leu Lys Ser Ile Asn Lys Pro Phe Ile Ile Val Leu Asn Ser Ser His
            180                 185                 190

Pro Tyr Glu Pro Glu Thr Ile Glu Leu Arg Lys Asn Leu Glu Glu Glu
        195                 200                 205

Tyr Asp Val Pro Val Gln Thr Met Asp Ile Leu Asn Met Lys Glu Glu
    210                 215                 220

Asp Met Thr Asn Val Phe Gln Arg Val Leu Lys Glu Phe Pro Ile Lys
225                 230                 235                 240

Glu Val Asn Ile Asp Met Pro Ala Trp Ile Glu Glu Leu Lys Pro Glu
                245                 250                 255

His Trp Leu Lys Thr Asp Phe Ile Asn Val Val Lys Asn Met Ala Lys
```

```
              260                 265                 270
Glu Ile Tyr Lys Val Arg Asp Ile Lys Lys Ser Met Glu Asn Leu Tyr
            275                 280                 285

Glu Phe Glu Phe Leu Asp Asn Ser Thr Leu Asn Glu Met Asn Met Gly
            290                 295                 300

Glu Gly Thr Ala Arg Ile Ala Leu Arg Pro Lys Asp Gly Leu Phe Tyr
305                 310                 315                 320

Lys Ile Ile Gly Glu Val Cys Asn Arg Glu Ile Glu Asn Glu Asn Asp
                325                 330                 335

Leu Leu Lys Ile Val Glu Thr Met Asn Lys Ala Lys Ile Glu Tyr Asp
                340                 345                 350

Arg Ile Ala Glu Ala Leu Glu Asp Val Lys Glu Thr Gly Tyr Gly Leu
                355                 360                 365

Val Ala Pro Gln Leu Thr Glu Met Lys Leu Glu Pro Glu Ile Val
                370                 375                 380

Lys Gln Gly Ser Arg Tyr Gly Val Lys Leu Lys Ala Ser Ala Pro Ser
385                 390                 395                 400

Leu His Phe Ile Arg Ala Asp Ile Glu Thr Glu Val Ser Pro Ile Met
                405                 410                 415

Gly Thr Glu Lys Glu Ser Glu Met Leu Lys Ser Leu Leu Glu Glu
                420                 425                 430

Phe Glu Thr Asp Pro Ser Lys Ile Trp Gln Ser Asn Met Phe Gly Lys
                435                 440                 445

Ser Leu Glu Val Leu Val Lys Glu Gly Leu Gln Asn Lys Leu Tyr Arg
                450                 455                 460

Met Pro Glu Asp Val Gln Val Lys Ile Gln Lys Thr Leu Gln Lys Ile
465                 470                 475                 480

Ile Asn Glu Gly Asn Gly Gly Leu Ile Cys Ile Ile Leu
                485                 490

<210> SEQ ID NO 18
<211> LENGTH: 491
<212> TYPE: PRT
<213> ORGANISM: Clostridium perfringens

<400> SEQUENCE: 18

Met Glu Asp Phe Asn Ile Tyr Lys Asp Ile Ala Glu Arg Thr Gln Gly
1               5                   10                  15

Asp Ile Tyr Val Gly Val Gly Pro Val Arg Thr Gly Lys Ser Thr
                20                  25                  30

Phe Ile Lys Arg Phe Met Asp Leu Met Val Ile Pro Lys Ile Asp Asn
            35                  40                  45

Ala Tyr Lys Lys Glu Arg Ala Lys Asp Glu Leu Pro Gln Ser Gly Ser
        50                  55                  60

Gly Lys Thr Ile His Thr Thr Glu Pro Lys Phe Val Pro Asn Glu Ala
65                  70                  75                  80

Val Glu Ile Ala Leu Asp Asp Gly Ile Lys Phe Ser Val Arg Met Val
                85                  90                  95

Asp Cys Val Gly Tyr Ile Val Lys Gly Ala Asn Gly Tyr Phe Asp Asp
                100                 105                 110

Gly Glu Ser Lys Lys Val His Thr Pro Trp Phe Asp Tyr Glu Ile Pro
            115                 120                 125

Phe Glu Asp Ala Ala Glu Ile Gly Thr Arg Lys Val Ile Thr Asp His
        130                 135                 140
```

Ser Thr Ile Gly Leu Val Val Thr Thr Asp Gly Ile Thr Gly Ile
145                 150                 155                 160

Asp Arg Asp Asp Tyr Leu Asp Ala Glu Glu Arg Val Val Ala Glu Leu
            165                 170                 175

Lys Ser Ile Asp Lys Pro Phe Ile Ile Val Leu Asn Ser Leu Asp Pro
        180                 185                 190

Arg Ala Glu Glu Thr Leu Asp Leu Lys Gln Glu Leu Glu Ile Arg Tyr
    195                 200                 205

Gly Val Pro Val Gln Ile Met Asp Val Ala Asn Met Asn Glu Asn Asp
210                 215                 220

Ile Asn Asp Leu Phe Thr Lys Val Leu Lys Glu Phe Pro Val Lys Glu
225                 230                 235                 240

Ile Asn Ile Asp Met Pro Lys Trp Ile Glu Lys Leu Glu Pro Ser His
                245                 250                 255

Trp Leu Lys Ser Asn Phe Ile Asp Ile Val Lys Asp Met Cys Lys Asn
            260                 265                 270

Ile Ser Lys Ile Arg Asp Val Lys Asp Leu Leu Ser Thr Tyr Gly Glu
        275                 280                 285

Asp Phe Leu Gly Val Ala Asp Ile Ser Glu Met Asn Leu Gly Asp Gly
    290                 295                 300

Thr Val Arg Val Lys Met Thr Pro Lys Asn Gly Ile Phe Tyr Lys Ile
305                 310                 315                 320

Ile Ser Glu Met Cys Asp Glu Glu Leu Asn Asp Glu Ser Asp Leu Ile
                325                 330                 335

Ala Leu Ile Lys Asp Leu His Lys Ala Lys Ser Glu Tyr Asp Lys Val
            340                 345                 350

Ala Glu Ala Ile Asn Ser Val Lys Glu Thr Gly Tyr Gly Leu Val Ala
        355                 360                 365

Pro Gln Leu Ser Glu Met Lys Phe Glu Lys Pro Asp Ile Asp Lys Gln
    370                 375                 380

Gly Ser Lys Tyr Val Val Lys Leu Lys Ala Ser Ala Pro Ser Leu His
385                 390                 395                 400

Leu Ile Lys Ala Asp Ile Gln Thr Glu Ile Cys Pro Ile Met Gly Thr
                405                 410                 415

Glu Lys Glu Thr Gln Glu Val Phe Lys Thr Leu Leu Glu Gln Phe Glu
            420                 425                 430

Ser Asp Pro Glu Lys Leu Trp Gln Ser Asn Met Phe Gly Lys Ser Leu
        435                 440                 445

Glu Thr Leu Val Gln Gly Leu Arg Ser Lys Leu Tyr Lys Met Pro
    450                 455                 460

Asp Asp Ile Gln Ser Lys Ile Gln Lys Thr Leu Gln Arg Ile Ile Asn
465                 470                 475                 480

Glu Gly Glu Gly Asn Leu Ile Cys Ile Ile Phe
                485                 490

<210> SEQ ID NO 19
<211> LENGTH: 492
<212> TYPE: PRT
<213> ORGANISM: Oceanobacillus iheyensis

<400> SEQUENCE: 19

Met Glu Lys Thr Asp Ile Phe Lys Asp Ile Ser Lys Arg Thr Asn Gly
1               5                   10                  15

Asp Ile Tyr Leu Gly Ile Val Gly Ala Val Arg Thr Gly Lys Ser Thr
            20                  25                  30

```
Phe Ile Lys Lys Phe Met Glu Leu Val Val Leu Pro Asn Ile Glu Ser
            35                  40                  45

Glu Ser Asp Arg Ala Arg Ala His Asp Glu Leu Pro Gln Ser Ala Ala
     50                  55                  60

Gly Lys Thr Ile Met Thr Thr Glu Pro Lys Phe Ile Pro Asn Gln Ala
 65                  70                  75                  80

Val Gln Val Lys Val Asp Asp Gly Leu Asp Val Asn Val Arg Leu Val
                 85                  90                  95

Asp Cys Val Gly Tyr Ala Val Glu Gly Ala Lys Gly Phe Glu Asp Glu
                100                 105                 110

Asn Gly Pro Arg Met Ile His Thr Pro Trp Tyr Glu Asp Pro Ile Pro
            115                 120                 125

Phe His Asp Ala Ala Glu Ile Gly Thr Arg Lys Val Ile Gln Glu His
        130                 135                 140

Ser Thr Ile Gly Val Val Thr Thr Asp Gly Ser Ile Gly Glu Ile
145                 150                 155                 160

Glu Arg His Asp Tyr Glu Asp Ala Glu Thr Arg Val Val Glu Glu Leu
                165                 170                 175

Lys Glu Val Gly Lys Pro Phe Ile Met Val Ile Asn Ser Thr Gln Pro
            180                 185                 190

Arg Ser Gln Glu Thr Glu Leu Leu Arg Gln Glu Leu Val Glu Lys His
        195                 200                 205

Asp Ile Pro Val Leu Ala Met Ser Ile Glu Ser Met Thr Glu His Asp
210                 215                 220

Val Tyr Asn Val Leu Arg Glu Ala Leu Phe Glu Phe Pro Val Leu Glu
225                 230                 235                 240

Val Asn Val Asn Leu Pro Ser Trp Val Met Val Leu Asn Glu Arg His
                245                 250                 255

Trp Leu Arg Gln Asn Tyr Gln Asp Ala Ile Gln Thr Thr Val Lys Asp
            260                 265                 270

Ile Lys Arg Leu Arg Asp Val Asp His Ile Val Gly Asn Phe Thr Asp
        275                 280                 285

Tyr Asp Tyr Ile Glu Gln Ala Ser Leu Ala Gly Met Glu Met Gly Glu
290                 295                 300

Gly Ile Ala Glu Ile Asp Leu His Ala Pro Asp Tyr Leu Tyr Asp Glu
305                 310                 315                 320

Val Leu Lys Glu Ile Val Gly Glu Ile Arg Gly Lys Asp His Leu
                325                 330                 335

Leu Glu Leu Met Gln Asp Phe Ala Tyr Ala Lys Arg Glu Tyr Asp Gln
            340                 345                 350

Val Ala Gly Ala Leu Gln Met Val Lys Gln Thr Gly Tyr Gly Ile Ala
        355                 360                 365

Ala Pro Thr Leu Glu Asp Met Gln Leu Asp Glu Pro Glu Ile Ile Arg
370                 375                 380

Gln Gly Ser Arg Phe Gly Val Arg Leu Lys Ala Val Ala Pro Ser Ile
385                 390                 395                 400

His Met Ile Arg Val Glu Val Glu Ser Glu Phe Ala Pro Ile Ile Gly
                405                 410                 415

Thr Glu Lys Gln Ser Glu Glu Leu Val Arg Tyr Leu Met Gln Asp Phe
            420                 425                 430

Glu Glu Asp Pro Leu Ser Ile Trp Glu Ser Asp Ile Phe Gly Arg Ser
        435                 440                 445
```

```
Leu Ser Ser Ile Val Arg Glu Gly Ile Gln Ala Lys Ile Ser Leu Met
450                 455                 460

Pro Glu Asn Ala Arg Tyr Lys Leu Lys Asp Thr Leu Glu Arg Ile Ile
465                 470                 475                 480

Asn Glu Gly Ser Gly Gly Leu Ile Ala Ile Ile Leu
            485                 490

<210> SEQ ID NO 20
<211> LENGTH: 493
<212> TYPE: PRT
<213> ORGANISM: Symbiobacterium thermophilum

<400> SEQUENCE: 20

Met Glu Arg Ile Asp Ile Phe Glu Asp Val Ala Arg Arg Thr Gly Gly
1               5                   10                  15

Asp Ile Tyr Ile Gly Val Val Gly Pro Val Arg Thr Gly Lys Ser Thr
                20                  25                  30

Phe Ile Arg Arg Leu Ala Glu Gln Val Ile Leu Pro Asn Ile Glu Asp
            35                  40                  45

Glu Tyr Leu Gln Ala Arg Ile Arg Asp Glu Leu Pro Gln Ser Gly Asn
        50                  55                  60

Gly Arg Thr Ile Met Thr Val Glu Pro Lys Phe Val Pro Asp Glu Ala
65                  70                  75                  80

Val Glu Ile Thr Leu Arg Glu Gly Leu Thr Val Arg Val Arg Leu Val
                85                  90                  95

Asp Ser Val Gly Tyr Ala Val Glu Gly Ala Leu Gly Tyr Met Gln Glu
            100                 105                 110

Asp Gly Ser Pro Arg Met Val Arg Thr Pro Trp Phe Glu Glu Ile
        115                 120                 125

Pro Phe His Asp Ala Ala Glu Ile Gly Thr Arg Lys Val Ile Ala Glu
        130                 135                 140

His Ser Thr Ile Gly Leu Leu Val Thr Thr Asp Gly Thr Ile Thr Asp
145                 150                 155                 160

Leu Ala Arg Gly Lys Tyr Leu Glu Ala Glu Arg Val Val Ser Glu
                165                 170                 175

Leu Gln Ala Leu Gly Lys Pro Phe Val Ile Val Leu Asn Thr Thr Arg
            180                 185                 190

Pro Tyr Ala Gln Glu Thr Met Glu Leu Ala Gly Glu Leu Glu Val Lys
        195                 200                 205

Tyr Asn Ala Pro Val Ile Pro Val Asp Ala Ser Glu Leu Thr Gln Asp
        210                 215                 220

Asp Ile His Leu Ile Leu Glu Gln Ala Leu Phe Glu Phe Pro Val Arg
225                 230                 235                 240

Glu Ala Asn Ile Ala Leu Pro Arg Trp Val Glu Glu Leu Asp Ser Ala
                245                 250                 255

His Pro Val Arg Ala Gln Phe Glu Glu Ala Ile Ala Glu Ala Leu Gln
            260                 265                 270

Gly Ile Gln Lys Ile Arg Asp Val Asp Ala Ala Val Glu Arg Leu Ser
        275                 280                 285

Ser Tyr Glu Phe Met Ala Ala Val Asn Leu Gln Ser Ile Asp Met Gly
        290                 295                 300

Ala Gly Val Ala His Val Gln Thr Glu Ala Arg Asp Asp Leu Tyr Tyr
305                 310                 315                 320

Gln Val Leu Glu Glu Ile Thr Gly Val Pro Leu Glu Gly Lys His Thr
                325                 330                 335
```

```
Met Val Arg Leu Leu Arg Glu Tyr Thr Gln Ala Lys Arg Glu Tyr Asp
                340                 345                 350

Lys Ile Lys Asp Ala Leu Glu Asp Val Lys Ala Thr Gly Tyr Gly Val
            355                 360                 365

Val Thr Pro Ala Ile Glu Asp Ile Thr Phe Glu Glu Pro Glu Leu Val
        370                 375                 380

Arg Gln Gly Ile Met Tyr Gly Val Lys Leu Gln Ala Thr Ala Pro Ser
385                 390                 395                 400

Leu His Phe Ile Arg Ala Asp Ile Ser Ala Glu Val Thr Pro Ile Ile
                405                 410                 415

Gly Thr Ala Lys Gln Gly Glu Glu Leu Val Gln Tyr Leu Leu Glu Arg
            420                 425                 430

Phe Glu Asp Asp Pro Arg Gln Leu Trp Glu Phe Asp Ile Phe Gly Lys
        435                 440                 445

Ser Leu His Glu Leu Val Gln Glu Gly Ile Lys Ala Lys Leu His Arg
    450                 455                 460

Met Pro Glu Asp Ala Gln Val Lys Leu Gln Glu Thr Leu Ser Arg Ile
465                 470                 475                 480

Ile Asn Glu Gly Ser Gly Gly Leu Ile Cys Ile Ile Ile
                485                 490

<210> SEQ ID NO 21
<211> LENGTH: 492
<212> TYPE: PRT
<213> ORGANISM: Bacillus cereus

<400> SEQUENCE: 21

Met Glu Lys Val Asp Ile Phe Lys Asp Ile Ala Glu Arg Thr Gly Gly
1               5                   10                  15

Asp Ile Tyr Phe Gly Val Val

```
                210                 215                 220
Val Tyr Asn Val Leu Arg Glu Ala Leu Phe Glu Phe Pro Val Leu Glu
225                 230                 235                 240

Val Asn Val Asn Leu Pro Ser Trp Val Met Val Leu Asn Glu Gly His
                245                 250                 255

Trp Leu Arg Gln Ser Tyr Gln Glu Ala Val Gln Glu Thr Val Lys Asp
                260                 265                 270

Ile Lys Arg Leu Arg Asp Val Asp Arg Val Val Trp Gln Phe Ser Gln
            275                 280                 285

Tyr Glu Phe Ile Asp Arg Ala Ser Leu Ala Gly Ile Asp Met Gly Gln
            290                 295                 300

Gly Val Ala Glu Ile Asp Leu Tyr Ala Pro Asp Glu Leu Tyr Asp Gln
305                 310                 315                 320

Ile Leu Lys Glu Val Val Gly Val Glu Ile Arg Gly Lys Asp His Leu
                325                 330                 335

Leu Lys Leu Met Leu Asp Leu Ser His Ala Lys Ile Glu Tyr Asp Gln
                340                 345                 350

Val Ala Asp Ala Leu Arg Met Val Lys Gln Thr Gly Tyr Gly Val Ala
            355                 360                 365

Ala Pro Ala Leu Ala Asp Met Ser Leu Asp Glu Pro Glu Ile Ile Arg
            370                 375                 380

His Gly Ser Arg Phe Gly Val Lys Leu Lys Ala Val Ala Pro Ser Ile
385                 390                 395                 400

His Met Ile Lys Val Asp Val Glu Ser Thr Phe Glu Pro Ile Ile Gly
                405                 410                 415

Thr Glu Lys Gln Ser Glu Leu Val Arg Tyr Leu Met Gln Asp Phe
                420                 425                 430

Glu Asp Asp Pro Leu Ser Ile Trp Asn Ser Asp Ile Phe Gly Arg Ser
            435                 440                 445

Leu Ser Ser Ile Val Arg Glu Gly Ile Gln Ala Lys Leu Ser Leu Met
            450                 455                 460

Pro Glu Asn Ala Arg Tyr Lys Leu Lys Glu Thr Leu Glu Arg Ile Ile
465                 470                 475                 480

Asn Glu Gly Ser Gly Gly Leu Ile Ala Ile Ile Leu
                485                 490

<210> SEQ ID NO 22
<211> LENGTH: 492
<212> TYPE: PRT
<213> ORGANISM: Bacillus halodurans

<400> SEQUENCE: 22

Met Glu Lys Ile Asp Ile Phe Lys Asp Ile Ala Glu Arg Thr Gly Gly
1               5                   10                  15

Asp Ile Tyr Leu Gly Val Val Gly Ala Val Arg Thr Gly Lys Ser Thr
                20                  25                  30

Phe Ile Lys Lys Phe Met Glu Leu Val Val Leu Pro Asn Ile Glu Asn
            35                  40                  45

Glu Ala Asp Lys Ala Arg Ala Gln Asp Glu Leu Pro Gln Ser Ala Ala
        50                  55                  60

Gly Lys Thr Ile Met Thr Thr Glu Pro Lys Phe Val Pro Asn Gln Ala
65                  70                  75                  80

Val Ser Ile His Val Asp Glu Gly Leu Asp Val Asn Val Arg Leu Val
                85                  90                  95
```

```
Asp Cys Val Gly Tyr Ala Val Pro Gly Ala Lys Gly Tyr Glu Asp Glu
                100                 105                 110

Asn Gly Pro Arg Met Ile Asn Thr Pro Trp Tyr Glu Glu Pro Ile Pro
            115                 120                 125

Phe Gln Glu Ala Ala Glu Ile Gly Thr Arg Lys Val Ile Gln Glu His
        130                 135                 140

Ser Thr Leu Gly Val Val Ile Thr Thr Asp Gly Ser Ile Gly Glu Ile
145                 150                 155                 160

Pro Arg Tyr Asp Tyr Ile Glu Ser Glu Thr Arg Val Ile Glu Glu Leu
                165                 170                 175

Lys Glu Val Gly Lys Pro Phe Ile Ile Val Ile Asn Ser Val Arg Pro
            180                 185                 190

His His Pro Glu Thr Glu Gln Leu Arg Arg Asp Leu Gln Glu Glu His
        195                 200                 205

Asp Ile Pro Val Leu Ala Met Ser Ile Glu Ser Met Gly Glu Gln Asp
210                 215                 220

Ile Asn Asn Val Leu Arg Glu Val Leu Phe Glu Phe Pro Val His Glu
225                 230                 235                 240

Val Asn Val Asn Leu Pro Ser Trp Val Met Val Leu Lys Glu Glu His
            245                 250                 255

Trp Leu Arg Gln Asn Tyr Glu Gln Ser Val Arg Asp Thr Val Gln Asp
        260                 265                 270

Ile Lys Arg Leu Arg Asp Val Asp Arg Val Val Gly His Phe Ala Glu
    275                 280                 285

Tyr Glu Phe Ile Asp Asp Ala Arg Leu Ala Gly Ile Glu Met Gly Gln
290                 295                 300

Gly Ile Ala Glu Ile Asp Leu Tyr Ala Pro Asp Asp Leu Tyr Asp Gln
305                 310                 315                 320

Ile Leu Lys Glu Val Val Gly Val Glu Ile Arg Gly Lys Asp His Leu
            325                 330                 335

Leu His Leu Met Gln Glu Phe Ala His Ala Lys Ser Glu Tyr Asp Gln
        340                 345                 350

Val Ala Asp Ala Leu Arg Met Val Lys Gln Thr Gly Tyr Gly Ile Ala
    355                 360                 365

Ala Pro Ala Leu Ser Asp Met Ser Leu Asp Glu Pro Glu Ile Ile Arg
370                 375                 380

Gln Gly Ser Arg Phe Gly Val Arg Leu Lys Ala Val Ala Pro Ser Ile
385                 390                 395                 400

His Met Ile Lys Val Asp Val Glu Ser Glu Phe Ala Pro Ile Ile Gly
            405                 410                 415

Thr Glu Lys Gln Ser Glu Glu Leu Val Arg Tyr Leu Met Gln Asp Phe
        420                 425                 430

Glu Glu Asn Pro Leu Ser Ile Trp Asn Ser Asp Ile Phe Gly Arg Ser
    435                 440                 445

Leu Asn Ser Ile Val Arg Glu Gly Ile Ser Ala Lys Leu Ser Leu Met
450                 455                 460

Pro Glu Asn Ala Arg Tyr Lys Leu Lys Glu Thr Leu Glu Arg Ile Ile
465                 470                 475                 480

Asn Glu Gly Ser Gly Gly Leu Ile Ala Ile Ile Leu
            485                 490

<210> SEQ ID NO 23
<211> LENGTH: 492
<212> TYPE: PRT
```

<213> ORGANISM: Bacillus thuringiensis

<400> SEQUENCE: 23

```
Met Glu Lys Val Asp Ile Phe Lys Asp Ile Ala Glu Arg Thr Gly Gly
1               5                   10                  15
Asp Ile Tyr Phe Gly Val Val Gly Ala Val Arg Thr Gly Lys Ser Thr
            20                  25                  30
Phe Ile Lys Lys Phe Met Glu Leu Val Val Ile Pro Asn Ile Glu Asn
        35                  40                  45
Glu Ser Asp Arg Gln Arg Ala Gln Asp Glu Leu Pro Gln Ser Ala Ala
    50                  55                  60
Gly Arg Thr Ile Met Thr Thr Glu Pro Lys Phe Val Pro Asn Gln Ala
65                  70                  75                  80
Val Ser Ile Glu Val Asp Glu Gly Leu Glu Val Asn Ile Arg Leu Val
                85                  90                  95
Asp Cys Val Gly Tyr Thr Val Pro Gly Ala Lys Gly Tyr Glu Asp Glu
            100                 105                 110
Asn Gly Pro Arg Met Ile Asn Thr Pro Trp Tyr Glu Pro Ile Pro
        115                 120                 125
Phe His Glu Ala Ala Glu Ile Gly Thr Arg Lys Val Ile Gln Glu His
    130                 135                 140
Ser Thr Ile Gly Val Val Ile Thr Thr Asp Gly Thr Ile Gly Glu Ile
145                 150                 155                 160
Pro Arg Arg Asp Tyr Ile Glu Ala Glu Arg Val Val Asn Glu Leu
                165                 170                 175
Lys Glu Val Gly Lys Pro Phe Ile Met Ile Asn Thr Val Gln Pro
            180                 185                 190
Tyr His Pro Asp Thr Glu Gln Leu Arg Gln Ser Leu Ser Glu Glu Tyr
        195                 200                 205
Asp Ile Pro Val Ile Ala Met Ser Val Glu Ser Leu Arg Glu Thr Asp
    210                 215                 220
Val Tyr Asn Val Leu Arg Glu Ala Leu Phe Glu Phe Pro Val Leu Glu
225                 230                 235                 240
Val Asn Val Asn Leu Pro Ser Trp Val Met Val Leu Asn Glu Gly His
                245                 250                 255
Trp Leu Arg Gln Ser Tyr Gln Glu Ala Val Gln Glu Thr Val Lys Asp
            260                 265                 270
Ile Lys Arg Leu Arg Asp Val Asp Arg Val Val Trp Gln Phe Ser Gln
        275                 280                 285
Tyr Glu Phe Ile Asp Arg Ala Ser Leu Ala Gly Ile Asp Met Gly Gln
    290                 295                 300
Gly Val Ala Glu Ile Asp Leu Tyr Ala Pro Asp Glu Leu Tyr Asp Gln
305                 310                 315                 320
Ile Leu Lys Glu Val Val Gly Val Glu Ile Arg Gly Lys Asp His Leu
                325                 330                 335
Leu Lys Leu Met Leu Asp Leu Ser His Ala Lys Ile Glu Tyr Asp Gln
            340                 345                 350
Val Ala Asp Ala Leu Arg Met Val Lys Gln Thr Gly Tyr Gly Val Ala
        355                 360                 365
Ala Pro Ala Leu Ala Asp Met Ser Leu Asp Glu Pro Glu Ile Ile Arg
    370                 375                 380
His Gly Ser Arg Phe Gly Val Lys Leu Lys Ala Val Ala Pro Ser Ile
385                 390                 395                 400
```

His Met Ile Lys Val Asp Val Glu Ser Thr Phe Glu Pro Ile Ile Gly
                405                 410                 415

Thr Glu Lys Gln Ser Glu Glu Leu Val Arg Tyr Leu Met Gln Asp Phe
            420                 425                 430

Glu Asp Asp Pro Leu Ser Ile Trp Asn Ser Asp Ile Phe Gly Arg Ser
        435                 440                 445

Leu Ser Ser Ile Val Arg Glu Gly Ile Gln Ala Lys Leu Ser Leu Met
450                 455                 460

Pro Glu Asn Ala Arg Tyr Lys Leu Lys Glu Thr Leu Glu Arg Ile Ile
465                 470                 475                 480

Asn Glu Gly Ser Gly Gly Leu Ile Ala Ile Ile Leu
                485                 490

<210> SEQ ID NO 24
<211> LENGTH: 492
<212> TYPE: PRT
<213> ORGANISM: Carboxydibrachium pacificum

<400> SEQUENCE: 24

Met Glu Gly Tyr Asp Ile Tyr Arg Asp Ile Ala Glu Arg Thr Gln Gly
1               5                   10                  15

Asp Ile Tyr Ile Gly Val Val Gly Pro Val Arg Thr Gly Lys Ser Thr
            20                  25                  30

Phe Ile Lys Arg Phe Met Asp Ile Leu Val Leu Pro Asn Leu Glu Glu
        35                  40                  45

Ala Pro Leu Lys Glu Arg Ile Arg Asp Glu Leu Pro Gln Ser Ala Ala
    50                  55                  60

Gly Lys Thr Val Met Thr Thr Glu Pro Lys Phe Val Pro Glu Lys Ala
65                  70                  75                  80

Val Glu Ile Thr Ile Asn Glu Asn Thr Lys Phe Lys Val Arg Leu Val
                85                  90                  95

Asp Cys Val Gly Tyr Met Val Lys Gly Ala Leu Gly Tyr Met Glu Gly
            100                 105                 110

Asp Lys Pro Arg Met Val Ser Thr Pro Trp Tyr Asp Tyr Glu Ile Pro
        115                 120                 125

Phe Glu Glu Ala Ala Glu Ile Gly Thr Arg Lys Val Ile Ser Asp His
    130                 135                 140

Ser Thr Ile Gly Leu Val Val Thr Thr Asp Gly Ser Ile Thr Glu Ile
145                 150                 155                 160

Pro Arg Glu Asn Tyr Val Pro Ala Glu Glu Arg Val Ile Lys Glu Leu
                165                 170                 175

Lys Glu Leu Asn Lys Pro Phe Ile Ile Leu Leu Asn Thr Thr His Pro
            180                 185                 190

Gln Asn Thr Glu Thr Met Asn Leu Ala Ser Glu Leu Glu Lys Lys Tyr
        195                 200                 205

Asp Thr Pro Val Ile Val Val Asn Val Met Gln Met Glu Ile Lys Asp
    210                 215                 220

Ile Tyr Lys Ile Leu Glu Lys Val Leu Phe Glu Phe Pro Ile Arg Glu
225                 230                 235                 240

Ile Ala Ile Asp Leu Pro Thr Trp Val Asp Ala Leu Asp Lys Asn His
                245                 250                 255

Trp Phe Lys Glu Asn Val Leu Ser Thr Val Lys Glu Ser Val Lys Asp
            260                 265                 270

Leu Tyr Arg Leu Arg Asp Ile Ser Asn Leu Val Gly Gly Leu Lys Ala
        275                 280                 285

```
Asn Glu Asn Phe Ser Glu Val Phe Ile Lys Lys Ile Ala Pro Gly Glu
                290                 295                 300

Gly Ser Ala Asn Ile Glu Ile Lys Thr His Glu Gly Leu Phe Phe Lys
305                 310                 315                 320

Ile Leu Ser Asp Glu Ser Gly Leu Thr Ile Lys Asn Asp Lys Glu Leu
                325                 330                 335

Met Ser Val Ile Lys Glu Leu Ala His Ala Lys Arg Gln Tyr Asp Arg
                340                 345                 350

Ile Lys Glu Ala Phe Leu Lys Ala Gln Glu Thr Gly Val Gly Val Val
                355                 360                 365

Pro Ala Ser Leu Glu Glu Met Lys Phe Glu Lys Pro Glu Ile Val Arg
370                 375                 380

Gln Gly Gly Arg Phe Ala Val Arg Leu Lys Ala Ser Ala Pro Ser Tyr
385                 390                 395                 400

His Ile Phe Arg Thr Asp Ile Thr Ala Glu Val Thr Pro Val Val Gly
                405                 410                 415

Thr Glu Lys Gln Ser Glu Asp Phe Val Lys Tyr Ile Thr Glu Gln Phe
                420                 425                 430

Glu Asn Ala Pro Glu Lys Ile Trp Glu Ser Asn Ile Phe Gly Lys Thr
                435                 440                 445

Leu Ser Asp Leu Val Lys Glu Gly Met Gln Asn Lys Val Ser Ala Ile
450                 455                 460

Pro Glu Asn Leu Ser His Lys Leu Arg Asp Thr Leu Glu Lys Val Val
465                 470                 475                 480

Asn Asp Ser Gly Gly Ile Ile Phe Ile Ile
                485                 490

<210> SEQ ID NO 25
<211> LENGTH: 492
<212> TYPE: PRT
<213> ORGANISM: Geobacillus kaustophilus

<400> SEQUENCE: 25

Met Glu Lys Val Asp Ile Phe Lys Asp Ile Ala Glu Arg Thr Gly Gly
1               5                   10                  15

Asp Ile Tyr Leu Gly Val Val Gly Ala Val Arg Thr Gly Lys Ser Thr
                20                  25                  30

Phe Ile Lys Arg Phe Met Glu Leu Val Val Ile Pro Asn Ile Lys Asn
                35                  40                  45

Glu Ala Asp Lys Ala Arg Ala Gln Asp Glu Leu Pro Gln Ser Ala Ala
            50                  55                  60

Gly Lys Thr Ile Met Thr Thr Glu Pro Lys Phe Val Pro Asn Gln Ala
65                  70                  75                  80

Val Thr Val Lys Val Asp Glu Gly Leu Glu Val Asn Ile Arg Leu Val
                85                  90                  95

Asp Cys Val Gly Tyr Ala Val Pro Gly Ala Lys Gly Tyr Glu Asp Glu
                100                 105                 110

Asn Gly Pro Arg Met Ile His Thr Pro Trp Tyr Glu Glu Pro Ile Pro
                115                 120                 125

Phe Gln Glu Ala Ala Glu Ile Gly Thr Arg Lys Val Ile Gln Glu His
            130                 135                 140

Ser Thr Ile Gly Val Val Ile Thr Thr Asp Gly Thr Ile Gly Glu Ile
145                 150                 155                 160

Pro Arg Gln Asp Tyr Val Glu Ala Glu Glu Arg Val Ile Ser Glu Leu
```

```
            165                 170                 175
Lys Glu Val Gly Lys Pro Phe Ile Met Ile Val Asn Thr Val Arg Pro
            180                 185                 190

His His Pro Glu Thr Glu Ala Leu Arg Arg Glu Leu Ala Glu Lys Tyr
        195                 200                 205

Asp Ile Pro Val Leu Ala Met Ser Val Glu Ser Met Arg Glu Ala Asp
    210                 215                 220

Val Tyr Asn Val Leu Arg Glu Ala Leu Tyr Glu Phe Pro Val Leu Glu
225                 230                 235                 240

Val Asn Val Asn Leu Pro Ser Trp Val Met Val Leu Arg Glu Asp His
                245                 250                 255

Trp Leu Arg Glu Ser Tyr Gln Glu Ala Val Arg Asp Thr Val Lys Asp
            260                 265                 270

Ile Lys Arg Leu Arg Asp Val Asp Arg Val Val Gln Gln Phe Ala Glu
        275                 280                 285

Tyr Asp Phe Ile Glu Lys Ala Ala Leu Ala Gly Ile Glu Met Gly Gln
    290                 295                 300

Gly Ile Ala Glu Ile Asp Leu Tyr Ala Pro Asp Glu Leu Tyr Asp Gln
305                 310                 315                 320

Ile Leu Lys Glu Ile Val Gly Val Glu Ile Arg Gly Lys Asp His Leu
                325                 330                 335

Leu Gln Leu Met Gln Asp Phe His Ala Lys Ala Gly Tyr Asp Gln
            340                 345                 350

Ile Ala Asp Ala Leu Lys Met Val Lys Gln Thr Gly Tyr Gly Ile Ala
        355                 360                 365

Ala Pro Ala Leu Ser Asp Met Ser Leu Asp Glu Pro Glu Ile Ile Arg
    370                 375                 380

Gln Gly Ser Arg Phe Gly Val Arg Leu Lys Ala Val Ala Pro Ser Ile
385                 390                 395                 400

His Met Ile Lys Val Asp Val Glu Ser Glu Phe Ala Pro Ile Ile Gly
                405                 410                 415

Thr Glu Lys Gln Ser Glu Glu Leu Val Arg Tyr Leu Met Gln Asp Phe
            420                 425                 430

Glu Asp Asp Pro Leu Ser Ile Trp Asn Ser Asp Ile Phe Gly Arg Ser
        435                 440                 445

Leu Ser Ser Ile Val Arg Glu Gly Ile Gln Ala Lys Leu Ala Leu Met
    450                 455                 460

Pro Glu Asn Ala Arg Tyr Lys Leu Lys Glu Thr Leu Glu Arg Ile Ile
465                 470                 475                 480

Asn Glu Gly Ser Gly Gly Leu Ile Ala Ile Ile Leu
                485                 490

<210> SEQ ID NO 26
<211> LENGTH: 508
<212> TYPE: PRT
<213> ORGANISM: Anoxybacillus flavithermus

<400> SEQUENCE: 26

Met His Ile Val Ser Ser Tyr Val Leu Asn Ile Arg Glu Gly Arg Gln
1               5                   10                  15

Leu Glu Lys Val Asp Leu Phe Lys Asp Ile Ala Glu Arg Thr Gly Gly
            20                  25                  30

Asp Ile Tyr Leu Gly Val Val Gly Ala Val Arg Thr Gly Lys Ser Thr
        35                  40                  45
```

```
Phe Ile Lys Lys Phe Met Glu Leu Val Val Ile Pro Asn Ile Gln Asn
 50                  55                  60

Glu Ala Asp Lys Ala Arg Ala Gln Asp Glu Leu Pro Gln Ser Ala Ala
 65                  70                  75                  80

Gly Lys Thr Ile Met Thr Thr Glu Pro Lys Phe Val Pro Asn Gln Ala
                     85                  90                  95

Val Lys Val Lys Val Asp Asp Gly Leu Glu Val Asn Ile Arg Leu Val
                    100                 105                 110

Asp Cys Val Gly Tyr Thr Val Gln Gly Ala Lys Gly Phe Glu Asp Glu
                115                 120                 125

Asn Gly Pro Arg Met Ile His Thr Pro Trp Tyr Glu Glu Pro Ile Pro
130                 135                 140

Phe Gln Glu Ala Ala Glu Ile Gly Thr Arg Lys Val Ile Gln Glu His
145                 150                 155                 160

Ser Thr Ile Gly Val Val Ile Thr Thr Asp Gly Ser Ile Gly Glu Ile
                165                 170                 175

Pro Arg Glu Asn Tyr Val Glu Ala Glu Arg Val Val Asn Glu Leu
                180                 185                 190

Lys Glu Val Gly Lys Pro Phe Ile Met Ile Ile Asn Thr Val Arg Pro
            195                 200                 205

Gln His Pro Glu Thr Glu Thr Leu Lys Gln Gln Leu Ser Glu Lys Tyr
        210                 215                 220

Asp Ile Pro Val Leu Ala Leu Ser Val Glu Gly Met Arg Glu Ala Asp
225                 230                 235                 240

Val Tyr Gln Val Leu Arg Glu Ala Leu Tyr Glu Phe Pro Val Leu Glu
                245                 250                 255

Val Asn Val Asn Leu Pro Asn Trp Val Met Val Leu Arg Glu Asn His
                260                 265                 270

Trp Leu Arg Glu Ser Tyr Gln Asp Ala Val Arg Asp Thr Val Lys Asp
            275                 280                 285

Ile Lys Arg Leu Arg Asp Val Asp Arg Val Val Gln Gln Phe Ser Glu
290                 295                 300

Tyr Asp Phe Ile Asp Glu Ala Arg Leu Ala Gly Ile Glu Met Gly Gln
305                 310                 315                 320

Gly Ile Ala Glu Ile Asp Leu Tyr Ala Pro Asp Glu Leu Tyr Asp Gln
                325                 330                 335

Ile Leu Lys Glu Val Gly Val Glu Ile Arg Gly Lys Asp His Leu
                340                 345                 350

Leu Gln Leu Met Gln Asp Phe Ala Tyr Ala Lys Ala Gly Tyr Asp Gln
            355                 360                 365

Ile Ala Asp Ala Leu Arg Met Val Lys Gln Thr Gly Tyr Gly Ile Ala
370                 375                 380

Ala Pro Ser Leu Ser Asp Met Ser Leu Asp Glu Pro Glu Ile Ile Arg
385                 390                 395                 400

Gln Gly Ser Arg Phe Gly Val Arg Leu Lys Ala Val Ala Pro Ser Ile
                405                 410                 415

His Met Ile Lys Val Asp Val Glu Ser Glu Phe Ala Pro Ile Ile Gly
                420                 425                 430

Thr Glu Lys Gln Ser Glu Glu Leu Val Arg Tyr Leu Met Gln Asp Phe
            435                 440                 445

Glu Asp Asp Pro Leu Ser Ile Trp Asn Ser Asp Ile Phe Gly Arg Ser
450                 455                 460

Leu Ser Ser Ile Val Arg Glu Gly Ile Gln Ala Lys Leu Ala Leu Met
```

```
                465                 470                 475                 480
Pro Glu Asn Ala Arg Tyr Lys Leu Lys Glu Thr Leu Glu Arg Ile Ile
                    485                 490                 495

Asn Glu Gly Ser Gly Gly Leu Ile Ala Ile Ile Leu
                500                 505

<210> SEQ ID NO 27
<211> LENGTH: 492
<212> TYPE: PRT
<213> ORGANISM: Heliobacterium modesticaldum

<400> SEQUENCE: 27

Met Glu Lys Leu Asp Ile Phe Arg Asp Ile Ser Asp Arg Thr Gly Gly
1               5                   10                  15

Asp Ile Tyr Ile Gly Val Val Gly Pro Val Arg Thr Gly Lys Ser Thr
                20                  25                  30

Phe Ile Lys Arg Phe Met Glu His Leu Val Leu Pro Asn Ile Lys Asn
                35                  40                  45

Ile His Asp Lys Glu Arg Ala Arg Asp Glu Leu Pro Gln Ser Gly Ala
        50                  55                  60

Gly Arg Thr Ile Met Thr Thr Glu Pro Lys Phe Ile Pro Asn Glu Ala
65                  70                  75                  80

Val Glu Ile Gly Val Lys Asn Gly Leu Lys Met Arg Ile Arg Met Val
                85                  90                  95

Asp Cys Val Gly Tyr Thr Val Asp Gly Ala Leu Gly Tyr Glu Glu Glu
                100                 105                 110

Glu Gly Pro Arg Met Val Met Thr Pro Trp Ala Glu Ala Glu Met Pro
                115                 120                 125

Phe Gln Asp Ala Ala Glu Ile Gly Thr Arg Lys Val Ile Ala Asp His
130                 135                 140

Ser Thr Ile Gly Leu Val Val Thr Thr Asp Gly Ser Ile Thr Asp Leu
145                 150                 155                 160

Pro Arg Glu Ser Tyr Val Glu Ala Glu Glu Arg Val Ile Glu Glu Leu
                165                 170                 175

Arg Glu Leu His Lys Pro Phe Val Val Ile Leu Asn Ser Met Arg Pro
                180                 185                 190

His Ser Arg Glu Thr Ala Glu Leu Ala Tyr Thr Leu Glu Ser Gln Tyr
                195                 200                 205

Gln Val Pro Val Leu Pro Leu Asn Val Ser Glu Leu Asn Gln Asp Asp
                210                 215                 220

Ile Leu Lys Leu Leu Glu Ala Leu Phe Glu Phe Pro Val Thr Glu
225                 230                 235                 240

Val Asn Val Asn Leu Pro Leu Trp Ile Glu Glu Leu Asp Val Lys His
                245                 250                 255

Pro Leu Arg Gln Lys Phe Glu Ser Ala Val Arg Glu Thr Ile Ser Gln
                260                 265                 270

Val Lys Arg Leu Arg Asp Ile Asp Ile Ala Val Glu Thr Leu Gly Glu
                275                 280                 285

Tyr Asp Phe Val Glu Glu Val Phe Leu Gln Gln Met Asn Leu Gly Thr
                290                 295                 300

Gly Ser Ala Ser Ile Glu Met Thr Ala Pro Asp Ser Met Phe Tyr Thr
305                 310                 315                 320

Val Leu Gln Glu Glu Ser Gly Phe Thr Ile Thr Gly Glu His Asp Leu
                325                 330                 335
```

```
Leu Arg Leu Met Lys Glu Leu Ser Lys Ala Lys Arg Glu Tyr Asp Lys
                340                 345                 350

Val Ser Thr Ala Leu Glu Asp Val Arg Gln Asn Gly Tyr Gly Val Val
            355                 360                 365

Asn Pro Ser Leu Glu Glu Met Tyr Leu Glu Pro Glu Leu Ile Lys
        370                 375                 380

Gln Gly Asn Arg Phe Gly Val Lys Leu Lys Ala Ser Ala Pro Ser Leu
385                 390                 395                 400

His Ile Ile Arg Ala Asp Ile Thr Thr Glu Ile Thr Pro Ile Ile Gly
                405                 410                 415

Thr Glu Lys Gln Cys Glu Glu Leu Val Arg Tyr Ile Leu Glu Glu Phe
            420                 425                 430

Glu Glu Asn Pro Gln Lys Ile Trp Glu Ser Asn Ile Phe Gly Lys Ser
        435                 440                 445

Leu His Asp Leu Val Arg Gly Val Gln Asn Lys Leu Gln Arg Met
    450                 455                 460

Pro Glu Asn Val Gln Gly Lys Leu Gln Glu Thr Leu Gln Arg Ile Val
465                 470                 475                 480

Asn Glu Gly Asn Gly Gly Leu Ile Cys Ile Ile Ile
                485                 490

<210> SEQ ID NO 28
<211> LENGTH: 492
<212> TYPE: PRT
<213> ORGANISM: Clostridium acetobutylicum

<400> SEQUENCE: 28

Met Glu Asn Phe Asn Ile Tyr Lys Asp Ile Ala Glu Arg Thr Asp Gly
1               5                   10                  15

Asp Ile Tyr Val Gly Val Val Gly Pro Val Arg Thr Gly Lys Ser Thr
                20                  25                  30

Phe Ile Lys Arg Phe Met Asp Thr Met Val Ile Pro Asn Ile Asp Asn
            35                  40                  45

Pro His Lys Lys Glu Arg Ala Lys Asp Glu Leu Pro Gln Ser Ser Ser
        50                  55                  60

Gly Lys Thr Ile His Thr Thr Glu Pro Lys Phe Val Pro Asn Glu Ala
65                  70                  75                  80

Val Asp Ile Ser Leu Ser Glu Gly Ile Lys Leu Lys Val Arg Leu Val
                85                  90                  95

Asp Cys Val Gly Tyr Ile Val Lys Ser Ala Leu Gly Tyr Ala Glu Ala
                100                 105                 110

Asp Lys Pro Lys Met Val Ser Thr Pro Trp Phe Asp His Glu Ile Pro
            115                 120                 125

Phe Glu Lys Ala Ala Glu Ile Gly Thr Lys Lys Val Ile Asp Glu His
        130                 135                 140

Ser Thr Ile Gly Leu Val Val Thr Thr Asp Gly Ser Ile Thr Gly Ile
145                 150                 155                 160

Pro Arg Glu Asp Tyr Val Glu Ala Glu Glu Arg Val Val Lys Glu Leu
                165                 170                 175

Lys Glu Ile Lys Lys Pro Phe Val Ile Ile Leu Asn Ser Ser Gln Val
            180                 185                 190

Asp Asp Pro Lys Thr Ile Glu Leu Arg Asp Glu Leu Glu Lys Lys Tyr
        195                 200                 205

Asp Val Ser Val Gln Val Leu Asp Val Gln Asn Met Val Glu Glu Asp
        210                 215                 220
```

```
Ile Ile Lys Val Phe Ser Lys Ile Leu Arg Glu Phe Pro Val Arg Glu
225                 230                 235                 240

Ile Asn Ile Asp Met Pro Glu Trp Ile Glu Lys Leu Ser Thr Lys His
            245                 250                 255

Trp Leu Lys Asp Asn Phe Met Asn Ile Ile Lys Glu Ile Cys Ile Lys
            260                 265                 270

Val Asn Lys Val Arg Asp Ile Ser Lys Ile Val Ala Ser Tyr Ser Gly
        275                 280                 285

Met Asp Tyr Leu Asp Lys Ala Asp Met Thr Glu Met Asp Met Gly Ser
    290                 295                 300

Gly Val Gly Arg Ile Val Phe Thr Pro Lys Arg Asp Met Phe Tyr Lys
305                 310                 315                 320

Val Leu Ser Glu Glu Cys Glu Cys Asp Ile Asp Gly Glu Asn Lys Leu
            325                 330                 335

Leu Ser Ile Met Lys Glu Met His Glu Ala Lys Val Gln Tyr Asp Arg
            340                 345                 350

Ile Ser Glu Ala Leu Lys Asp Val Arg Glu Lys Gly Tyr Gly Leu Val
        355                 360                 365

Ala Pro Gln Leu Thr Glu Met Lys Leu Glu Glu Pro Lys Ile Val Lys
    370                 375                 380

Ser Gly Ala Arg Tyr Glu Val Lys Leu Lys Ala Ser Ala Pro Ser Phe
385                 390                 395                 400

His Phe Ile Arg Ala Asp Ile Glu Thr Glu Val Ser Pro Ile Met Gly
            405                 410                 415

Ser Glu Arg Glu Ser Glu Glu Leu Val Arg Ser Leu Leu Glu Gln Phe
            420                 425                 430

Glu Asn Asp Pro Ser Glu Ile Trp Glu Ser Asn Met Phe Gly Lys Ser
            435                 440                 445

Leu Glu Val Leu Val Lys Glu Gly Leu Gln Lys Lys Leu Tyr Lys Met
    450                 455                 460

Pro Asp Asp Val Gln Ala Lys Ile Gln Lys Thr Leu Glu Lys Ile Ile
465                 470                 475                 480

Asn Glu Gly Asn Gly Gly Leu Ile Cys Ile Ile Leu
            485                 490
```